US012544089B1

(12) United States Patent
Farrow et al.

(10) Patent No.: US 12,544,089 B1
(45) **Date of Patent: *Feb. 10, 2026**

(54) WOUND-CARE APPARATUS AND METHOD FOR CLEANSING, DESLOUGHING, AND DEBRIDING WOUNDS

(71) Applicant: Farrow Medtech LLC, College Station, TX (US)

(72) Inventors: Wade P. Farrow, Charlotte, NC (US); Adrian Slattery, Rocky River, OH (US); Douglas R. Halley, Westlake, OH (US)

(73) Assignee: Farrow Medtech LLC, College Station, TX (US)

( * ) Notice: Subject to any disclaimer, the term of this patent is extended or adjusted under 35 U.S.C. 154(b) by 568 days.

This patent is subject to a terminal disclaimer.

(21) Appl. No.: 18/074,475

(22) Filed: Dec. 3, 2022

Related U.S. Application Data

(63) Continuation-in-part of application No. 17/133,212, filed on Dec. 23, 2020, now Pat. No. 11,980,383.

(60) Provisional application No. 62/953,441, filed on Dec. 24, 2019.

(51) Int. Cl.
*A61B 17/32* (2006.01)
*A61B 17/00* (2006.01)

(52) U.S. Cl.
CPC .... *A61B 17/32* (2013.01); *A61B 2017/00761* (2013.01); *A61B 2017/320004* (2013.01); *A61B 2217/007* (2013.01)

(58) Field of Classification Search
CPC .......... A61B 17/320068; A61B 2017/320008; A61B 2017/320078; A61B 2217/007; A61B 2017/320084; A61B 2017/00761; A61B 2017/320004; A61B 2017/32007
See application file for complete search history.

(56) References Cited

U.S. PATENT DOCUMENTS 6,478,754 B1 11/2002 Babaev
6,569,099 B1 5/2003 Babaev
6,663,554 B2 12/2003 Babaev
(Continued)

FOREIGN PATENT DOCUMENTS

WO 2005030297 A1 4/2005
WO 2013072357 A2 5/2013
WO 2014/210149 A1 12/2014

OTHER PUBLICATIONS

Extended European Search Report for Application No. EP 20905007.9 dated May 16, 2023.
(Continued)

*Primary Examiner* — Shaun L David
*Assistant Examiner* — Rachael L Geiger
(74) *Attorney, Agent, or Firm* — Young Basile Hanlon & MacFarlane, P.C.

(57) ABSTRACT

A method of assembling a wound-care device is disclosed. The method includes obtaining components of a wound-care device. The wound-care device includes a handle having a first end and a second end opposite the first end, a disposable sleeve, and a disposable head. The disposable head includes an aperture configured to receive the first end of the handle therewithin. The disposable sleeve is applied to the handle such that a portion of the disposable sleeve is positioned between an interior surface of the aperture and an exterior surface of the first end.

15 Claims, 83 Drawing Sheets

(56) References Cited

U.S. PATENT DOCUMENTS

| | | | |
|---|---|---|---|
| 6,761,729 | B2 | 7/2004 | Babaev |
| 6,916,296 | B2 | 7/2005 | Soring et al. |
| 6,960,173 | B2 | 11/2005 | Babaev |
| 7,025,735 | B2 | 4/2006 | Soring et al. |
| 7,431,704 | B2 | 10/2008 | Babaev |
| 7,572,268 | B2 | 8/2009 | Babaev |
| 7,608,054 | B2 | 10/2009 | Soring et al. |
| 7,713,218 | B2 | 5/2010 | Babaev et al. |
| 7,785,277 | B2 | 8/2010 | Babaev et al. |
| 7,785,728 | B2 | 8/2010 | Masel et al. |
| D627,463 | S | 11/2010 | Voic et al. |
| 7,842,032 | B2 | 11/2010 | Babaev |
| 7,878,991 | B2 | 2/2011 | Babaev |
| 7,896,854 | B2 | 3/2011 | Babaev |
| 7,896,855 | B2 | 3/2011 | Babaev |
| 7,901,388 | B2 | 3/2011 | Babaev |
| 7,914,470 | B2 | 3/2011 | Babaev |
| 7,931,611 | B2 | 4/2011 | Novak et al. |
| D644,326 | S | 8/2011 | Voic et al. |
| 8,025,672 | B2 | 9/2011 | Novak et al. |
| 8,050,752 | B2 | 11/2011 | Babaev |
| 8,052,705 | B2 | 11/2011 | Bar-On |
| 8,235,919 | B2 | 8/2012 | Babaev |
| 8,277,472 | B2 | 10/2012 | Babaev et al. |
| 8,430,897 | B2 | 4/2013 | Novak et al. |
| 8,562,547 | B2 | 10/2013 | Babaev |
| D699,839 | S | 2/2014 | Voic |
| D715,434 | S | 10/2014 | Darian |
| D715,435 | S | 10/2014 | Darian |
| D715,936 | S | 10/2014 | Darian |
| D733,319 | S | 6/2015 | Somers et al. |
| 9,119,658 | B2 | 9/2015 | Paraschiv et al. |
| D741,481 | S | 10/2015 | Darian et al. |
| 9,211,137 | B2 | 12/2015 | Voic |
| 9,320,528 | B2 | 4/2016 | Voic et al. |
| 9,387,005 | B2 | 7/2016 | Voic |
| 9,421,028 | B2 | 8/2016 | Darian |
| 9,622,766 | B2 | 4/2017 | Voic |
| 9,788,852 | B2 | 10/2017 | Voic |
| 9,872,697 | B2 | 1/2018 | Voic |
| 9,949,751 | B2 | 4/2018 | Voic |
| 10,092,308 | B2 | 10/2018 | Mikus et al. |
| 10,117,666 | B2 | 11/2018 | Voic |
| 10,149,735 | B2 | 12/2018 | Noell et al. |
| 10,219,822 | B2 | 3/2019 | Voic et al. |
| 10,299,809 | B2 | 5/2019 | Mikus et al. |
| 10,363,067 | B2 | 7/2019 | Hultquist |
| 11,980,383 | B2 * | 5/2024 | Farrow .......... A61B 17/320068 |
| 2003/0165550 | A1 | 9/2003 | Rhoades |
| 2004/0010250 | A1 | 1/2004 | R. Manna et al. |
| 2004/0030254 | A1 | 2/2004 | Babaev |
| 2008/0306501 | A1 | 12/2008 | Babaev |
| 2009/0157094 | A1 | 6/2009 | Yeshurun et al. |
| 2009/0192442 | A1 | 7/2009 | Ignon et al. |
| 2011/0009694 | A1 | 1/2011 | Schultz et al. |
| 2014/0330286 | A1 | 11/2014 | Wallace |
| 2015/0148712 | A1 | 5/2015 | Loven et al. |
| 2015/0182246 | A1 | 7/2015 | Grez |
| 2016/0143660 | A1 | 5/2016 | Castro et al. |
| 2016/0249951 | A1 | 9/2016 | Hultquist |
| 2017/0014145 | A1 | 1/2017 | Favie et al. |
| 2017/0072224 | A1 | 3/2017 | Frohwitter |
| 2017/0215906 | A1 | 8/2017 | Derk et al. |
| 2018/0177528 | A1 | 6/2018 | Domingos |
| 2019/0111238 | A1 | 4/2019 | Schultz et al. |
| 2019/0282073 | A1 * | 9/2019 | Truckai .................. A61B 1/051 |
| 2020/0179725 | A1 | 6/2020 | Loven et al. |

OTHER PUBLICATIONS

Translation of WO2013072357.

Written Opinion of the International Searching Authority for International Application No. PCT/US2020/067045, mailing date Mar. 30, 2021.

The Curason, www.curasonix.com/en/, webpage visited Sep. 14, 2021.

7 Need-to-Know Polypropylene Material Properties. Jan. 16, 2020. Coatings for Baskets and Racks. Retrieved from the Internet <URL: https://www.marlinwire.com/blog/7-need-to-know-polypropylene-material-properties#:-:text=Surface%20Hardness.,and%flex%20with%20an%20impact.>, (Year: 2020).

* cited by examiner

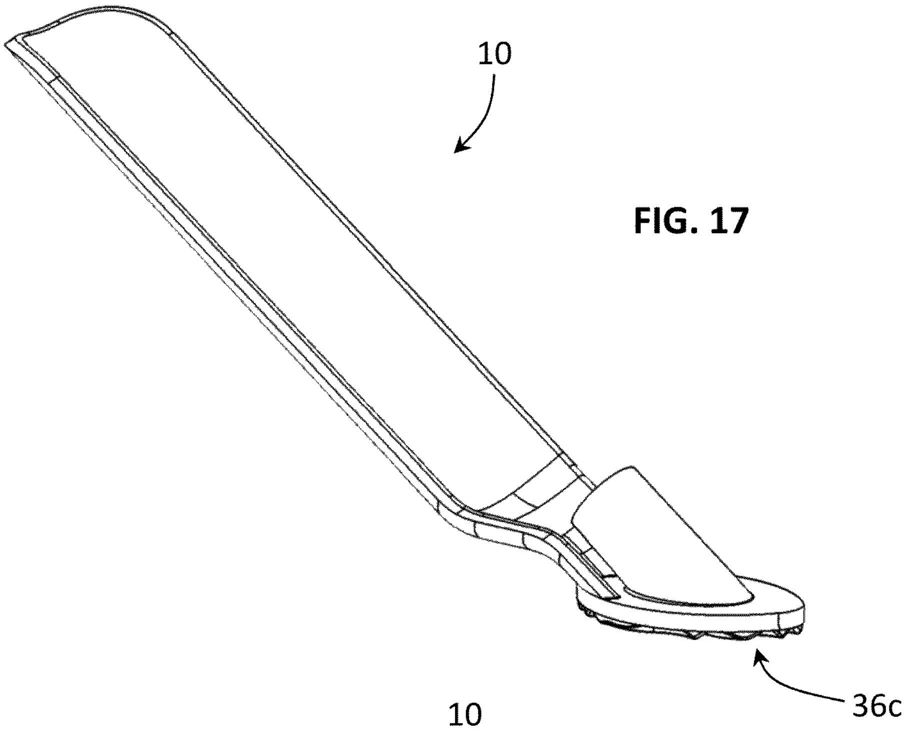
FIG. 17
FIG. 18
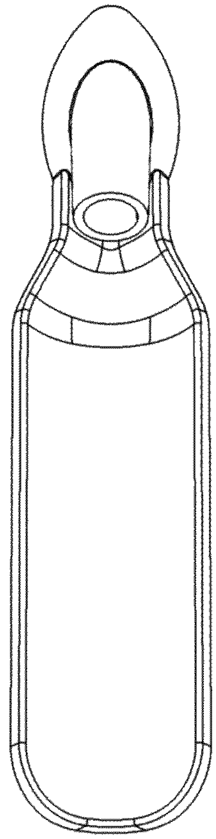
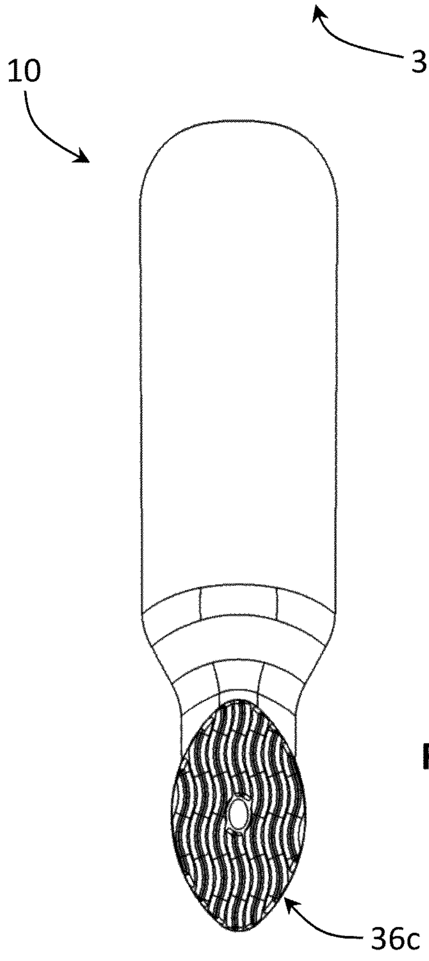
FIG. 19

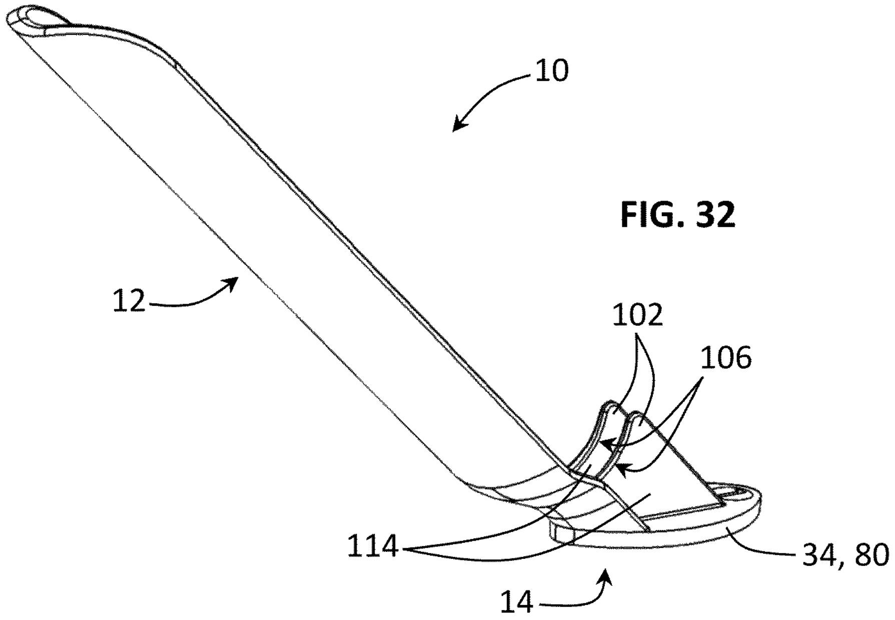
FIG. 32
FIG. 33
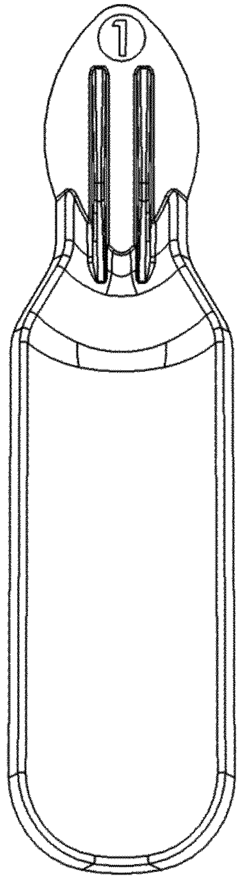
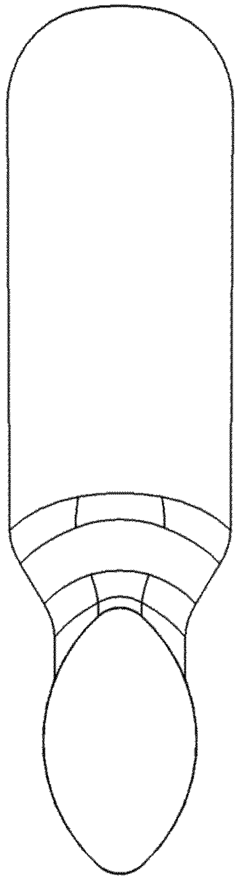
FIG. 34

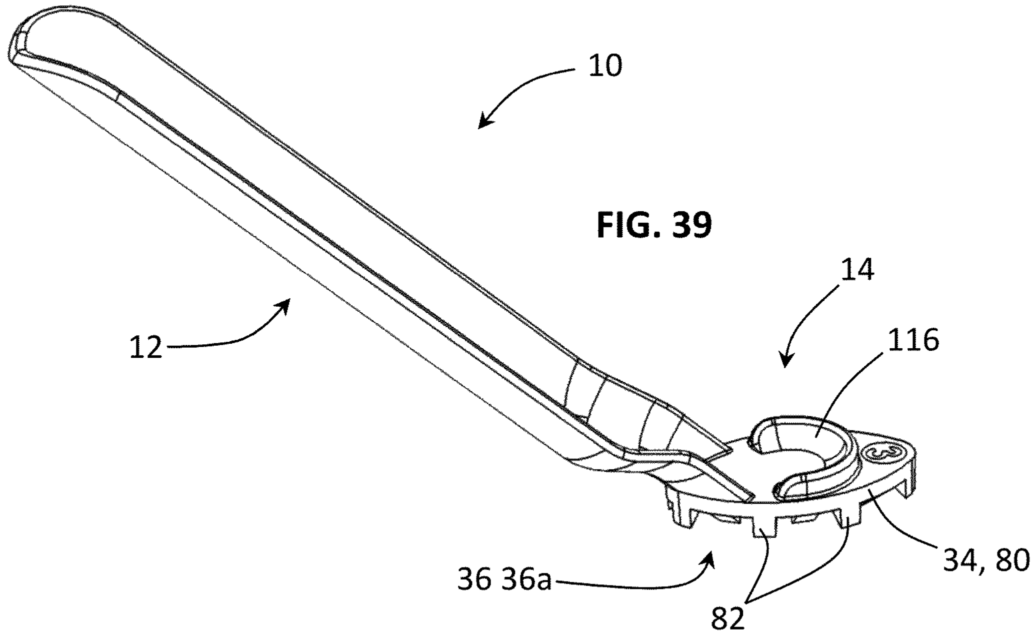
FIG. 39
FIG. 40
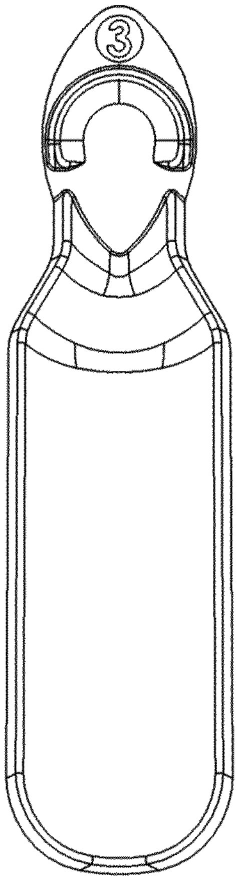
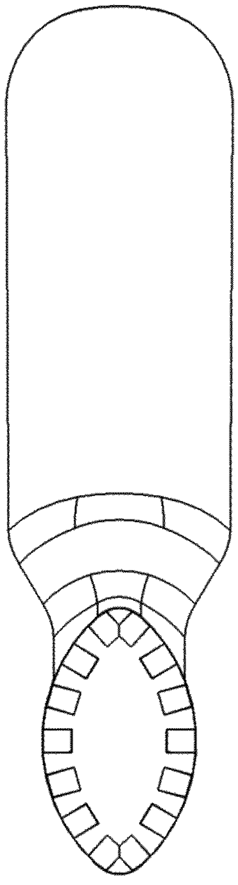
FIG. 41

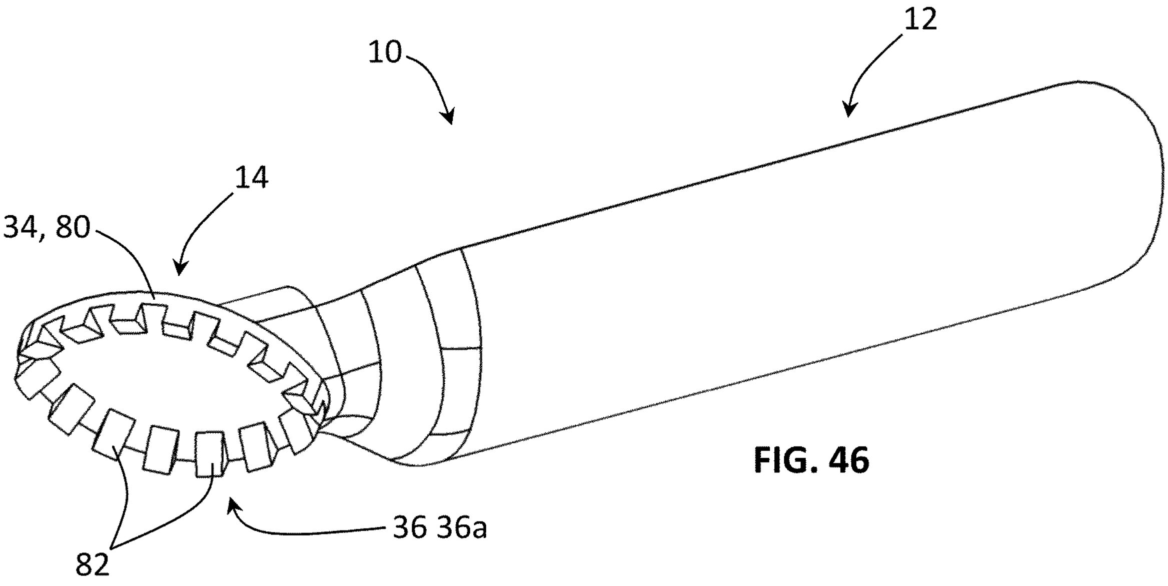
FIG. 46
FIG. 47
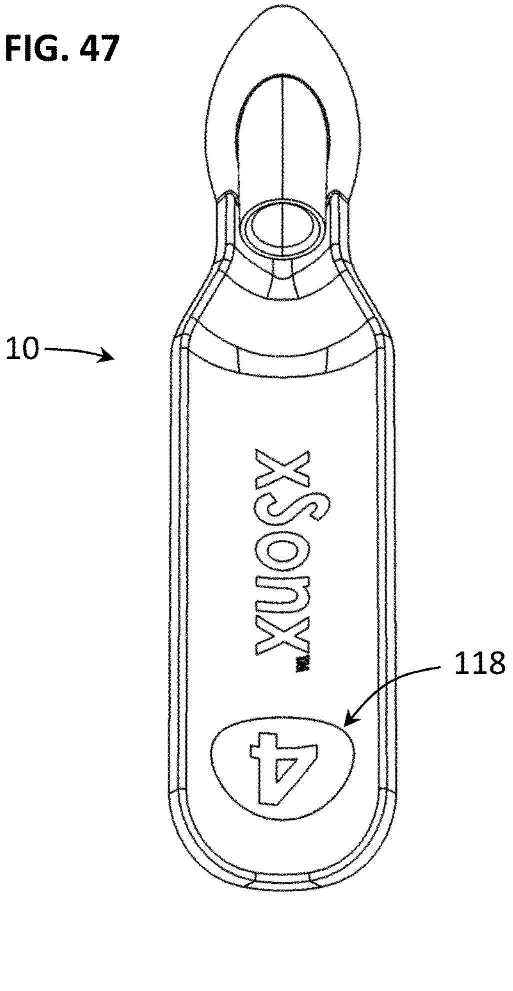
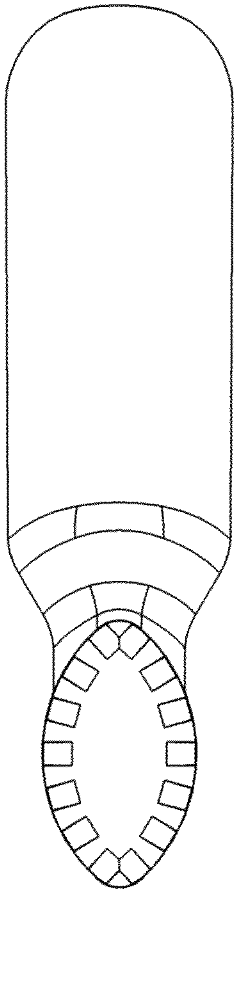
FIG. 48

FIG. 55
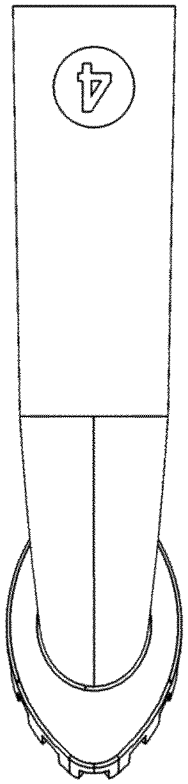
FIG. 56
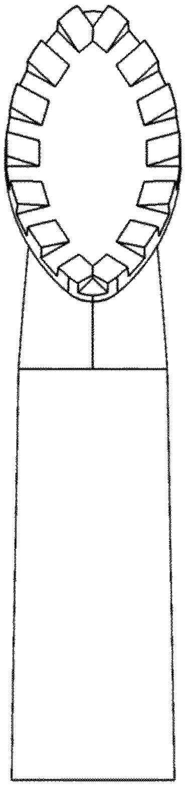
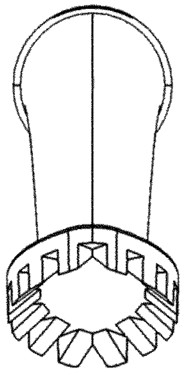
FIG. 57
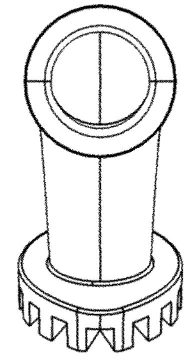
FIG. 58

FIG. 132
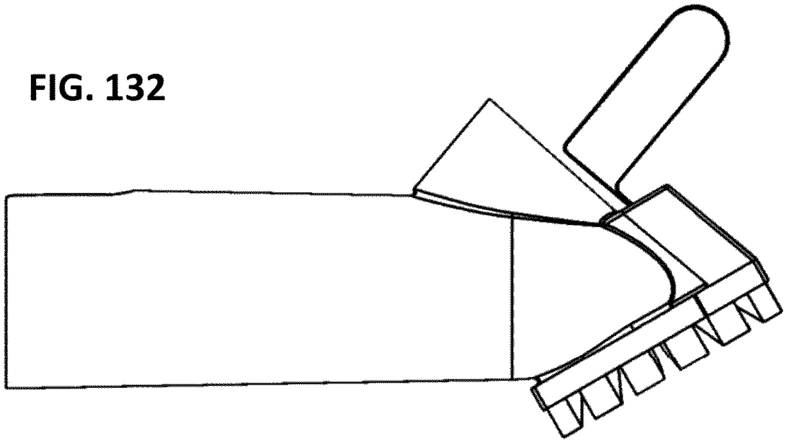
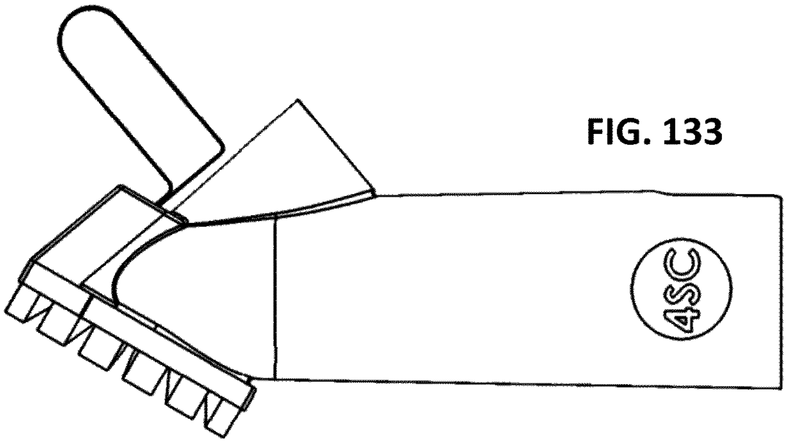
FIG. 133
FIG. 134
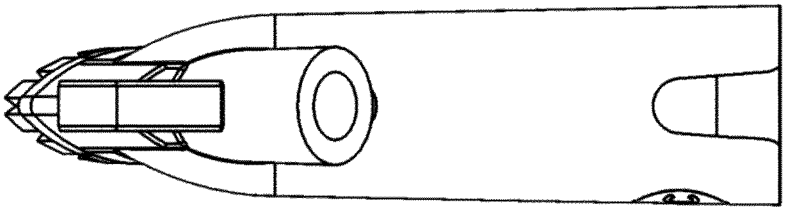
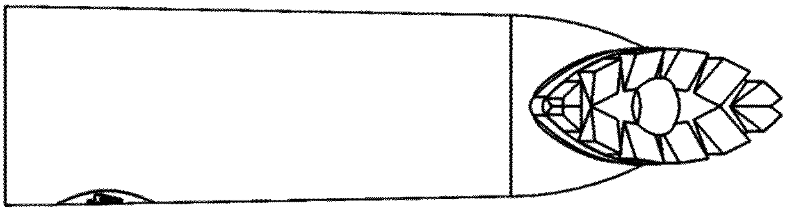
FIG. 135

WOUND-CARE APPARATUS AND METHOD FOR CLEANSING, DESLOUGHING, AND DEBRIDING WOUNDS

RELATED APPLICATIONS

This application is a continuation-in-part of U.S. patent application Ser. No. 17/133,212 filed Dec. 23, 2020, which claims the benefit of U.S. Provisional Patent Application Ser. No. 62/953,441 filed Dec. 24, 2019, both of which are hereby incorporated by reference.

BACKGROUND

Field of the Invention

This invention relates to wound care and, more particularly, to novel systems and methods for cleansing, desloughing, and debriding wounds.

Background Art

Different types of devitalized tissue commonly appear in wound beds. Such tissue may interrupt granulation and delay healing. For example, devitalized tissue may stimulate the overproduction of matrix metalloproteases (MMPs) and thereby slow the healing process. Additionally, devitalized tissue may provide an environment favorable to bacteria. Bacterial biofilms grow on 60-90% of chronic wounds and about 6% of acute wounds. Bacterial biofilms are low grade infections, cause chronic inflammation, impair wound healing, and increase risk of cellulitis. Various technologies and/or methods have been developed to improve wound care. However, those technologies and/or method have certain drawbacks. For example, ultrasonic debridement (e.g., debridement involving oscillations at about 20 kHz or above) is too expensive to be widely adopted. Conversely, pulse lavage is often too untidy for use in clinic or emergency room settings. Accordingly, what is needed are improved systems and methods for cleansing, desloughing, and debriding wounds and removing bacterial biofilms.

BRIEF DESCRIPTION OF THE DRAWINGS

The present invention will become fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 17 is a perspective view of the main body and head portions of the wound-care device of FIG. 10;

FIG. 18 is a top view of the main body and head portions of the wound-care device of FIG. 10;

FIG. 19 is a bottom view of the main body and head portions of the wound-care device of FIG. 10;

FIG. 32 is a perspective view of another alternative embodiment of a wound-care device;

FIG. 33 is a top view of the wound-care device of FIG. 32;

FIG. 34 is a bottom view of the wound-care device of FIG. 32;

FIG. 39 is a perspective view of another alternative embodiment of a wound-care device;

FIG. 40 is a top view of the wound-care device of FIG. 39;

FIG. 41 is a bottom view of the wound-care device of FIG. 39;

FIG. 46 is a perspective view of another alternative embodiment of a wound-care device;

FIG. 47 is a top view of the wound-care device of FIG. 46;

FIG. 48 is a bottom view of the wound-care device of FIG. 46;

FIG. 55 is a top view of the removable head of FIG. 53;

FIG. 56 is a bottom view of the removable head of FIG. 53;

FIG. 57 is a front view of the removable head of FIG. 53;

FIG. 58 is a rear view of the removable head device of FIG. 53;

FIG. 119 is a perspective view of another alternative embodiment of a head that may be applied to a wound-care device (e.g., the wound-care device of FIG. 105);

FIG. 120 is another perspective view of the head of FIG. 119;

FIG. 121 is a first side view of the head of FIG. 119;

FIG. 122 is a second, opposite side view of the head of FIG. 119;

FIG. 123 is a first end view of the head of FIG. 119;

FIG. 124 is a second, opposite end view of the head of FIG. 119;

FIG. 125 is a top view of the head of FIG. 119;

FIG. 126 is a bottom view of the head of FIG. 119;

FIG. 127 is a side cross-sectional view of the head of FIG. 119;

FIG. 128 is a side cross-sectional view of the head of FIG. 119 with a protective cover installed;

FIG. 129 is a perspective view of the head of FIG. 119 with a protective cover installed;

FIG. 130 is a perspective view of another alternative embodiment of a head that may be applied to a wound-care device (e.g., the wound-care device of FIG. 105);

Figure 105:
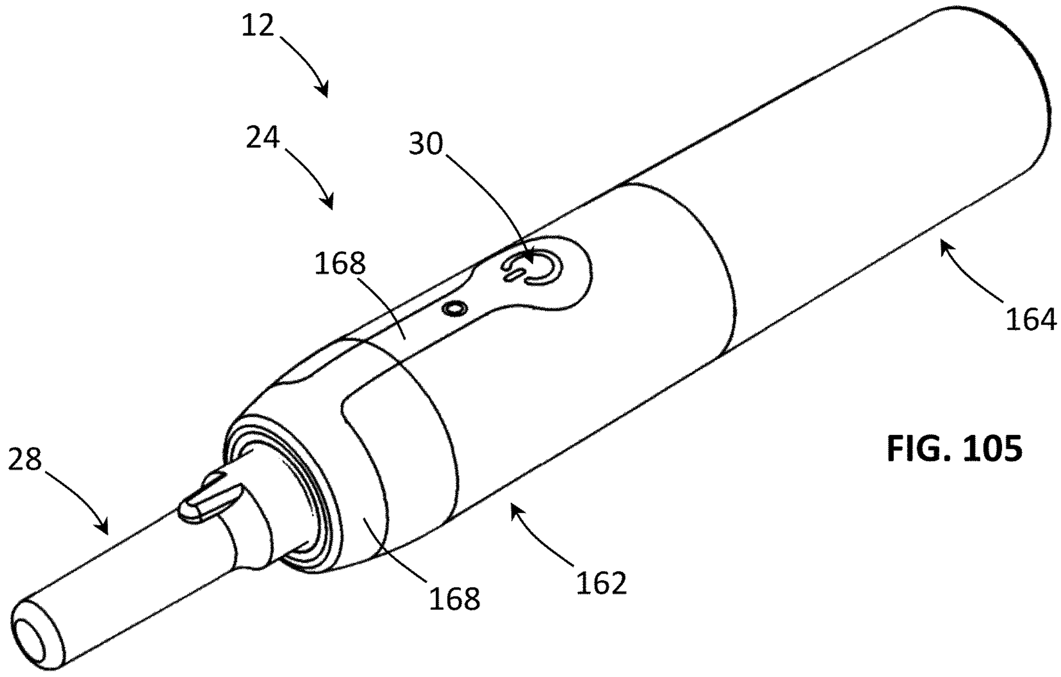
FIG. 105 is a perspective view of an alternative embodiment of a wound-care device.
Figure 106:
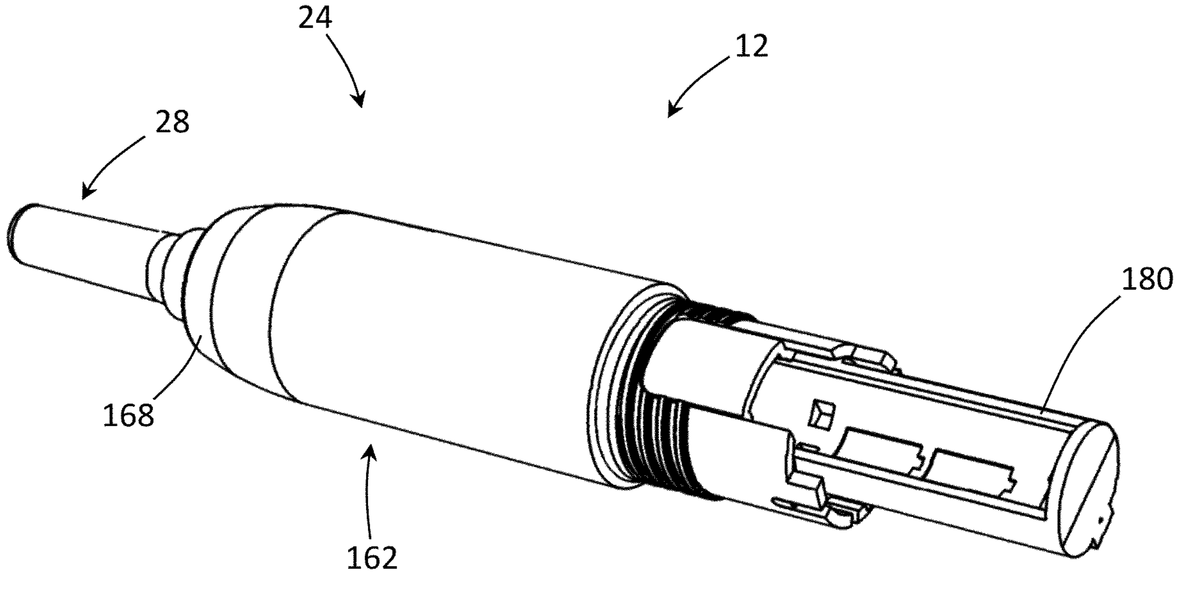
FIG. 106 is a perspective view of the wound-care device of FIG. 105 with a portion of the housing removed to expose a battery compartment for receiving batteries.
Figure 107:
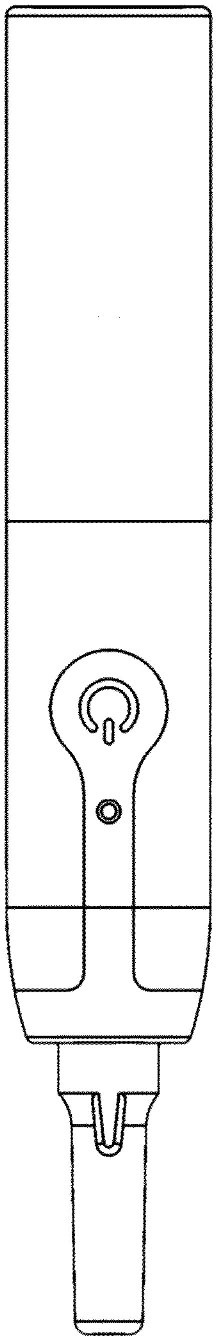
FIG. 107 is a top view of the wound-care device of FIG. 105.
Figure 108:
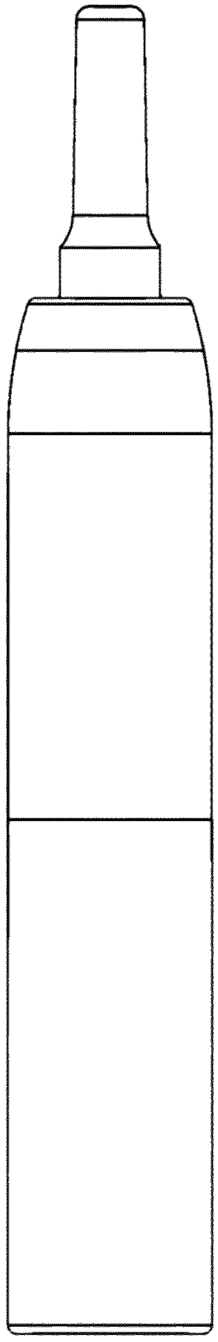
FIG. 108 is a bottom view of the wound-care device of FIG. 105.
Figure 109:
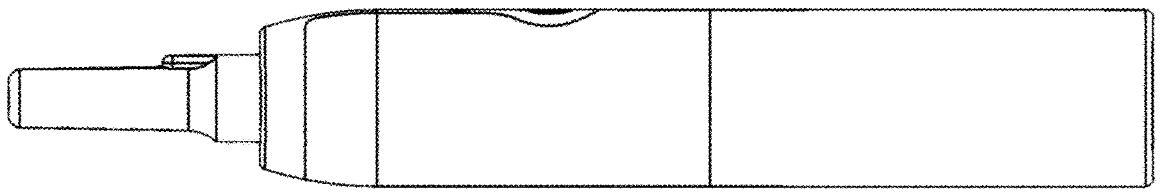
FIG. 109 is a first side view of the wound-care device of FIG. 105.
Figure 110:
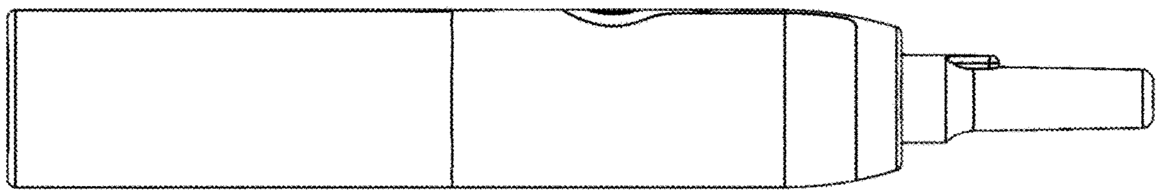
FIG. 110 is a second, opposite side view of the wound-care device of FIG. 105.
Figure 111:
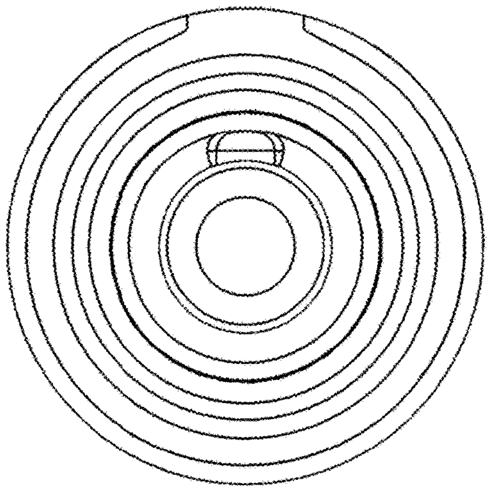
FIG. 111 is a first end view of the wound-care device of FIG. 105.
Figure 112:
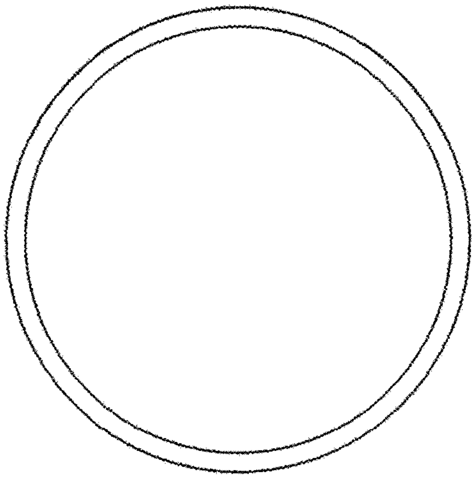
FIG. 112 is a second, opposite end view of the wound-care device of FIG. 105.
Figure 113:
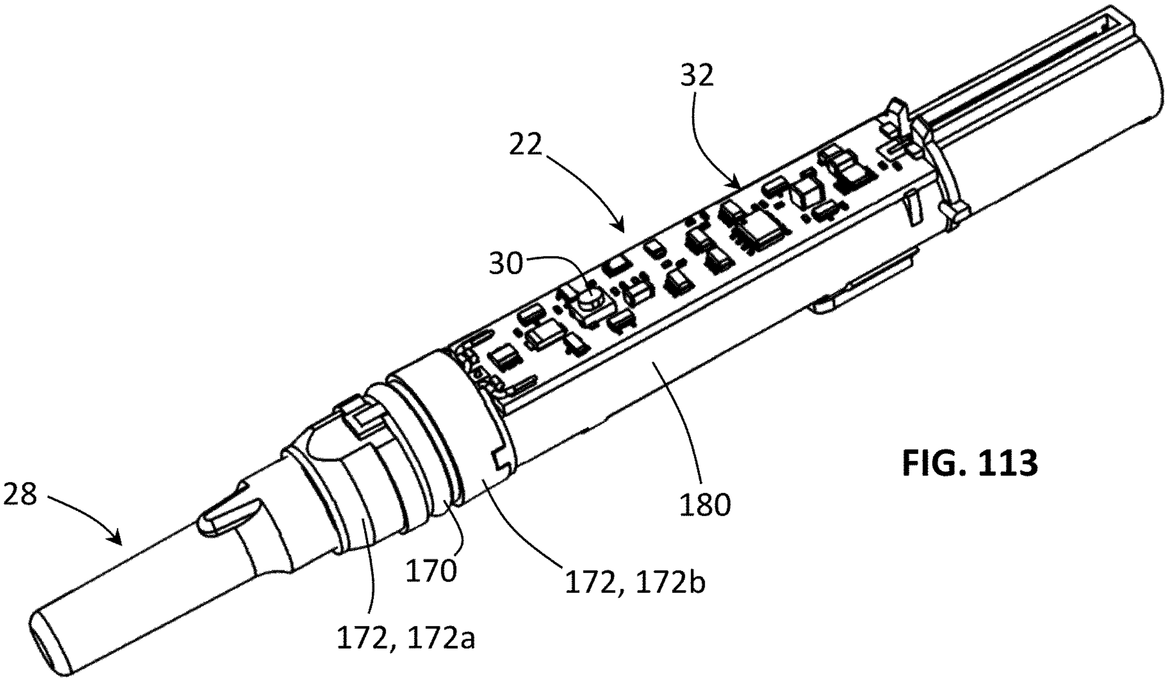
FIG. 113 is a perspective view of the wound-care device of FIG. 105 with the housing removed.
Figure 114:
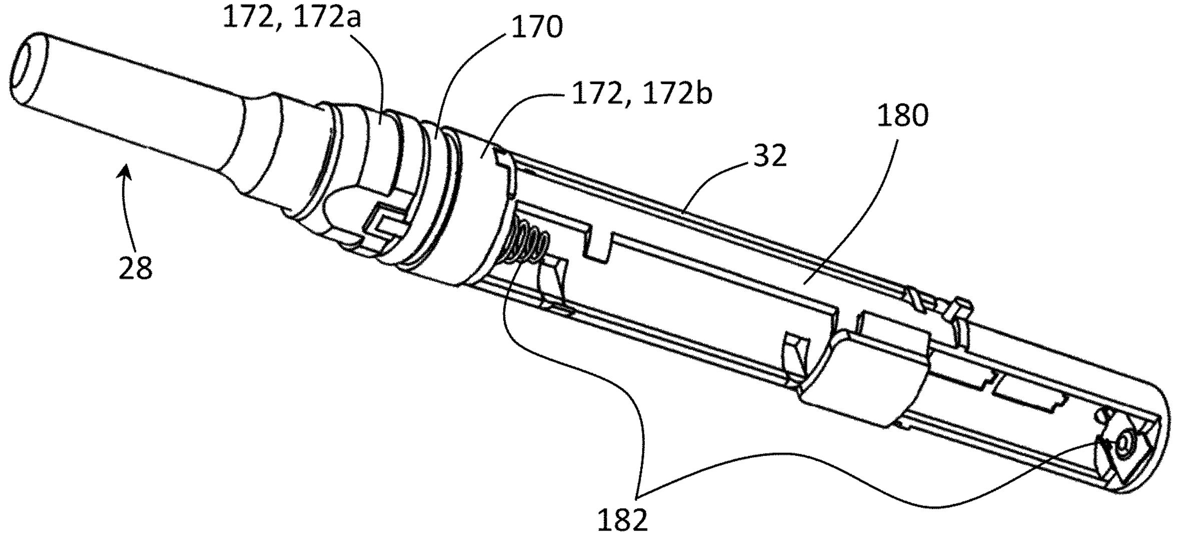
FIG. 114 is another perspective view of the wound-care device of FIG. 105 with the housing removed.
Figure 115:
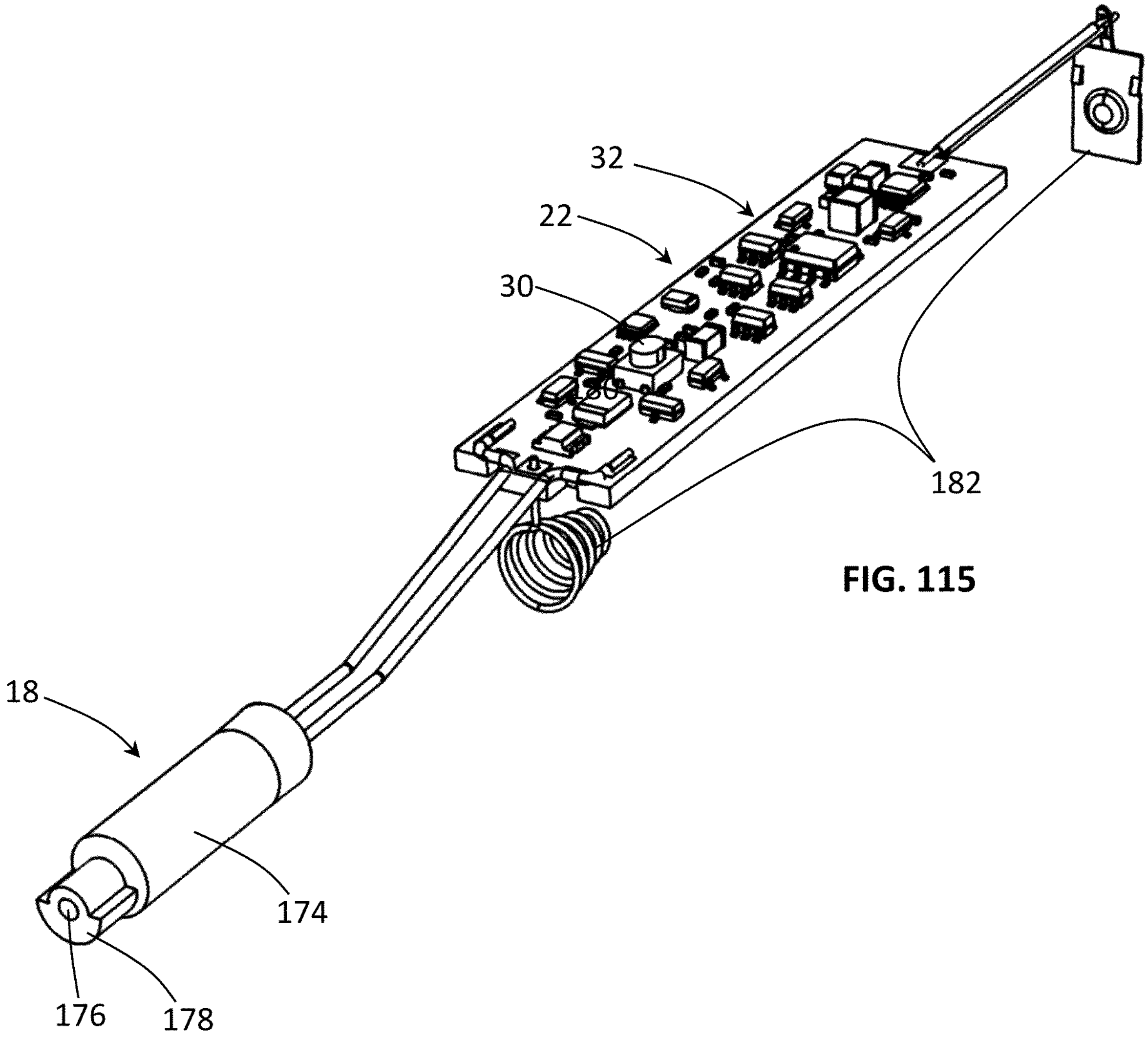
FIG. 115 is a perspective view of selected electrical components (i.e., motion generator, circuit board, battery terminals) of the wound-care device of FIG. 105.
Figure 116:
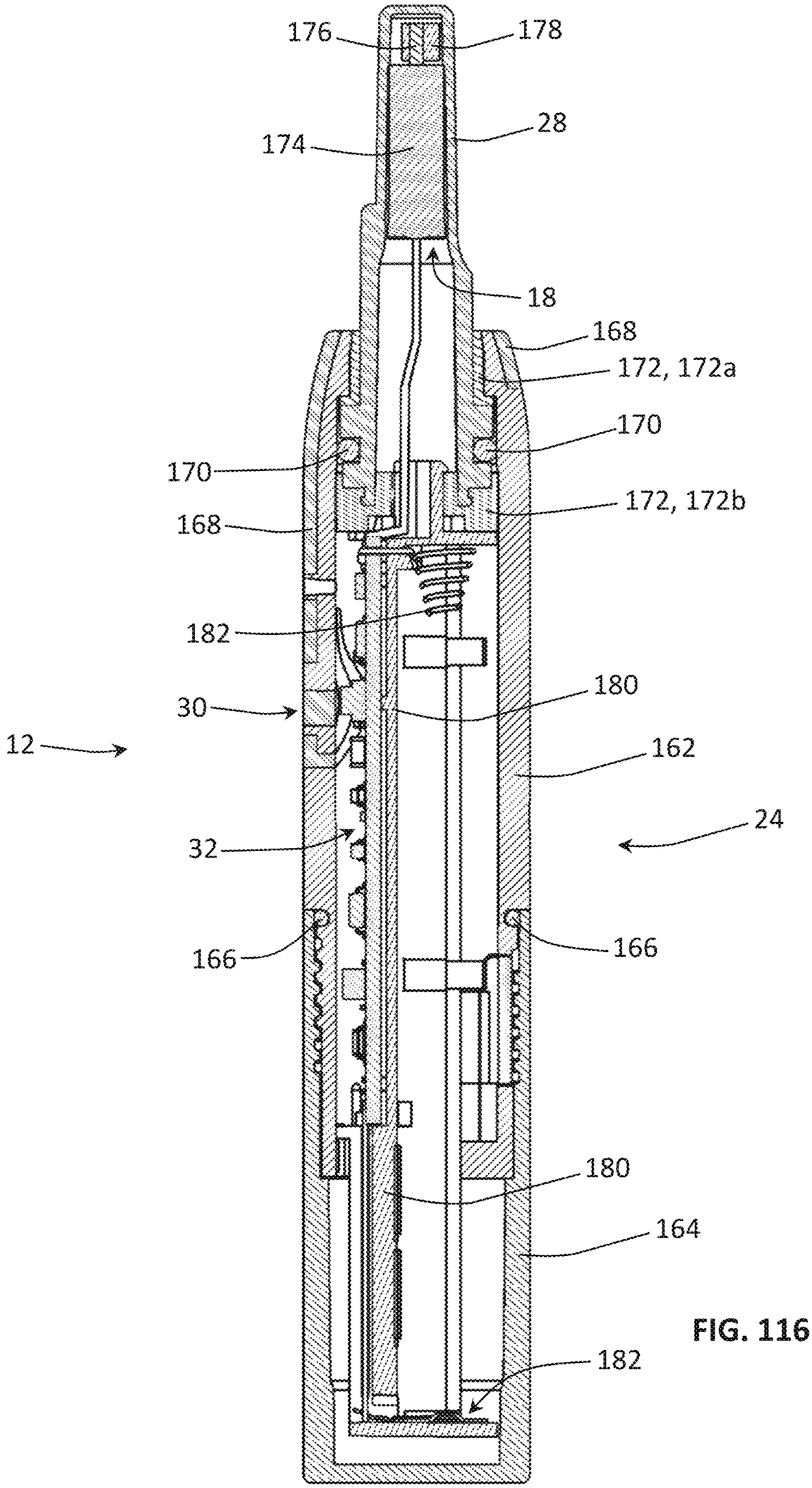
FIG. 116 is a side cross-sectional view of the wound-care device of FIG. 105.
Figure 130:
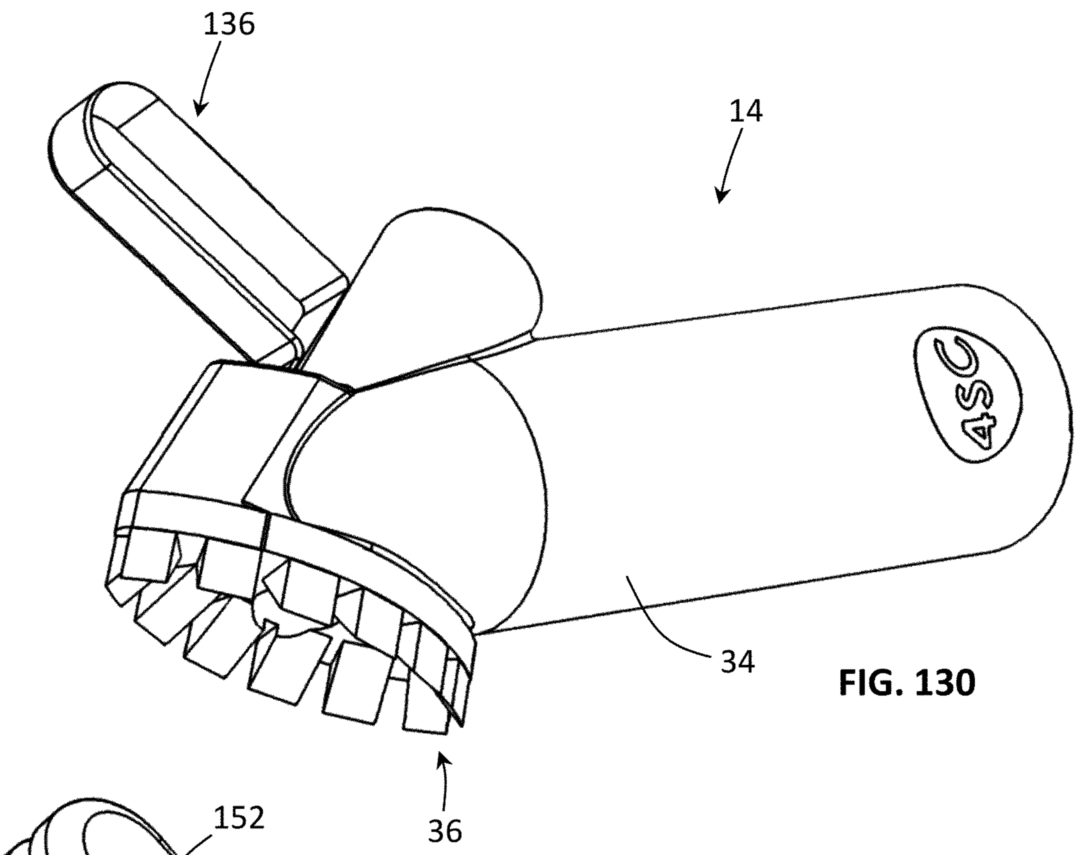
Figure 131:
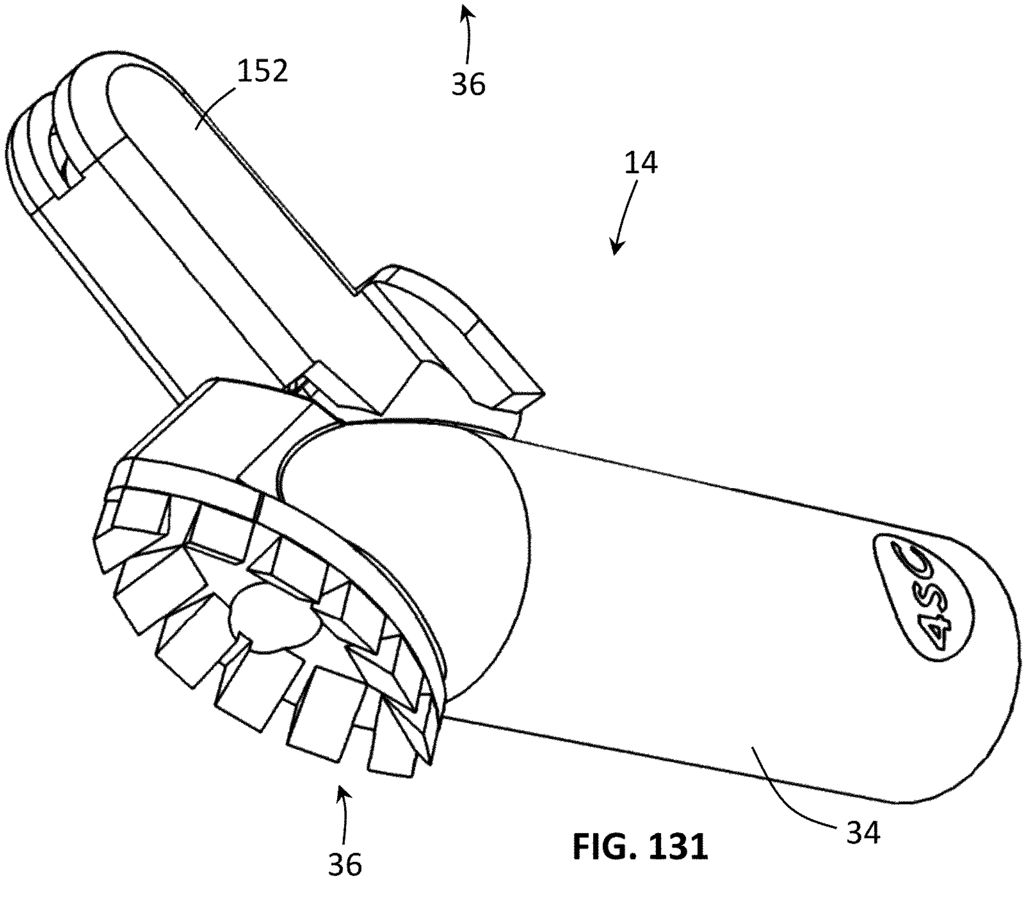
Figure 136:
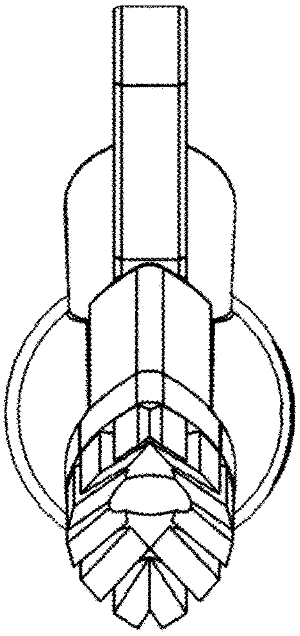
Figure 137:
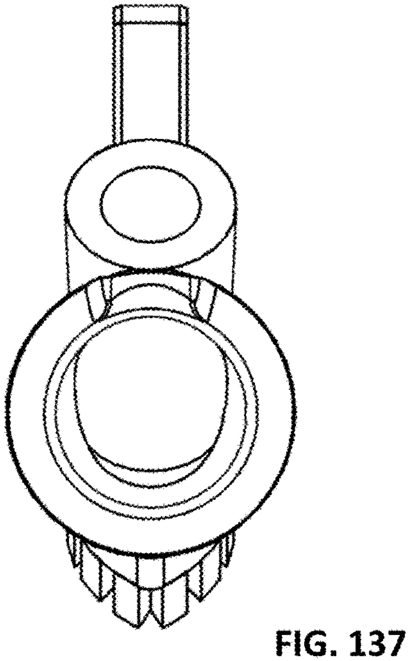
Figure 138:
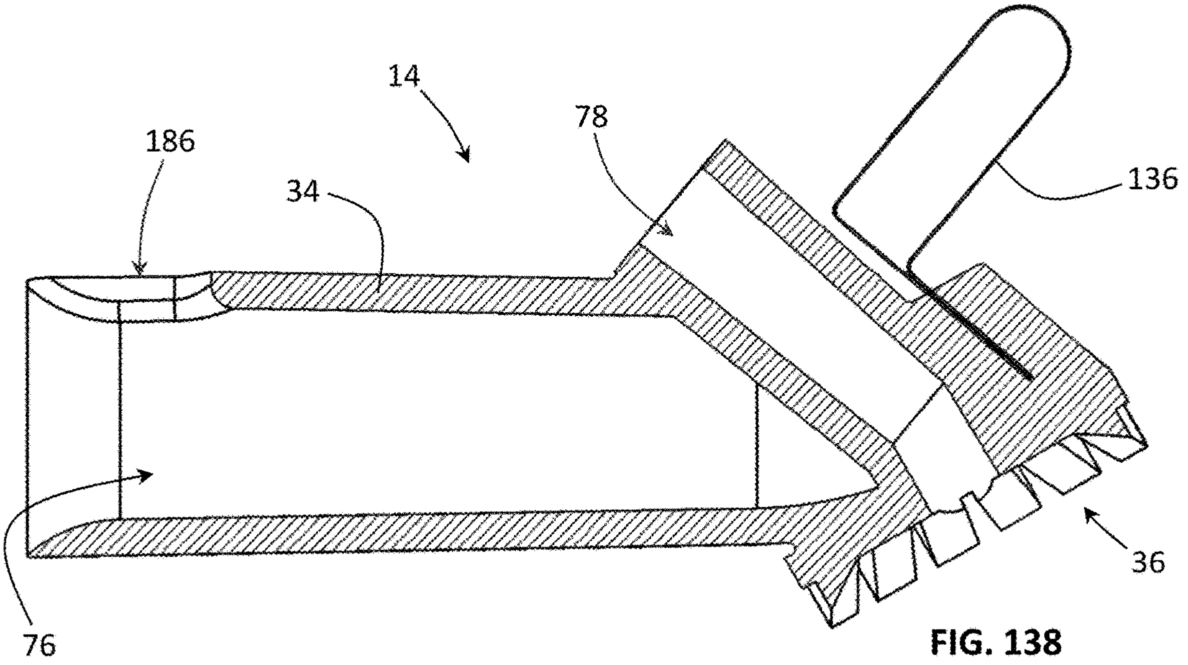
Figure 139:
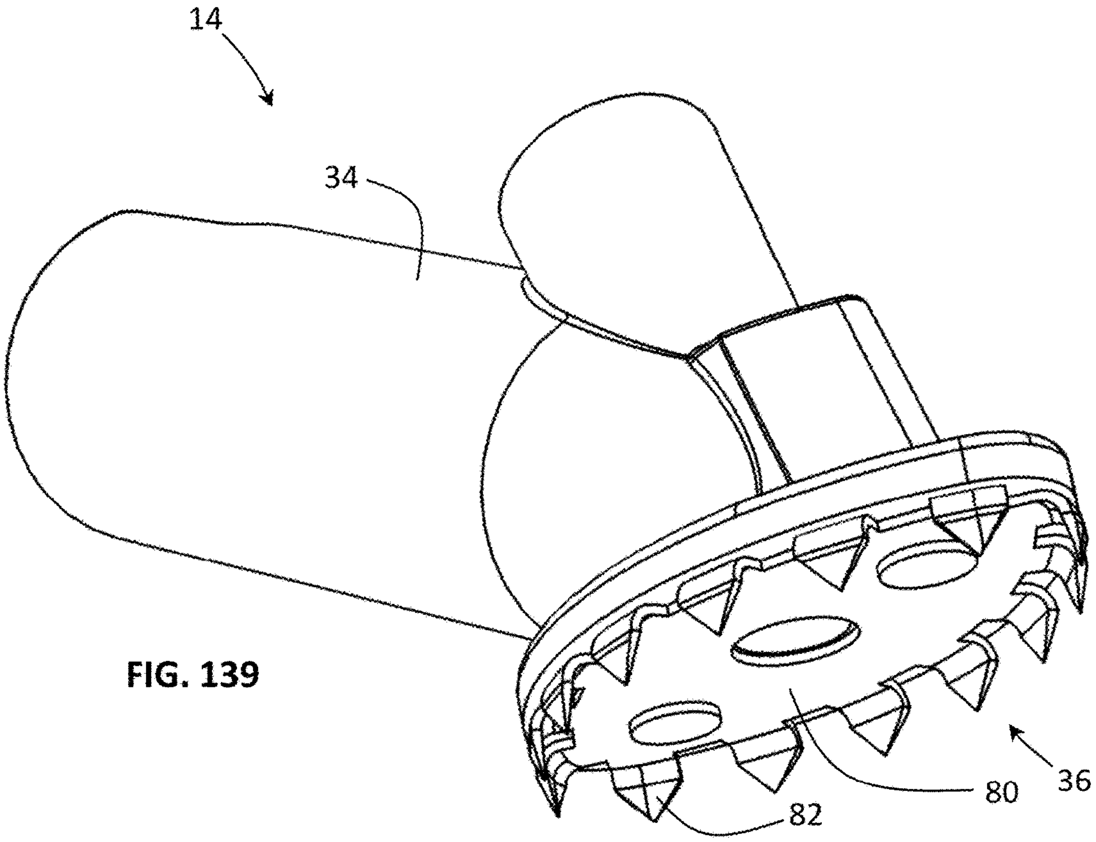
Figure 140:
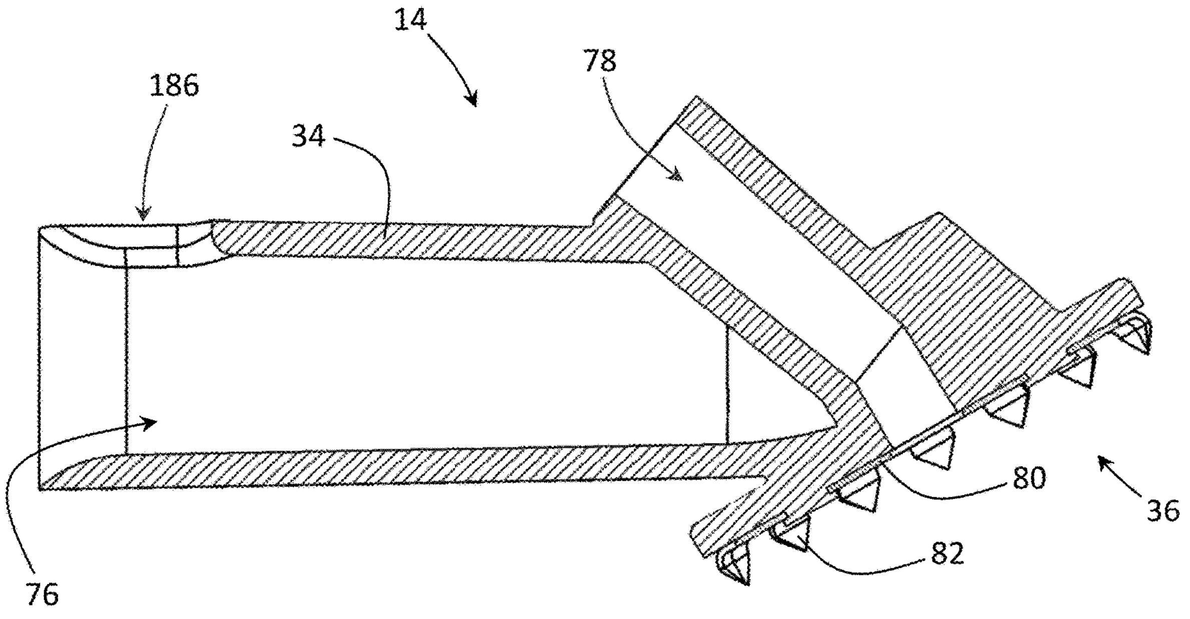
Figure 141:
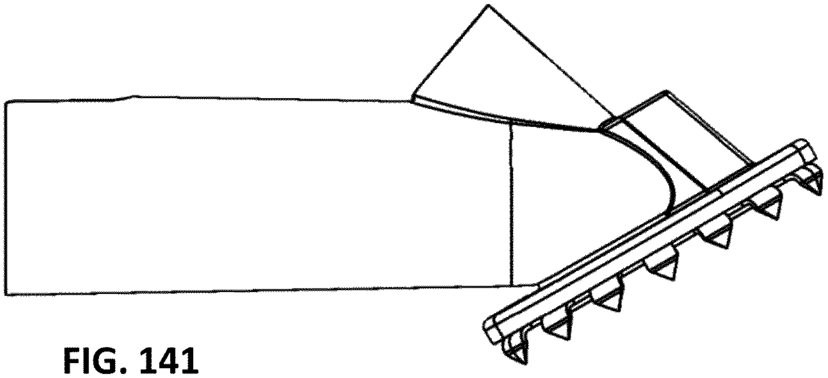
Figure 142:
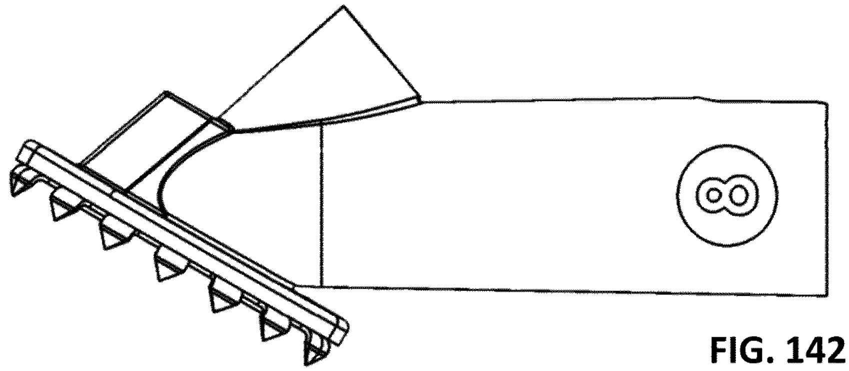
Figure 143:
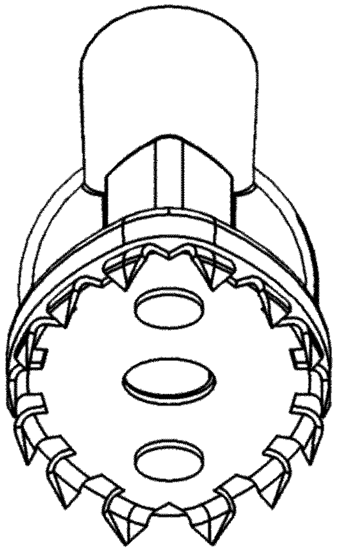
Figure 144:
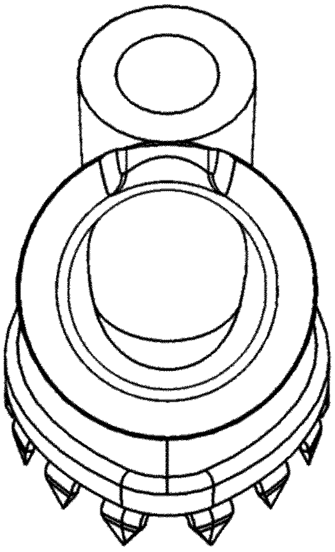
Figure 145:
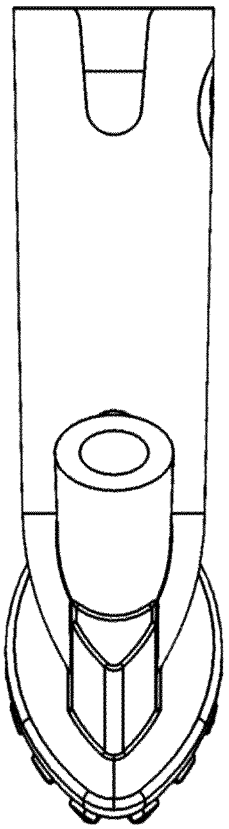
Figure 146:
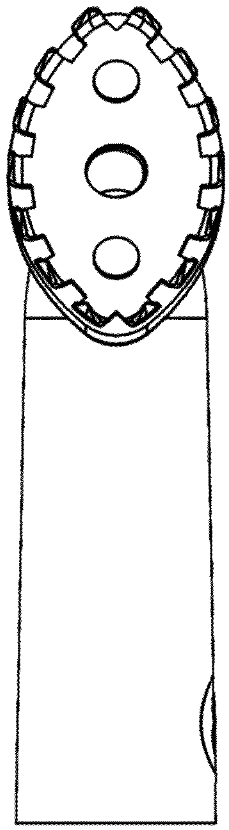
Figure 147:
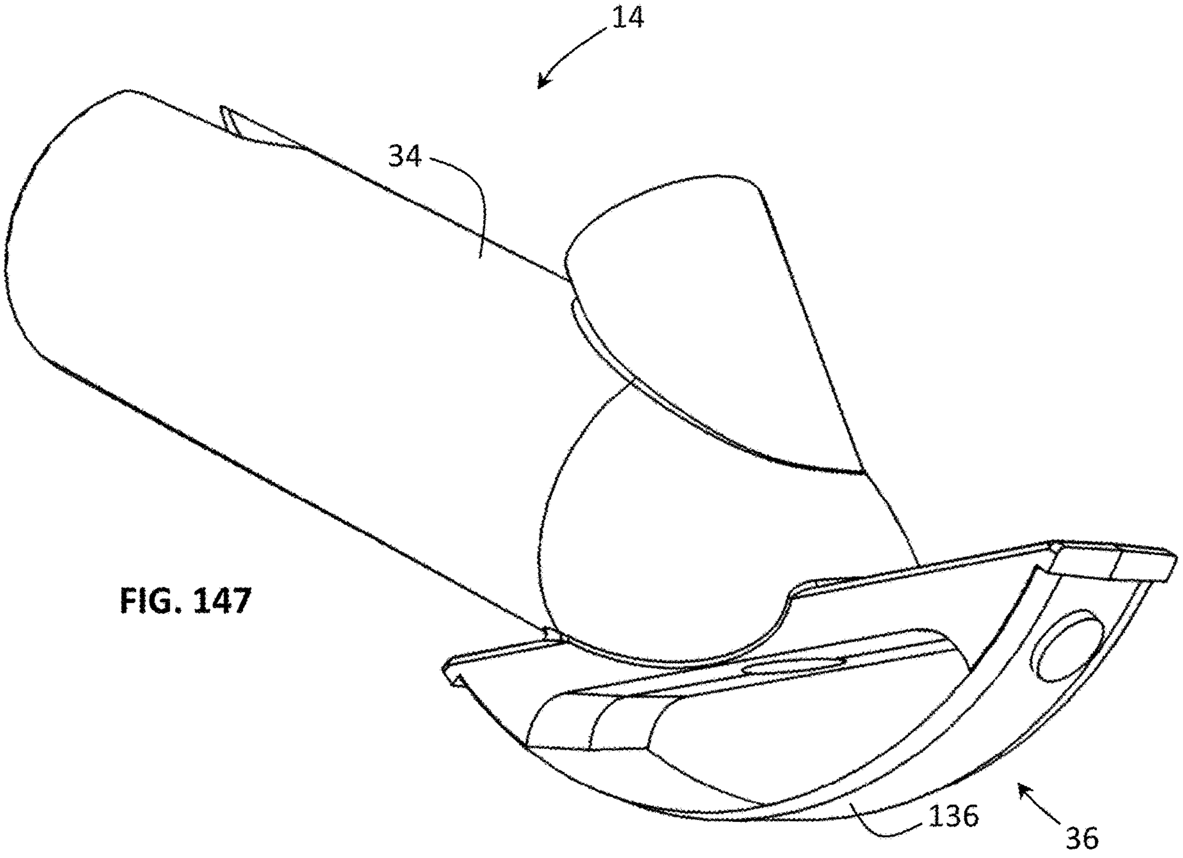
Figure 148:
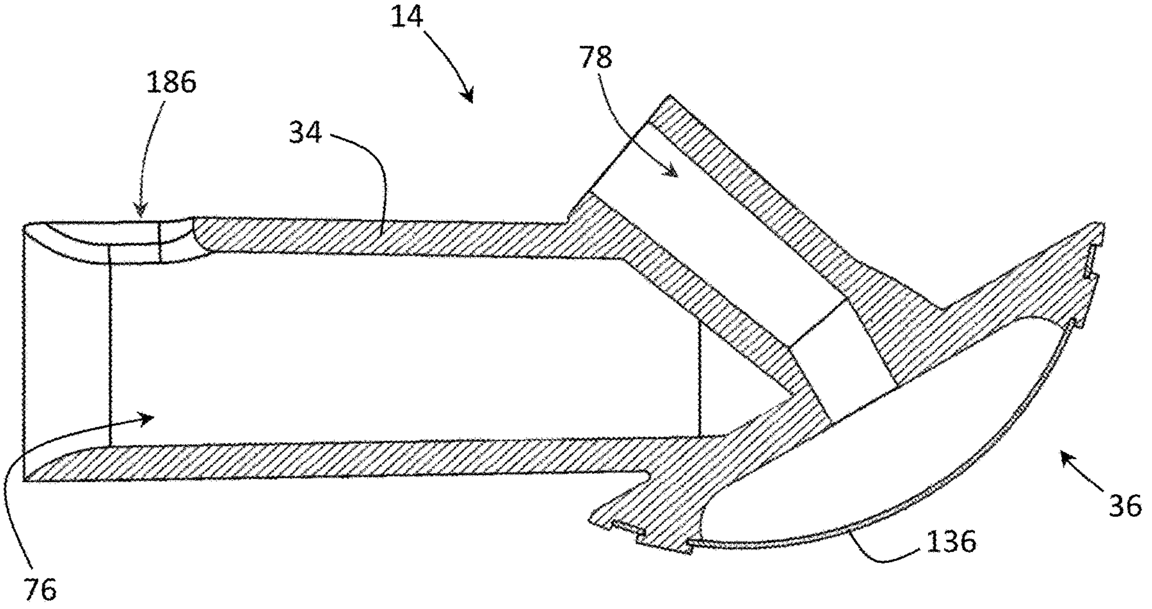
Figure 149:
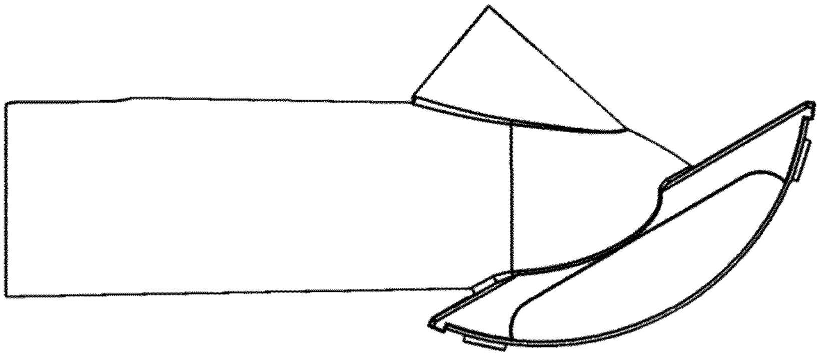
Figure 150:
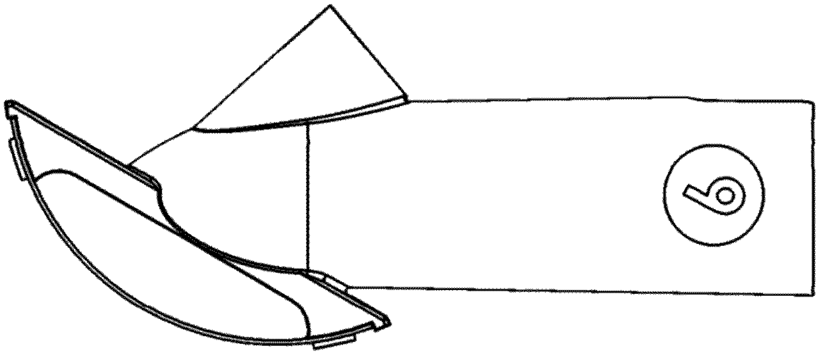
Figure 151:
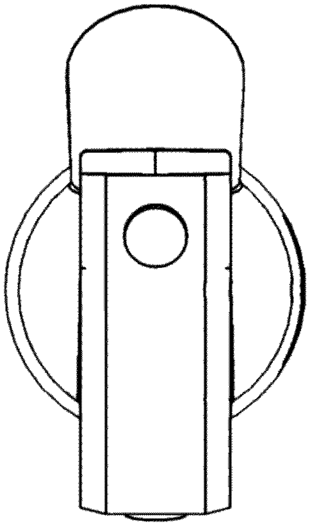
Figure 152:
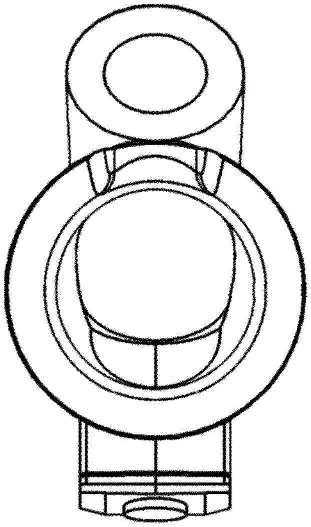
Figure 153:
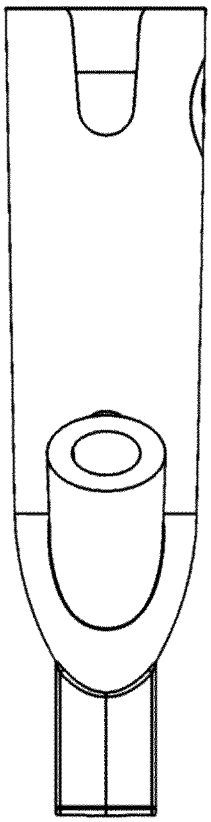
Figure 154:
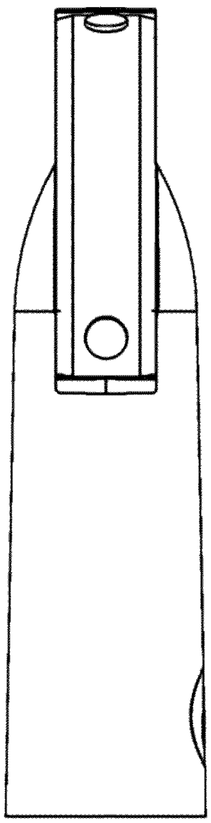
Figure 155:
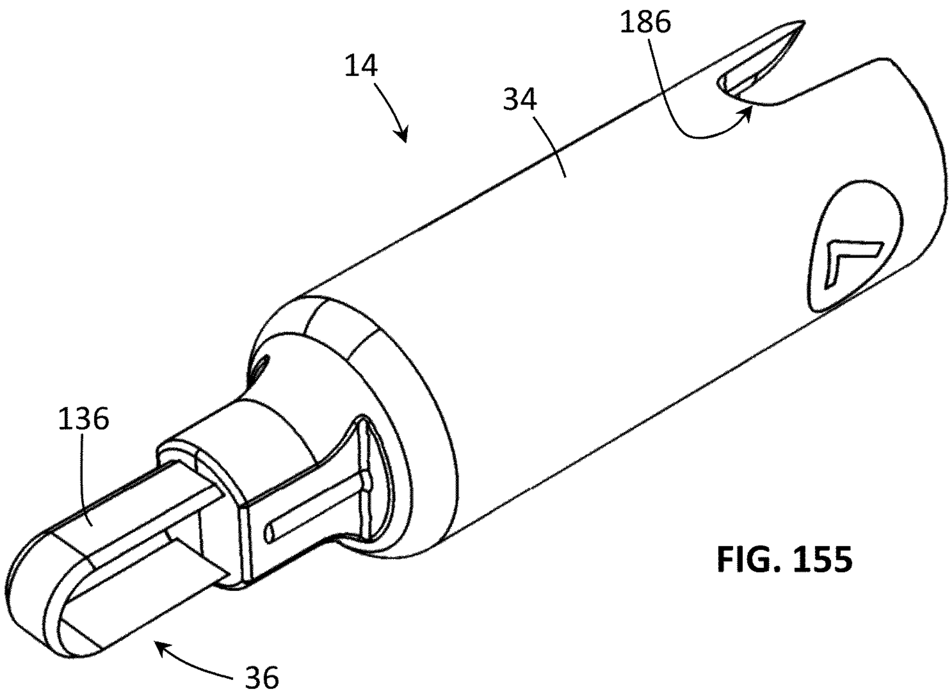
Figure 156:
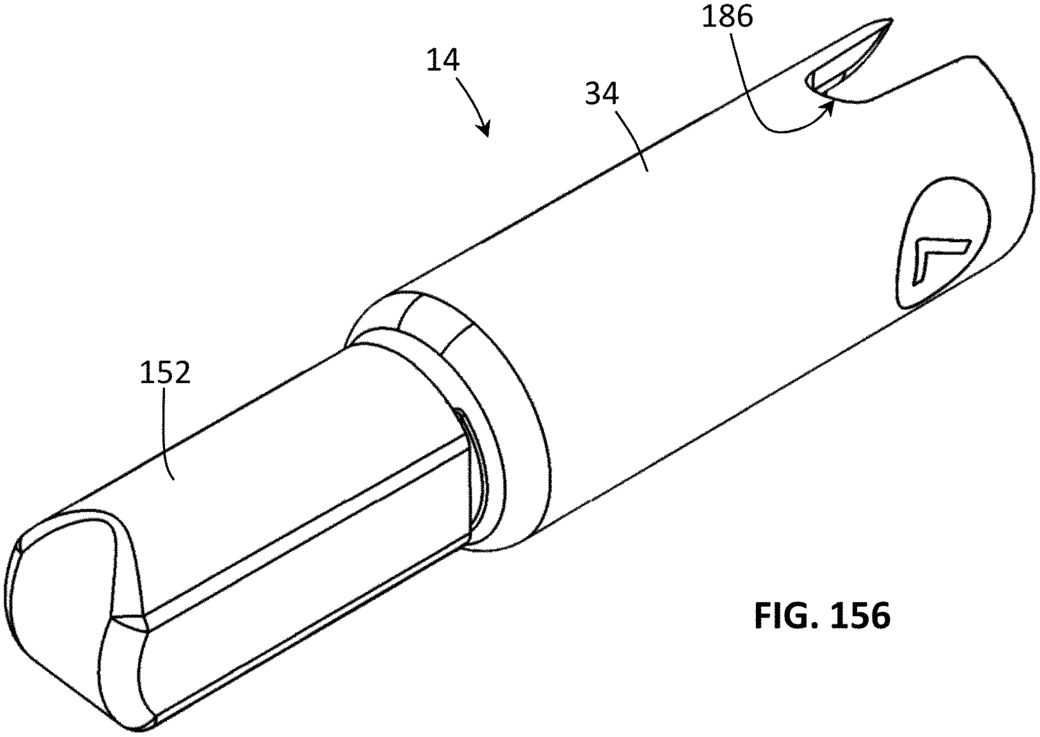
Figure 157:
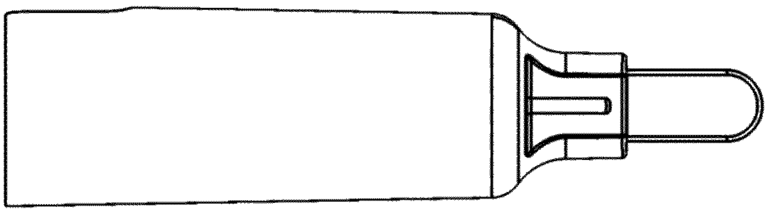
Figure 158:
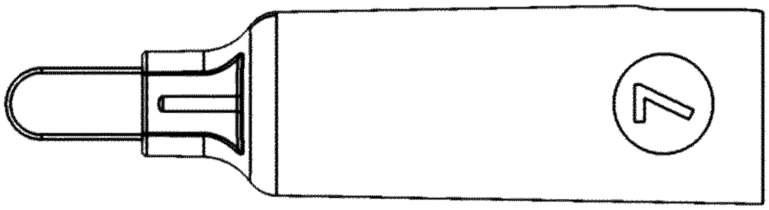
Figure 159:
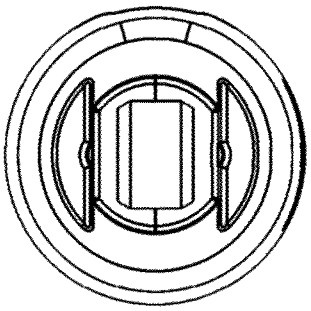
Figure 160:
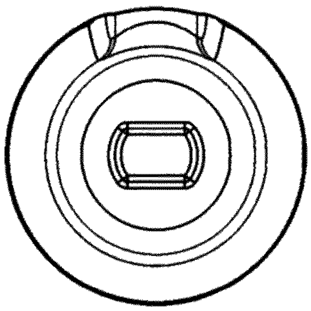
Figure 161:
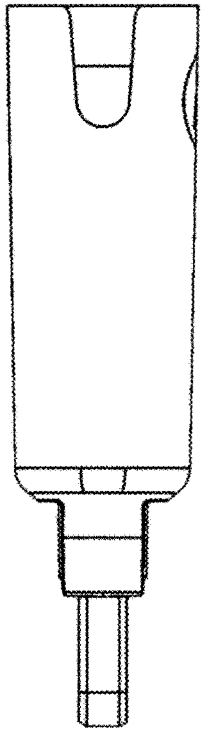
Figure 162:
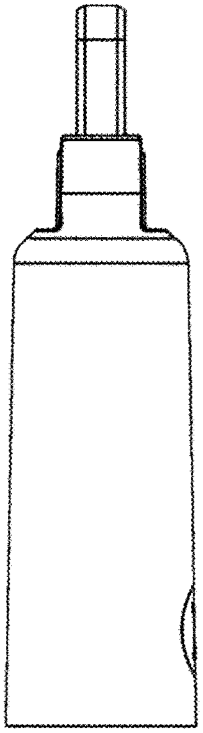
Figure 163:
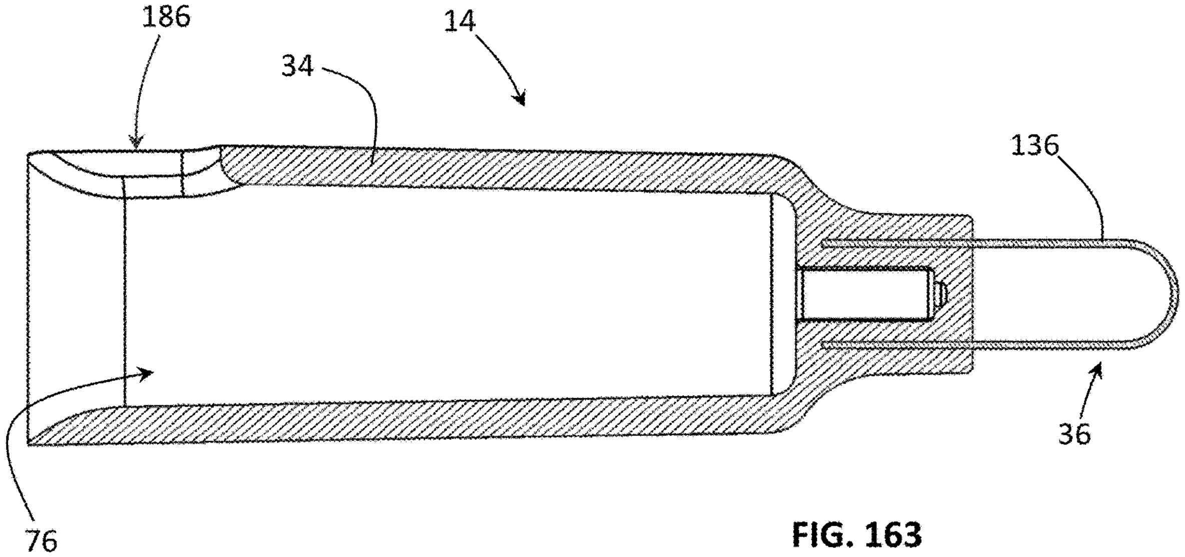
Figure 164:
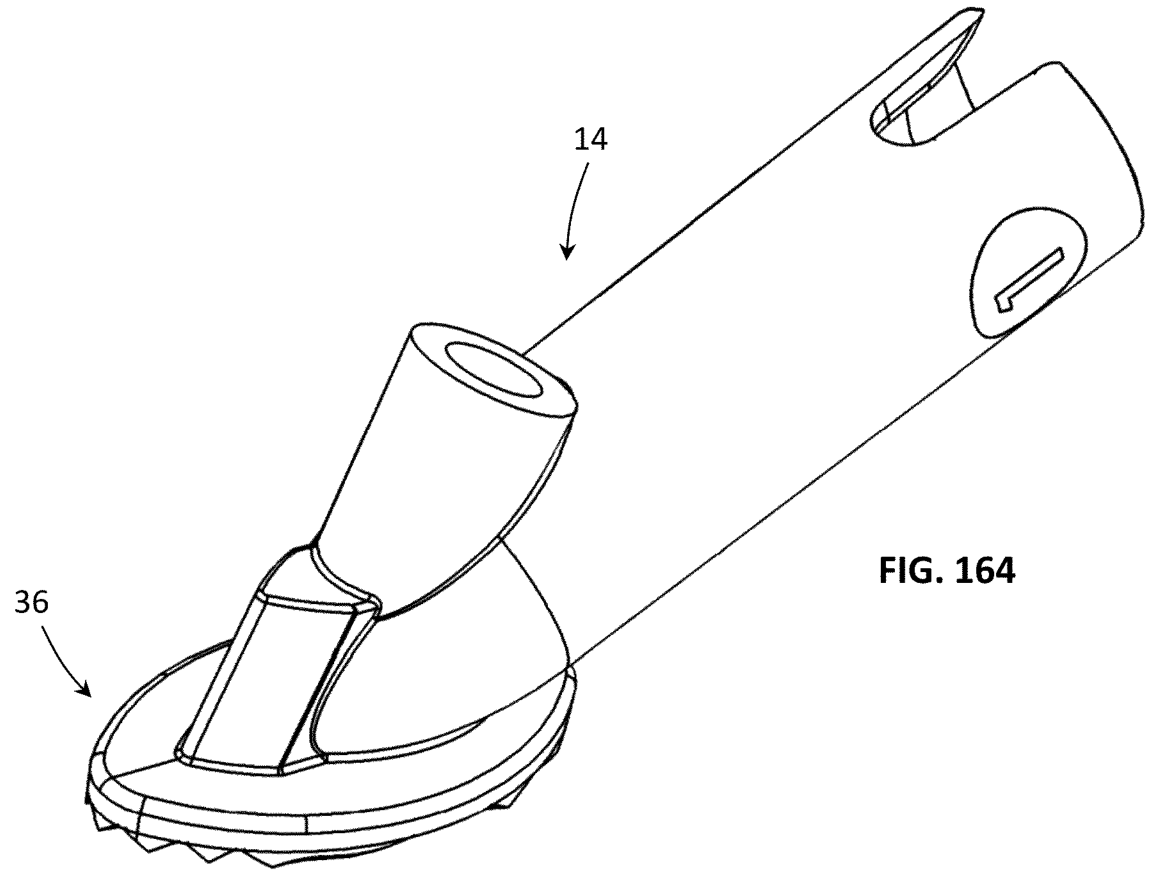
Figure 165:
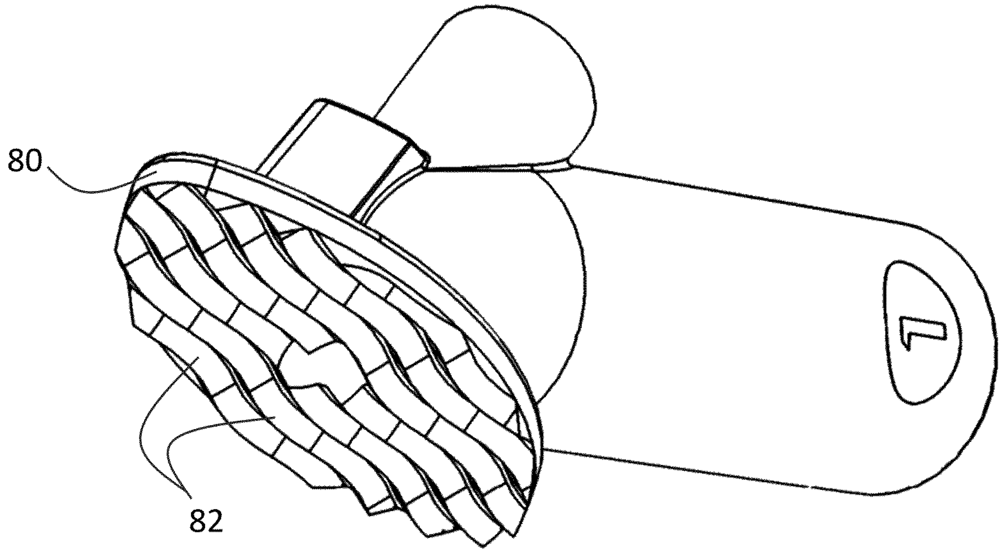
Figure 166:
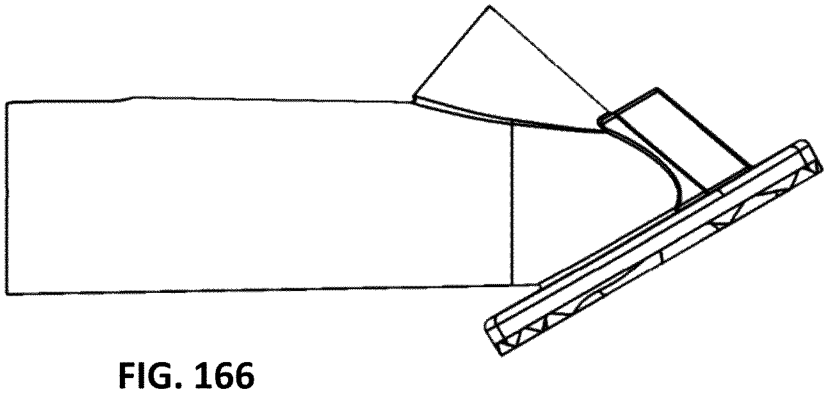
Figure 167:
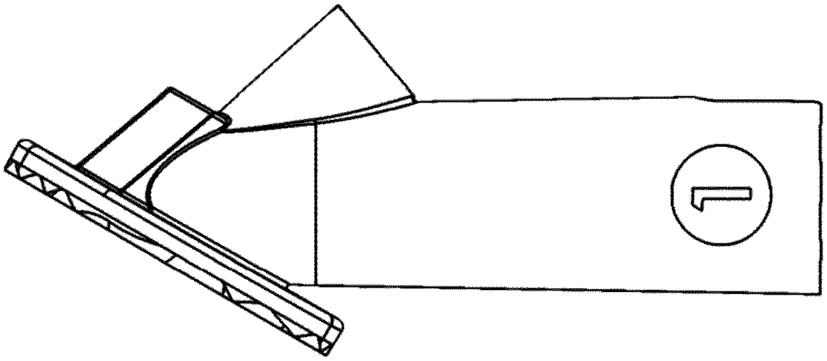
Figure 168:
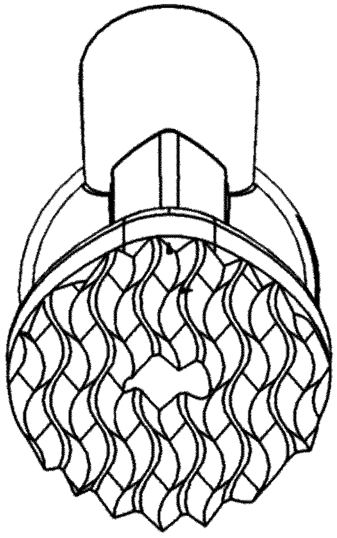
Figure 169:
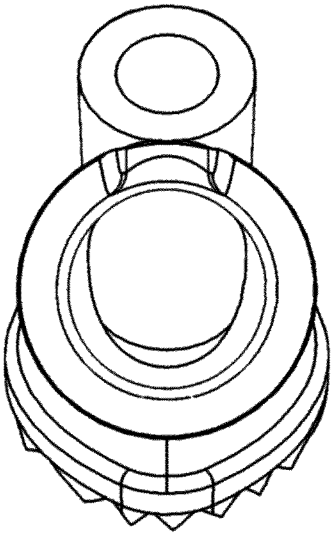
Figure 170:
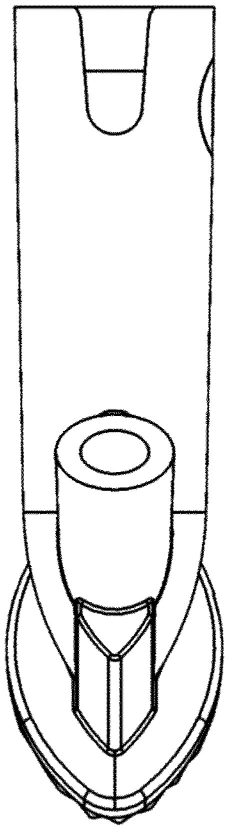
Figure 171:
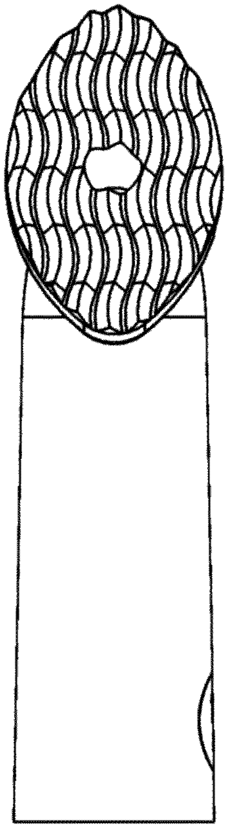
Figure 172:
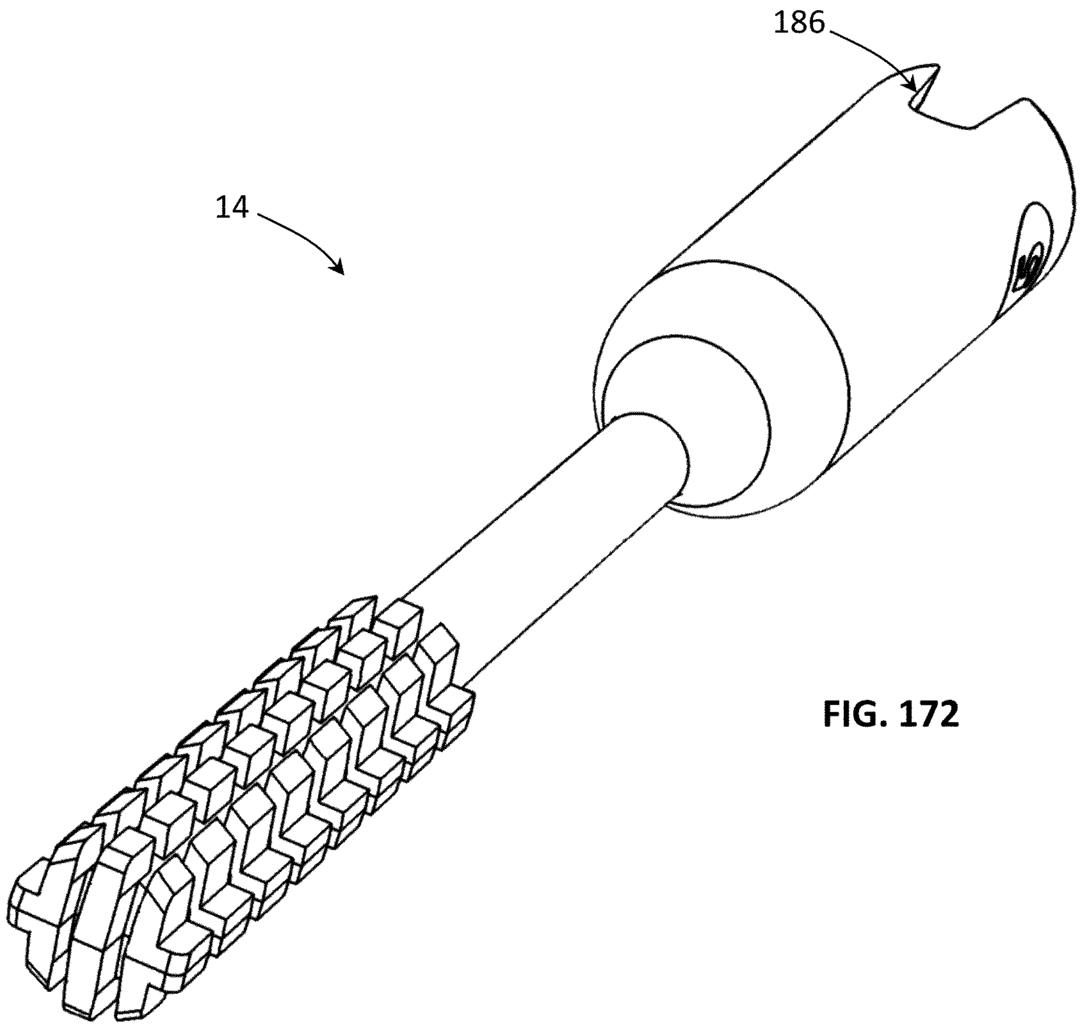
Figure 173:
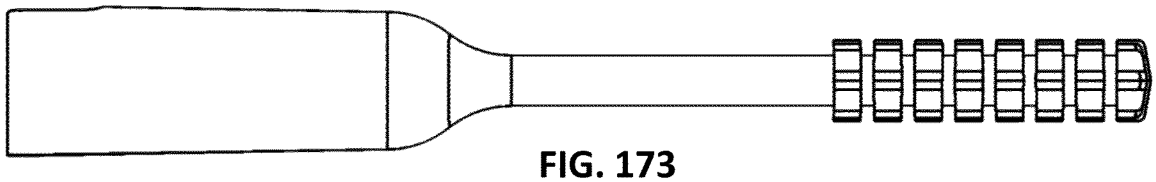
Figure 174:
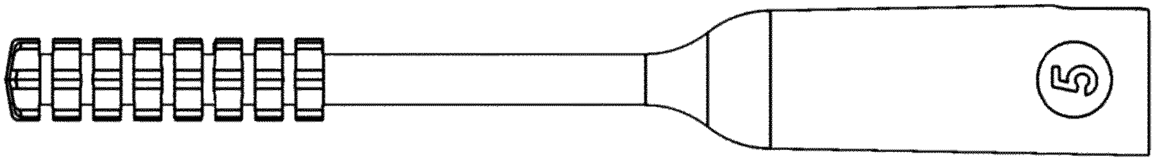
Figure 175:
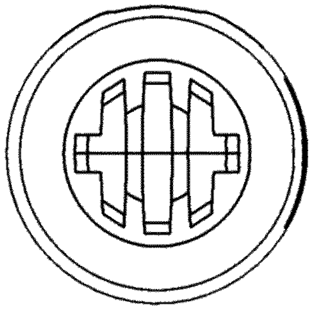
Figure 176:
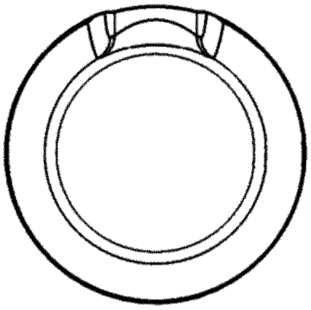
Figure 177:
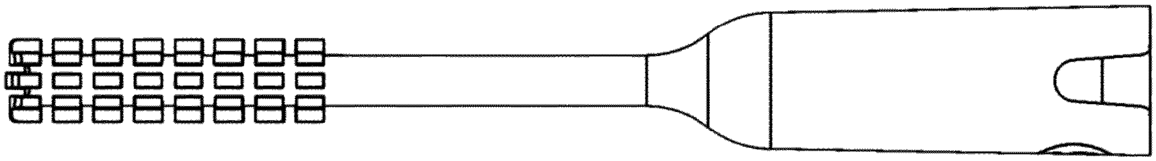
Figure 178:
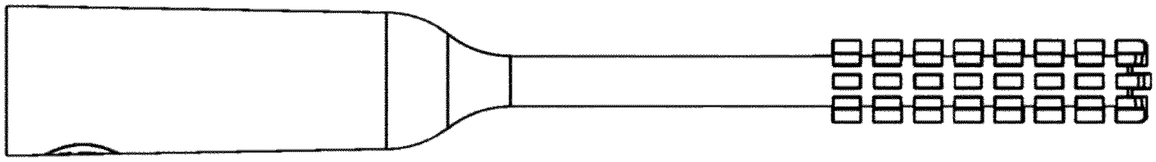
Figure 179A:
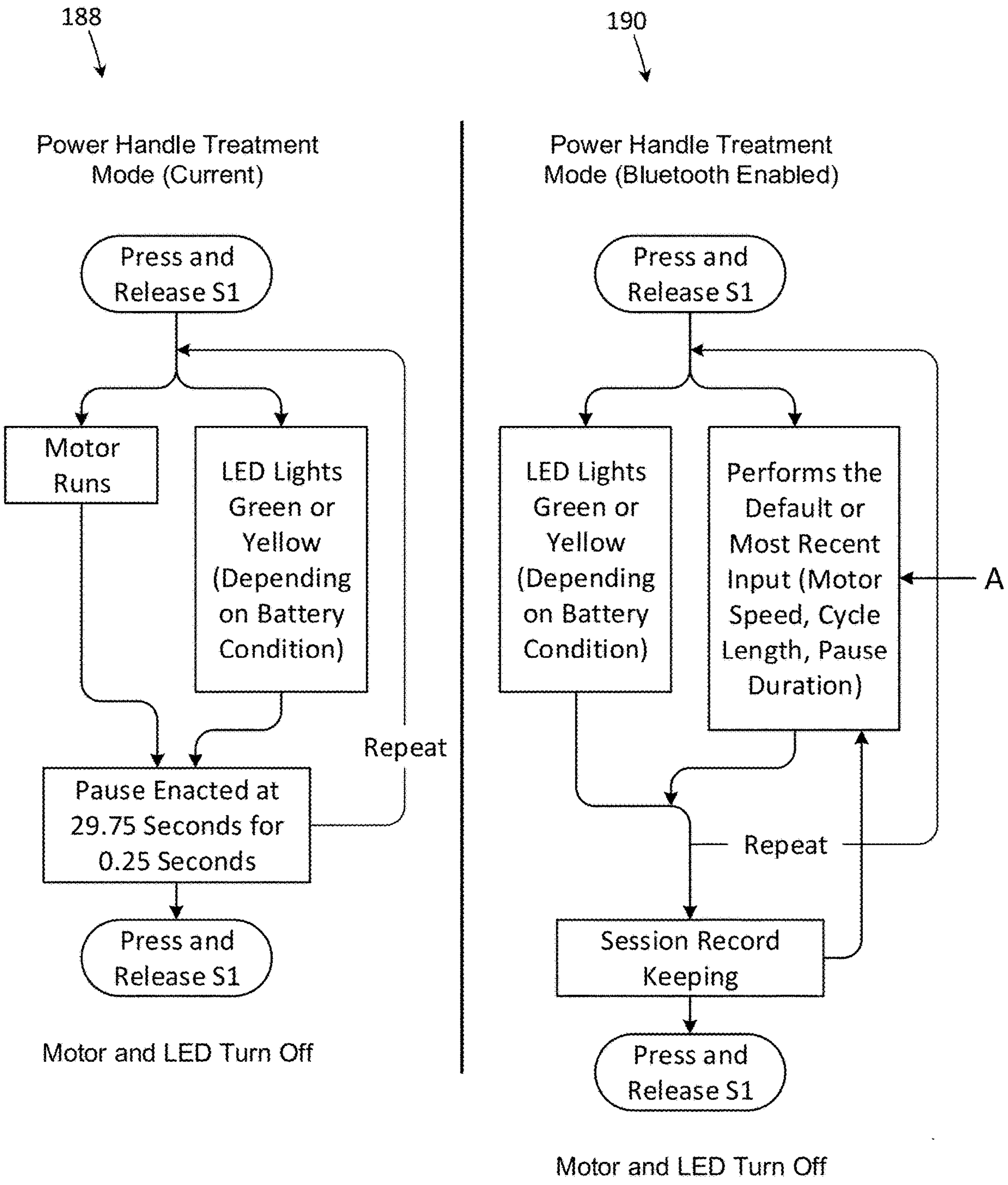
Figure 179B:
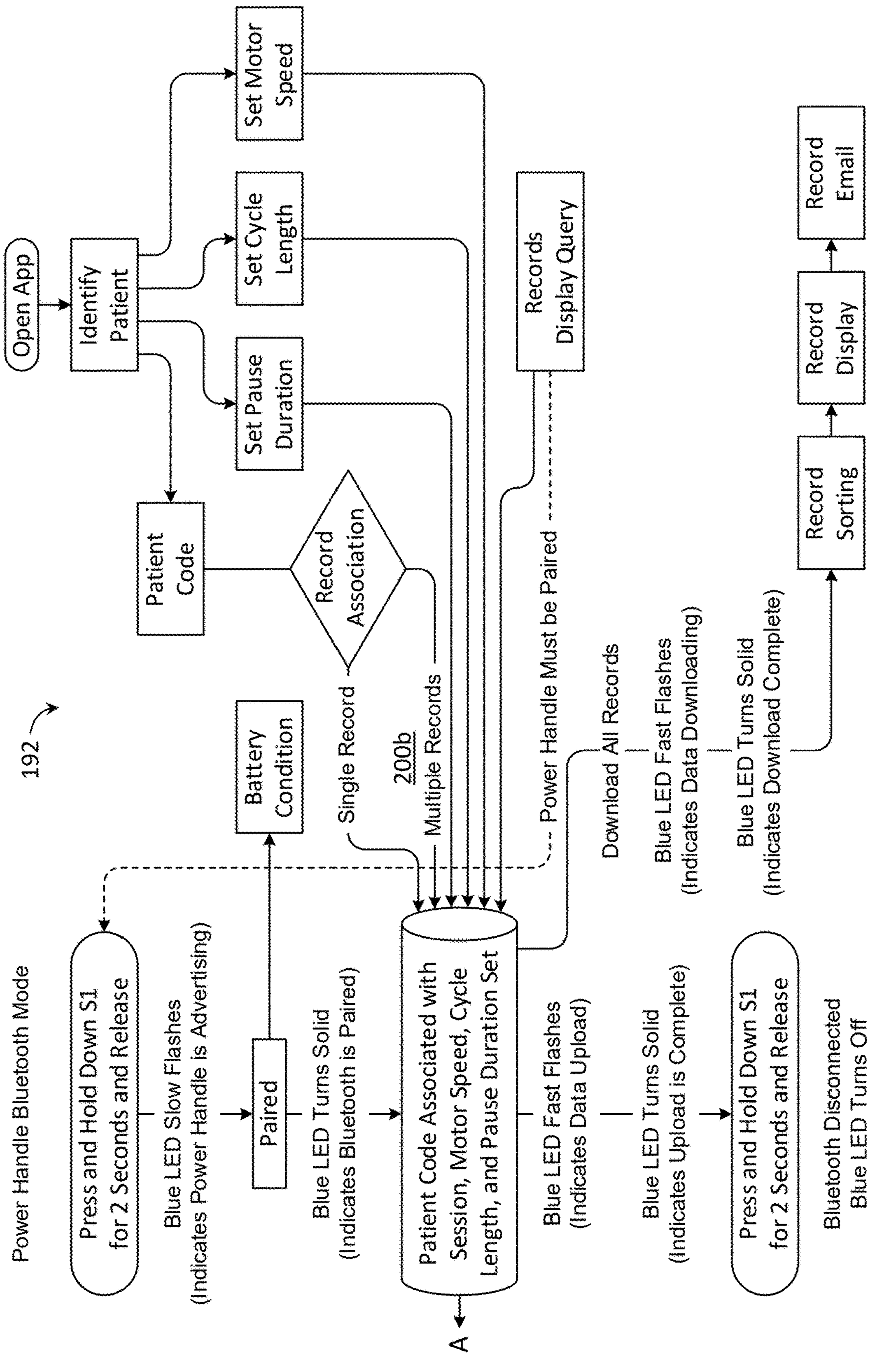
Figure 180:
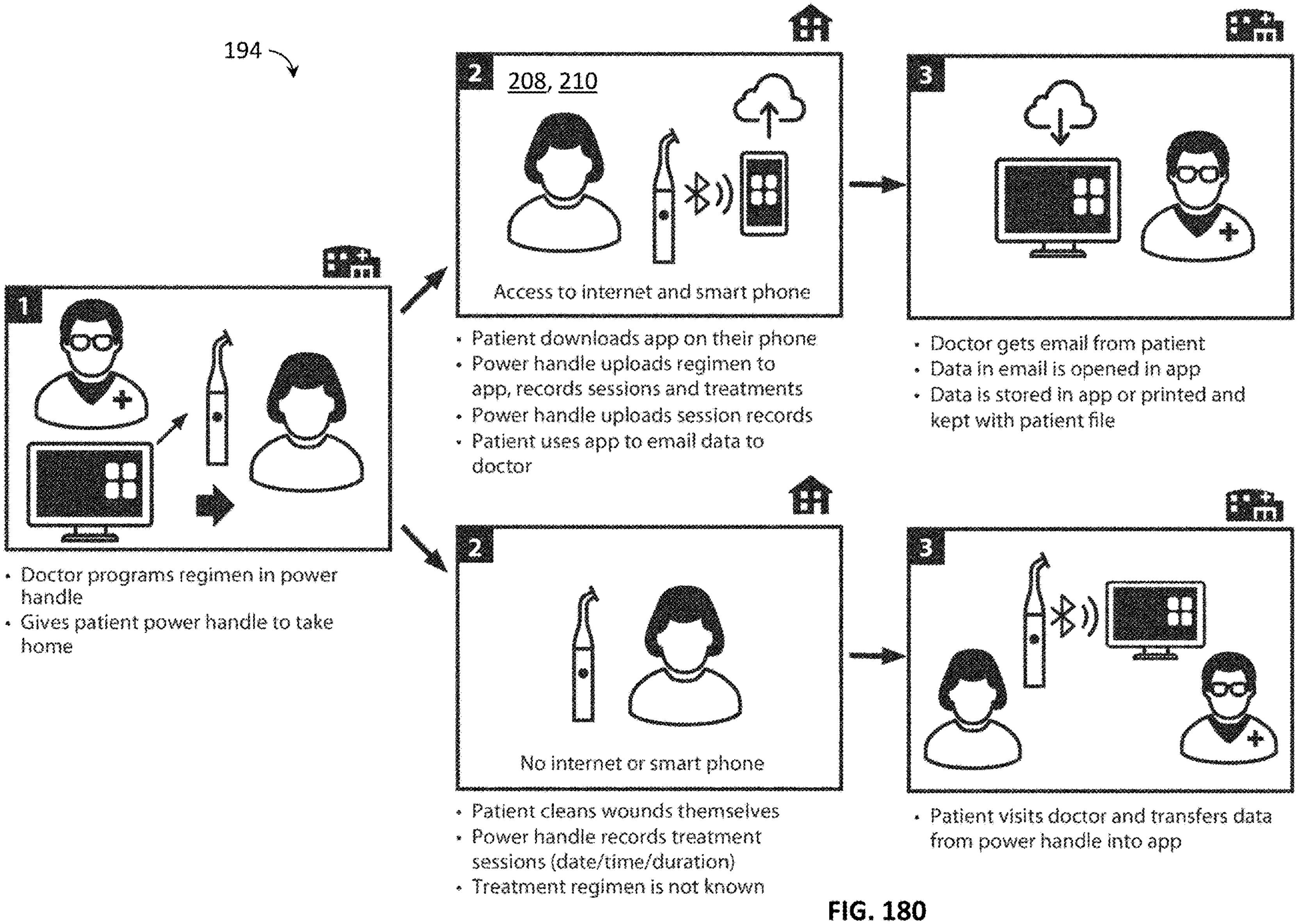
Figure 181:
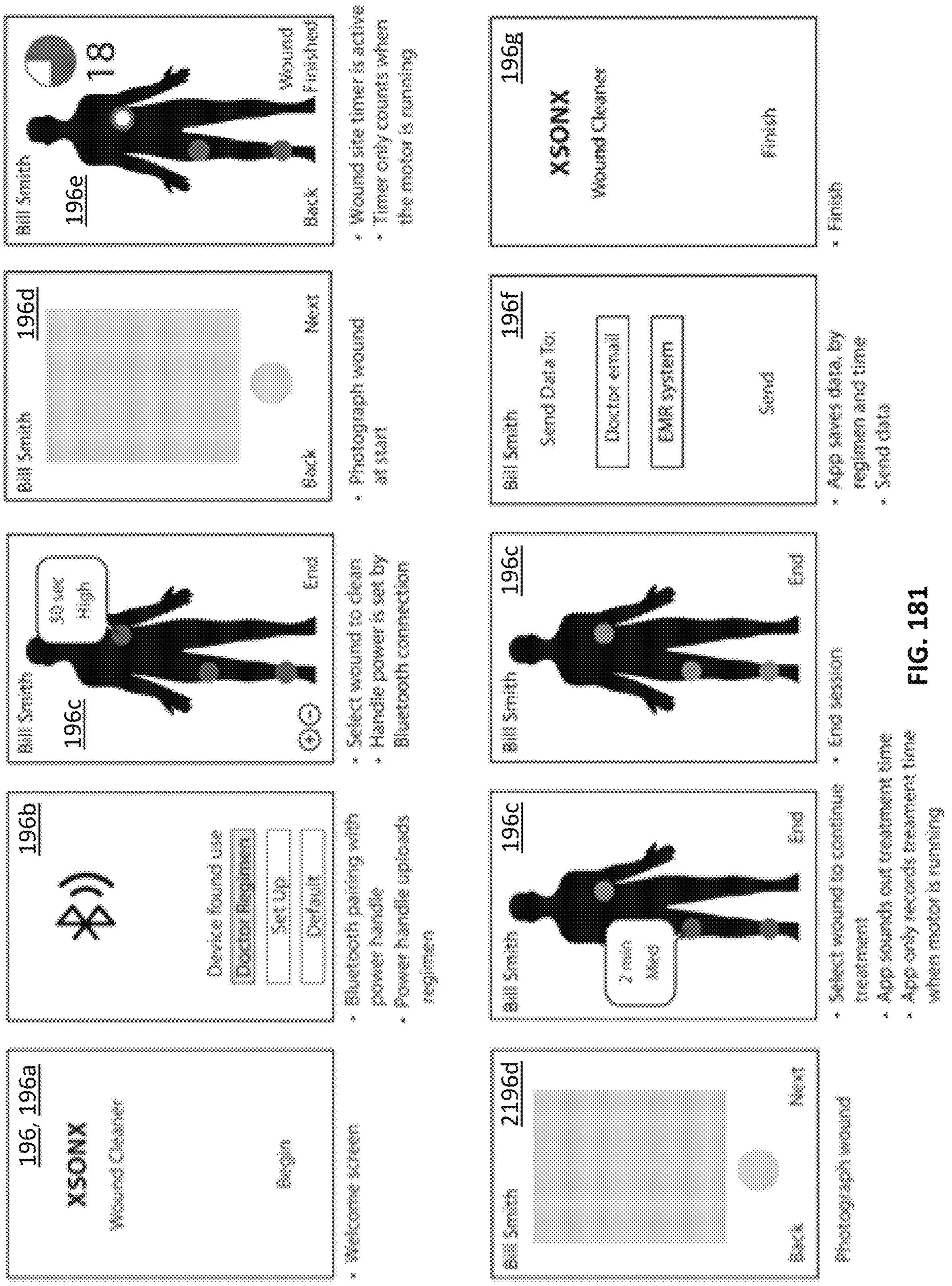
Figure 182:
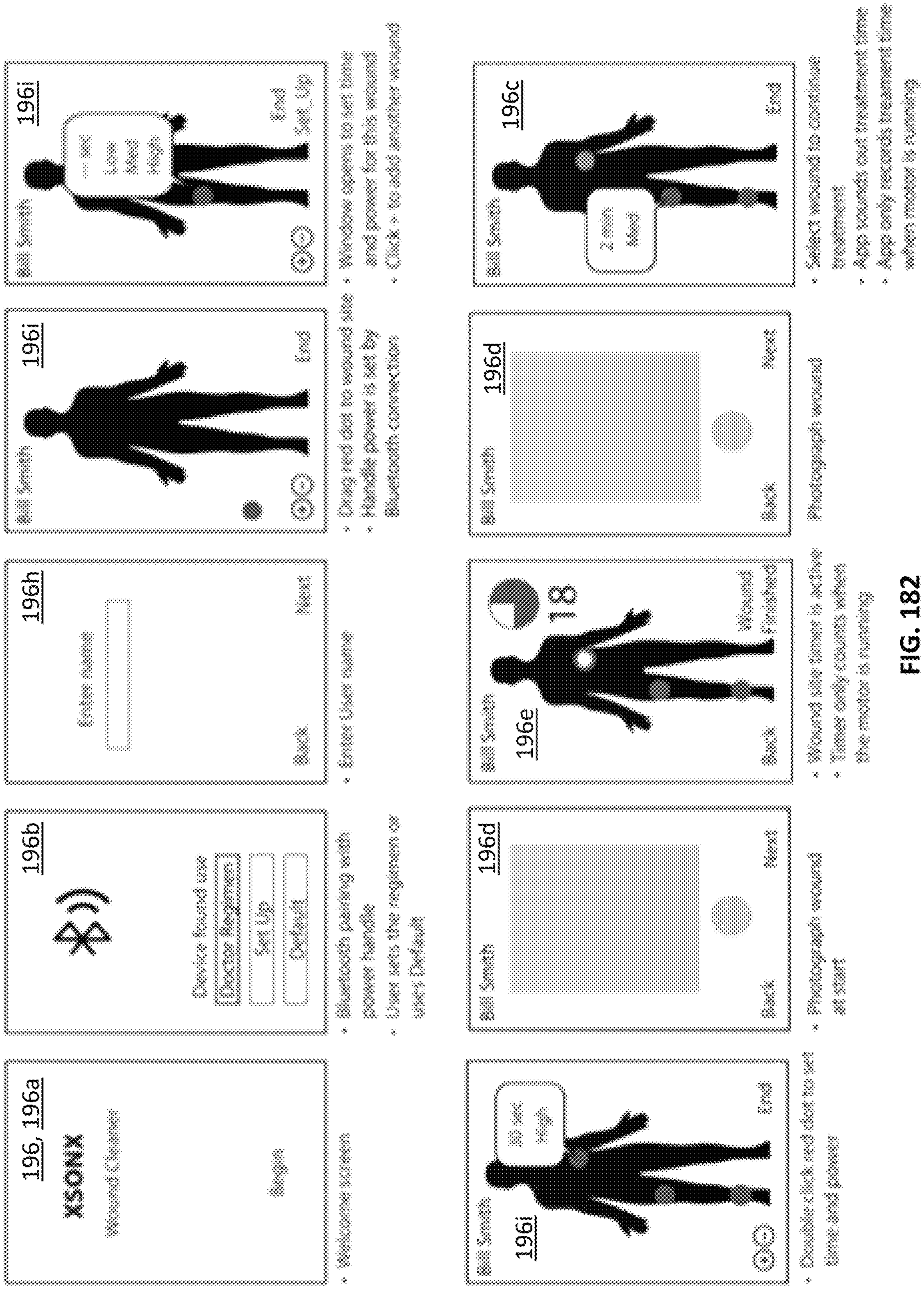
Figure 183:
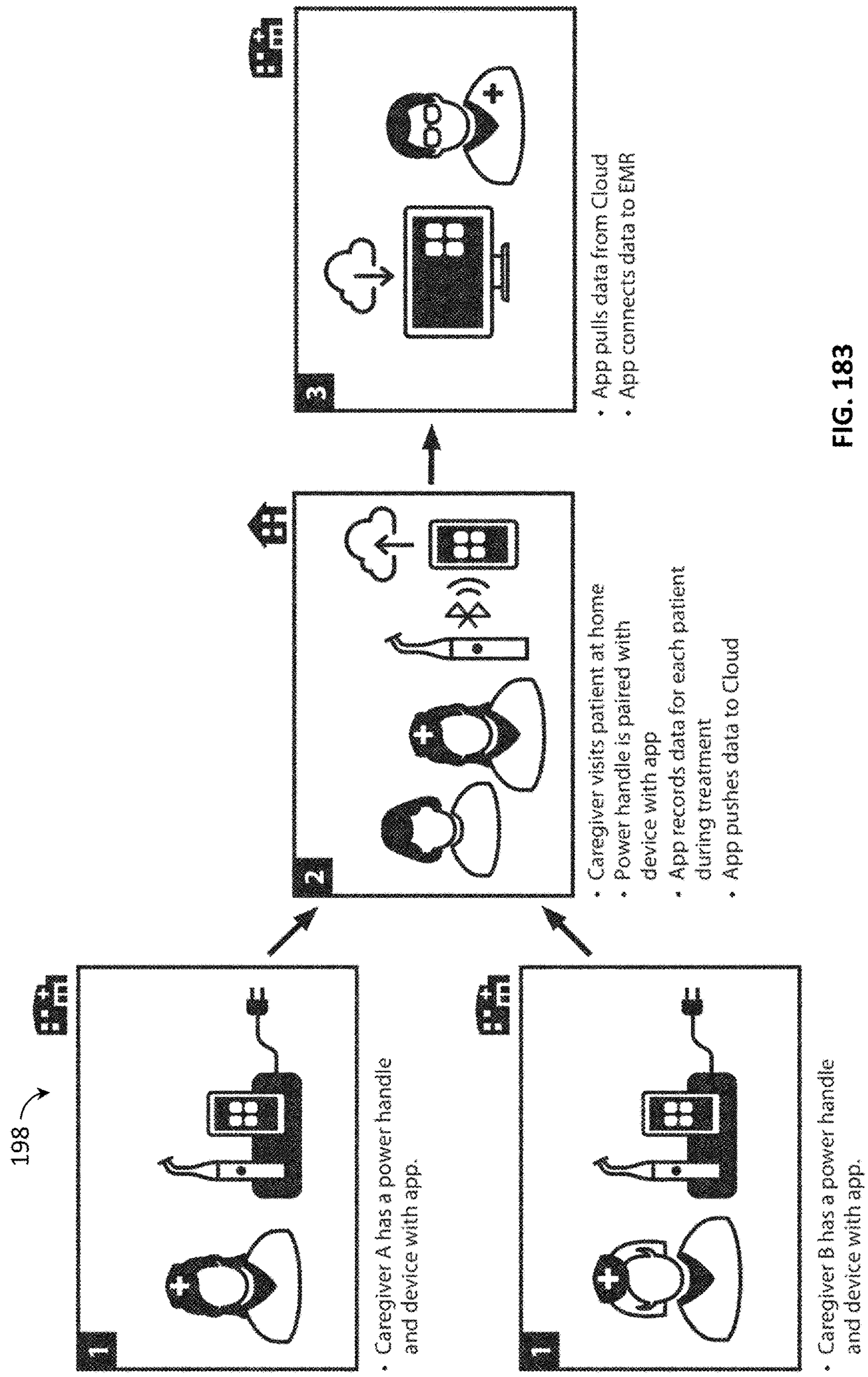
Figure 184:
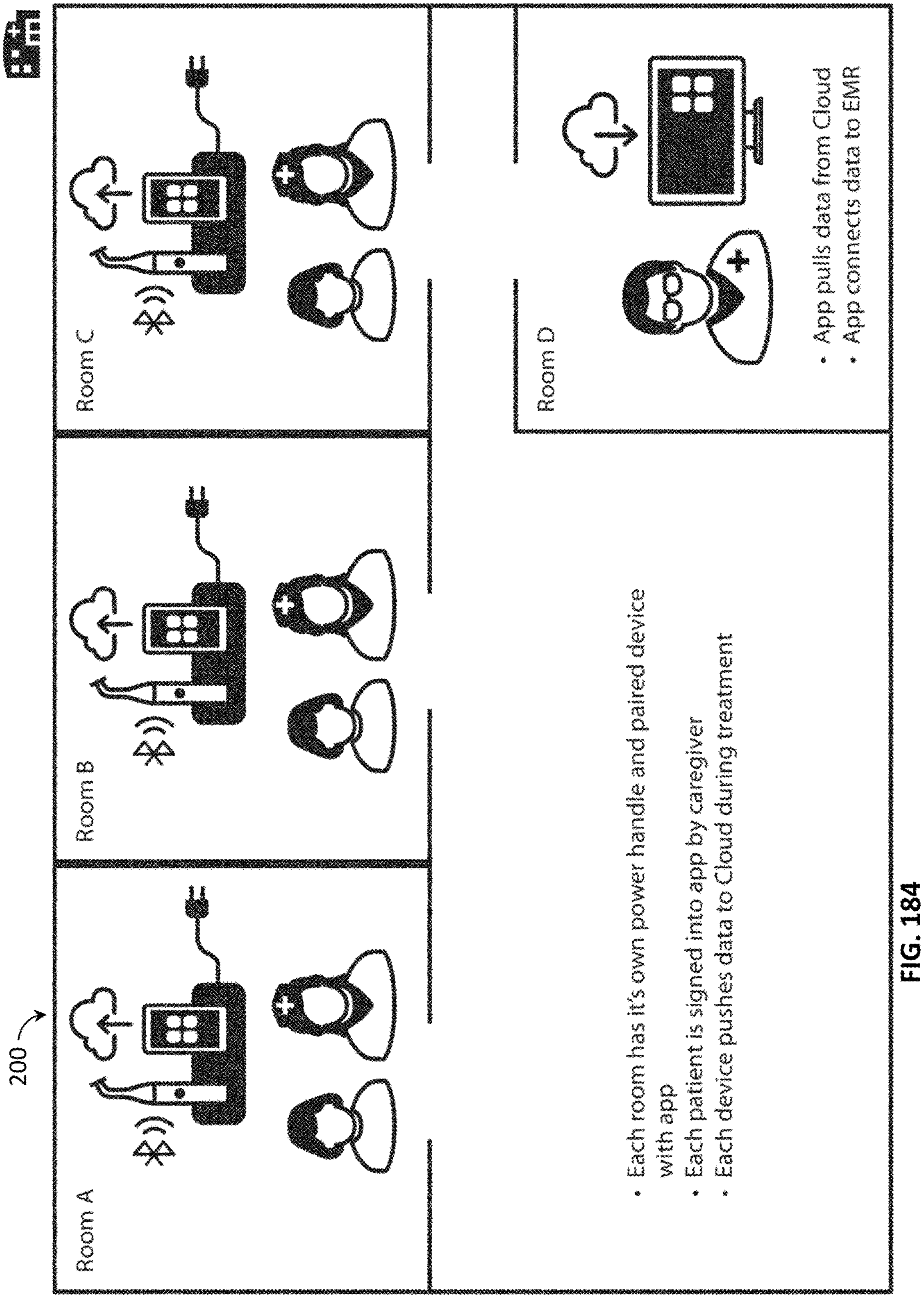
Figure 185:
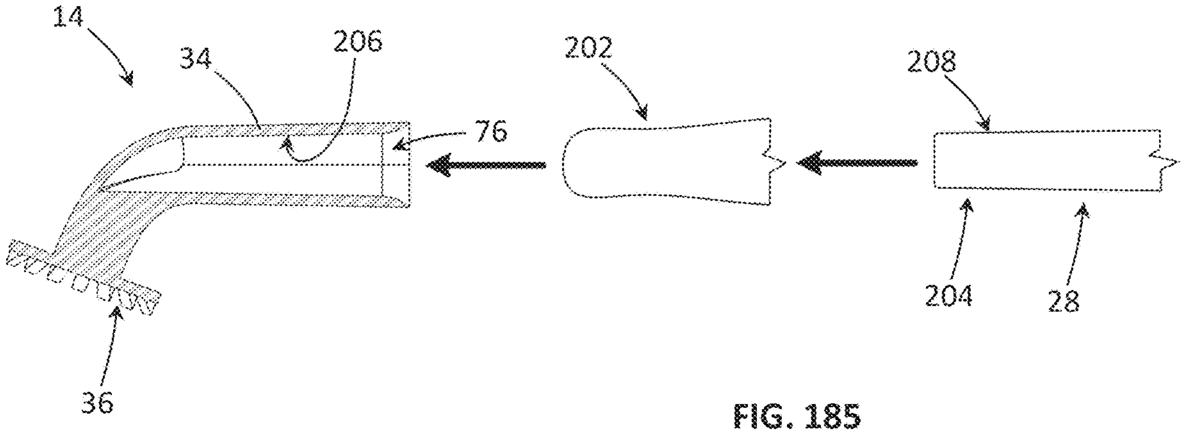
Figure 186:
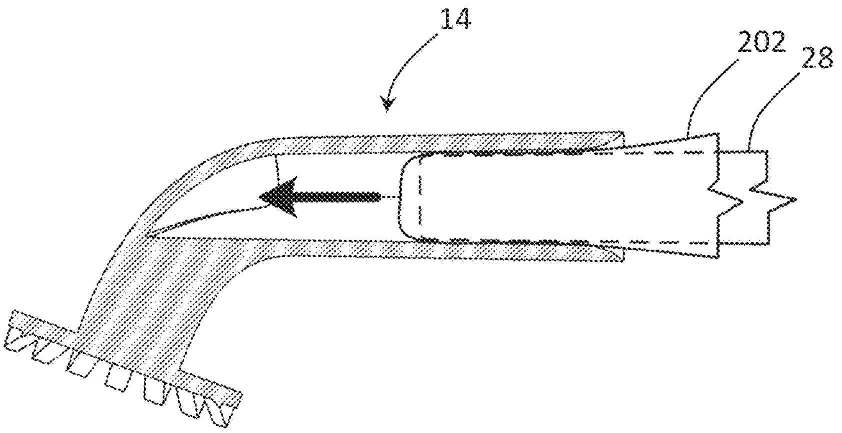

FIG. 131 is a perspective view of the head of FIG. 130 with a protective cover installed;

FIG. 132 is a first side view of the head of FIG. 130;

FIG. 133 is a second, opposite side view of the head of FIG. 130;

FIG. 134 is a top view of the head of FIG. 130;

FIG. 135 is a bottom view of the head of FIG. 130;

FIG. 136 is a first end view of the head of FIG. 130;

FIG. 137 is a second, opposite end view of the head of FIG. 130;

FIG. 138 is a side cross-sectional view of the head of FIG. 130;

FIG. 139 is a perspective view of another alternative embodiment of a head that may be applied to a wound-care device (e.g., the wound-care device of FIG. 105);

FIG. 140 is a side cross-sectional view of the head of FIG. 139;

FIG. 141 is a first side view of the head of FIG. 139;

FIG. 142 is a second, opposite side view of the head of FIG. 139;

FIG. 143 is a first end view of the head of FIG. 139;

FIG. 144 is a second, opposite end view of the head of FIG. 139;

FIG. 145 is a top view of the head of FIG. 139;

FIG. 146 is a bottom view of the head of FIG. 139;

FIG. 147 is a perspective view of another alternative embodiment of a head that may be applied to a wound-care device (e.g., the wound-care device of FIG. 105);

FIG. 148 is a side cross-sectional view of the head of FIG. 147;

FIG. 149 is a first side view of the head of FIG. 147;

FIG. 150 is a second, opposite side view of the head of FIG. 147;

FIG. 151 is a first end view of the head of FIG. 1479;

FIG. 152 is a second, opposite end view of the head of FIG. 147;

FIG. 153 is a top view of the head of FIG. 147;

FIG. 154 is a bottom view of the head of FIG. 147;

FIG. 155 is a perspective view of another alternative embodiment of a head that may be applied to a wound-care device (e.g., the wound-care device of FIG. 105);

FIG. 156 is another perspective view of the head of FIG. 155;

FIG. 157 is a first side view of the head of FIG. 155;

FIG. 158 is a second, opposite side view of the head of FIG. 155;

FIG. 159 is a first end view of the head of FIG. 155;

FIG. 160 is a second, opposite end view of the head of FIG. 155;

FIG. 161 is a top view of the head of FIG. 155;

FIG. 162 is a bottom view of the head of FIG. 155;

FIG. 163 is a perspective view of another alternative embodiment of a head that may be applied to a wound-care device (e.g., the wound-care device of FIG. 105);

FIG. 164 is a perspective view of the head of FIG. 163 with a protective cover applied;

FIG. 165 is a first side view of the head of FIG. 163;

FIG. 166 is a second, opposite side view of the head of FIG. 163;

FIG. 167 is a first end view of the head of FIG. 163;

FIG. 168 is a second, opposite end view of the head of FIG. 163;

FIG. 169 is a top view of the head of FIG. 163;

FIG. 170 is a bottom view of the head of FIG. 163;

FIG. 171 is a side cross-sectional view of the head of FIG. 163;

FIG. 172 is a perspective view of another alternative embodiment of a head that may be applied to a wound-care device (e.g., the wound-care device of FIG. 105);

FIG. 173 is a first side view of the head of FIG. 172;

FIG. 174 is a second, opposite side view of the head of FIG. 172;

FIG. 175 is a first end view of the head of FIG. 172;

FIG. 176 is a second, opposite end view of the head of FIG. 172;

FIG. 177 is a top view of the head of FIG. 172;

FIG. 178 is a bottom view of the head of FIG. 172;

FIGS. 179A and 179B are flow diagrams illustrating one embodiment of a method;

FIG. 180 is a flow diagram illustrating one embodiment of an at-home compliance method;

FIG. 181 is a diagram illustrating potential screen shots and corresponding flow for an application (e.g., a mobile app) where a medial professional (e.g., a doctor or nurse) has set up a treatment regimen;

FIG. 182 is a diagram illustrating potential screen shots and corresponding flow for an application (e.g., a mobile app) where a user (e.g., a patient or family member of a patient) sets up a treatment regimen;

FIG. 183 is a flow diagram illustrating one embodiment of a caregiver compliance method;

FIG. 184 is a flow diagram illustrating one embodiment of a clinical compliance method;

FIG. 185 is an exploded view of a head shown in cross-section, a portion of a sleeve, and a portion of a horn; and FIG. 186 is a partially assembled view of the head, sleeve, and horn of FIG. 185.

DETAILED DESCRIPTION OF SELECTED EMBODIMENTS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIGS. 1-4, devitalized tissue appearing in a wound bed may include fibroslough (primarily fibrinous tissue), leukoslough (primarily White Blood Cell (WBC) accumulation), necroslough (primarily necrotic tissue), and bioslough (primarily biofilm). Slough may be defined as devitalized tissue comprising primarily fibrin, but it may also include white blood cells, debris, and the like. The presence of slough may interrupt granulation and delay healing. It may also provide a favorable environment in which bacteria may grow and spread. There is also an infection continuum in wounds, proceeding from contaminated wound bed (bacteria on surface of wound but not replicating), colonized (bacteria are living on wound bed and replicating), early biofilm formation, mature biofilm formation, and local to systemic infection with biofilm seeding. Accordingly, to promote healing, a wound-care device 10 may facilitate the removal of devitalized tissue from a wound. This removal may be described as wound cleansing, desloughing, and/or debridement.

Depending on various factors, devitalized tissue in a wound bed may have different consistencies. For example, the consistency of devitalized tissue may be described as (1) mucinous (i.e., slimy and soft), (2) gelatinous, (3) stringy and/or clumpy, (4) fibrinous, and/or (5) leathery. Depending on the consistency of the devitalized tissue, different debridement tools and/or methods may be needed. For example, debridement suitable for devitalized tissue that is "leathery" may be too aggressive for devitalized tissue that is "mucinous." Accordingly, a wound-care device 10 may be adjustable or adaptable to provide proper cleansing and/or debridement across the range of consistency of devitalized tissue.

Bacterial biofilms can be found in 60-90% of chronic wounds and in approximately 6% of acute wounds. Biofilms usually contain multiple bacterial species. Biofilms can be found in multiple places, including within a wound bed (i.e., to a depth of about 60-70 microns below the surface of a wound), on a wound surface, in slough, in fluids on and around a wound bed, etc. and can migrate onto the wound dressings as well. Accordingly, a wound-care device 10 may be used to disrupt (e.g., disturb) bacteria growth, prevent the formation of bacterial biofilms, and/or treat bacterial biofilms.

Wound care may be complicated by the fact that a wide variety of people with a wide variety of medical experience and/or training are tasked with providing such care. For example, at home, patients with little to no medical experience or training are often tasked with providing their own wound care (e.g., tasked with fitting and/or changing their own would dressings). For patients with more serious wounds, wound care may be provided at their respective homes by ancillary healthcare staff having various levels of wound-care training. Some ancillary healthcare staff may have associate nursing degrees. Others have bachelor's degrees in nursing. Still others may be specialized wound, ostomy, and continence nurses (WOCN). However, regardless of such educational background, ancillary healthcare staff will have different comfort levels and skill sets with respect to cleansing wounds and conducting even basic wound cleansing and/or debridement.

In institutional, long-term care settings such as nursing homes and long-term acute care (LTAC) hospitals, there may be wound-care teams with more advanced training and an enhanced skill set due to their repeated and regular treating of complicated wounds. In the offices of physicians and surgeons, wounds often need cleansing or mild surgical debridement. Such treatment is often performed in an operating room. However, such use of an operating room is often unnecessary and increases the cost of treatment and may increase morbidity depending on choice of anesthesia.

Accordingly, to address the wide variety of people tasked with providing wound care, a wound-care device 10 may be easy to use. Moreover, it may be configured so as to limit the potential for misuse or harmful use. Accordingly, both an inexperienced patient and a highly trained medical professional may both use a wound-care device 10 to beneficial effect.

In selected embodiments, a wound-care device 10 may comprise a main body 12 or handle portion and a head 14. In other embodiments, a wound-care device 10 may comprise a main body 12, a head 14, and a fluid system 16. A head 14 may removably connect to a main body 12. In operation, a head 14 may apply motion (e.g., vibration, oscillation, reciprocation, or the like) generated by a main body 12 to a wound surface. Accordingly, a main body 12 may be responsible for generating a desired motion and a head 14 may be responsible to conduct that motion from the main body 12 to a wound surface.

In certain embodiments, a main body 12 may include a motion generator 18, one or more batteries 20, a controller 22, a housing 24, one or more other structures 26 or components, or the like or a combination or sub-combination thereof. A motion generator 18 may generate vibration, oscillation, reciprocation, or the like at a desired frequency. The one or more other structures 26 (e.g., a physical linkage, shaft, or the like), a housing 24, or the like may conduct the vibration, oscillation, or reciprocation to a head 14.

In selected embodiments, a motion generator 18 may vibrate, oscillate, reciprocate, or the like at a relatively low sonic frequency in a range from about 100 Hz to about 1000 Hz. Alternatively, or in addition thereto, a motion generator 18 may vibrate, oscillate, reciprocate, or the like at a relatively high amplitude (e.g., an amplitude in the range from about 1 mm to about 10 mm and, more preferably, about 3 mm to about 8 mm). That is, once a head 14 is applied to a main body 12, the vibration, oscillation, reciprocation, or the like of a motion generator 18 may produce a side-to-side sweeping motion at a distal end of the head 14 that is about 1 mm to about 10 mm (and, more preferably, about 3 mm to about 8 mm) from one extreme to the other. In other embodiments, the amplitude and/or motion may be different, but may still be in a relatively low sonic frequency range. Thus, a wound-care device 10 may operate at a frequency that is much lower than any ultrasonic debridement device and benefit from the higher amplitude that may be obtained at that lower frequency.

In selected embodiments, a motion generator 18 may comprise an electromagnet with a polarity that is alternated at a desired frequency in order to create a desired vibration, oscillation, or reciprocation (e.g., a desired vibration, oscillation, or reciprocation in a linkage that extends to engage a head 14). In other embodiments, a motion generator 18 may comprise an electric motor turning a shaft having an eccentric weight secured thereto to generate a vibration, oscillation, or reciprocation effect.

For example, a motion generator 18 may comprise an electric motor having a rated speed of about 9,000 to about 36,000 revolutions per minute (and preferably about 18,000 to about 22,000 revolutions per minute) when a rated load (e.g., an eccentric mass of about 0.5 to about 1.0 grams and preferably about 0.75 grams) is applied to the shaft thereof. That speed may translate to a vibration, oscillation, reciprocation, or the like in the sonic range of about 150 Hz to about 600 Hz, where each cycle may comprise two strokes (e.g., one stroke or deflection to the left and a return stroke or deflection to the right) across a wound bed. Thus, a motion generator 18 operating at about 150 Hz may produce about 300 vibration strokes per second, while a motion generator 18 operating at about 600 Hz may produce about 1,200 vibration strokes per second.

A motion generator 18 may generate vibration, oscillation, and/or reciprocation in a linkage or other structure that extends to engage a head 14. For example, in selected embodiments, one end of a main body 12 may comprise or form a horn 28 within which a motion generator 18 may be positioned. When turned "on," a motion generator 18 may cause a horn 28 to vibrate, oscillate, and/or reciprocate at a desired frequency. Accordingly, when a horn 28 is inserted within or otherwise connected to a correspondingly shaped head 14, the horn 28 may communicate that vibration, oscillation, and/or reciprocation to the head 14.

In selected embodiments, the structure configuration of a horn 28, a head 14, or a horn 28 and head 14 combination may define the type or shape of motion generated by a motion generator 18. For example, by selecting where the greatest mass is located, which axis of bending or deflection is preferred (i.e., is less resistant to bending or deflection), or the like or a combination thereof, the motion of a head 14 may be defined as being more circular, rocking back and forth, translating side to side, or the like in order to provide a desired effect, action, or operation on a wound bed.

A battery 20 may provide the electrical power required by a motion generator 18. In selected embodiments, a battery 20 may be rechargeable. For example, a battery 20 (e.g., a lithium-ion battery) may include or be connected to a receiving or secondary coil to enable or support wireless charging when a wound-care device 10 corresponding thereto is placed on or in a charging station. Alternatively, or in addition thereto, a device may be at least partially powered and/or charged by one or more supercapacitors.

A controller 22 may control operation of a main body 12. In selected embodiments, a controller 22 may comprise a switch 30 for turning a motion generator 18 on and off. Alternatively, or in addition thereto, a controller 22 may comprise a printed circuit board (PCB) 32, one or more integrated circuits, one or more processors (e.g., an application-specific integrated circuit (ASIC), a programmable logic controller (PLC), or the like), memory, or the like or a combination or sub-combination thereof in order to control a motion generator 18. Accordingly, a controller 22 may automatically control certain functions of a wound-care device 10.

For example, a controller 22 may turn off a motion generator 18 if a battery is low on charge, if a particular time interval (e.g., 2 to 3 minutes) has passed since the wound-care device 10 was turned on, or the like. A controller 22 may control the speed and/or power of a wound-care device 10 through one or more switches 30, buttons, or the like that may be operated by a user. In selected embodiments, a controller 22 may regulate or condition a voltage (e.g. increase a voltage from 3.0 V to 3.7 V or some other desired voltage) of electrical current passing from a battery 20 or other power source to a motion generator 18 as desired or necessary.

In selected embodiments, a controller 22, may pulse, momentarily pause vibration, beep, flash a light, or the like at predetermined, regular intervals (e.g., every 30 seconds) so that the user may more easily monitor and control the time spent cleansing or debriding a wound. Accordingly, a physician may instruct a patient or home-healthcare nurse to use a wound-care device 10 for 30 seconds to cleanse a small wound, 90 seconds for a large wound, or the like. The patient or nurse may then watch for the appropriate number of pulses or beeps in order to meet the prescribed treatment time.

A housing 24 may contain various other components of a main body 12. For example, a housing 24 may contain and provide structure for mounting or anchoring a motion generator 18, battery 20, controller 22, and the like. In selected embodiments, a housing 24 may form a handle. Accordingly, when a user uses a wound-care device 10, the user may grasp and hold the housing 24.

In certain embodiments, a head 14 may include a frame 34, a contact surface 36, one or more other components 38 or structures, or the like or a combination or sub-combination thereof. A frame 34 may extend from a main body 12 to support a contact surface 36. For example, a frame 34 may engage a physical linkage, horn 28, or the like that is selectively vibrated, oscillated, and/or reciprocated by a motion generator 18. Accordingly, a frame 34 may conduct vibrations, oscillations, and/or reciprocations that originate with a motion generator 18 to a contact surface 36.

A contact surface 36 may be configured to contact a wound surface. In selected embodiments, a head 14 may be considered as having a front side 40 and a back side 42. In such embodiments, a contact surface 36 may be or correspond to a front side 40 of a head 14. Accordingly, a contact surface 36 may be configured to provide a desired cleansing, desloughing, debridement, or the like.

In certain embodiments, a contact surface 36 may be selectively separable from a frame 34 corresponding thereto. Accordingly, a user may obtain or control a cleansing, desloughing, or debriding effect by selecting and installing a contact surface 36 designed to provide the cleansing, desloughing, or debriding effect. Alternatively, a contact surface 36 may be integrally or substantially permanently connected to a frame 34. Accordingly, in certain embodiments, a user may obtain or control a cleansing, desloughing, or debriding effect by selecting and installing a head 14 having a contact surface 36 designed to provide the cleansing, desloughing, or debriding effect.

In selected embodiments, a contact surface 36 may be configured for single use. For example, a contact surface 36 (or a head 14 comprising a frame 34 and a contact surface 36) may be provided to a user in a clean (e.g., sterile) condition and within appropriate (e.g., sterile) packaging. After being used on a wound, a contact surface 36 will no longer be clean and may have significant bacterial contamination. Accordingly, the contact surface 36 (or the head 14 comprising the frame 34 and the contact surface 36) may be discarded and a contact surface 36 that is new (or a head 14 that is new) may be used for the next cleansing, desloughing, or debridement.

A fluid system 16 may facilitate wound cleansing, desloughing, and/or debridement. Fluid provided or delivered by a fluid system 16 may tend to flush loose material and particles out of a wound bed. For example, fluid delivered to a central location on a contact surface 36 may irrigate outward (e.g., radially outward) and across the contact surface 36 (e.g., within various channels formed in the contact surface 36) to aid in removing, dislodging, and flushing bacteria, toxins, and cellular debris and preventing clogging of the contact surface 36. Alternatively, or in addition thereto, fluid may tend to soften materials that are being removed so as to aid in (e.g., speed) their removal.

In selected embodiments, a fluid system 16 may include a fluid reservoir 44, a compression element 46, one or more other components 48 or structures, or the like or a combination or sub-combination thereof. A fluid reservoir 44 may contain a fluid (e.g., saline, an antibiotic or antiseptic in liquid form, a gel, a paste, or the like). A fluid reservoir 44 may be deformable. Deformation of a fluid reservoir 44 may tend to expel fluid therefrom. Accordingly, manual deformation (e.g., squeezing, flattening, etc.) of a fluid reservoir 44 may provide the motive force for and/or control a rate of expelling fluid from a fluid reservoir 44.

In certain embodiments, a fluid reservoir 44 may be directly manually compressed by the hand or fingers of a user. In other embodiments, a compression element 46 may be included to assist in compressing a fluid reservoir 44. A compression element 46 may be a structure or combination of structures that facilitates deformation (e.g., compression) of a fluid reservoir 44. For example, a compression element 46 may be a structure that holds a fluid reservoir 44 in place along a housing 24 (e.g., along an underside of a housing 24) so that a user can hold the wound-care device 10 and squeeze the fluid reservoir 44 at the same time (e.g., with the same hand). Alternatively, or in addition thereto, a compression element 46 may comprise a lever that operates in conjunction with a housing 24 so that a fluid reservoir 44 may be squeezed therebetween. Accordingly, by pulling the lever, the same hand with which a user holds a main body 12 may be used to expel fluid from the fluid reservoir 44.

In selected embodiments, a wound-care device 10 may include a conduit 50. A conduit 50 may extend to place a fluid reservoir 44 in fluid communication with a head 14. Accordingly, manual deformation of a fluid reservoir 44 may urge fluid out of the fluid reservoir 44 and into a conduit 50. The fluid may then travel through the conduit 50 until it reaches the head 14 where it may be expelled proximate a contact surface 36. In other embodiments, a conduit 50 for fluid (or selected portions of a conduit 50 for fluid) may be integral to a head 14.

A conduit 50 may include a check valve 52, a disconnect 54, one or more other components 56 or structures, or the like or a combination or sub-combination thereof. A check valve 52 may permit fluid to move from a fluid reservoir 44 toward a head 14 and prevent fluid from moving from the head 14 back toward a fluid reservoir 44. This may prevent contaminated fluid from being sucked into a wound-care device 10. In certain embodiments, a check valve 52 may be part of a fluid reservoir 44 rather than part of a conduit 50. In other embodiments, a check valve 52 may be part of a head 14 rather than part of a conduit 50. However, wherever a check valve 52 may be located, it may enforce the same one-way flow of fluid.

One or more disconnects 54 may enable a conduit 50 to be selectively connected and/or disconnected to a fluid reservoir 44, a head 14, or the like. Alternatively, a conduit 50 may simply have one or more ends that may be inserted within or over a properly sized aperture or port of a head 14 or fluid reservoir 44 in order to enable fluid to flow across the resulting interface. In either case, a conduit 50 may selectively connect to and disconnect from a head 14, a fluid reservoir 44, or both a head 14 and fluid reservoir 44. Accordingly, heads 14, fluid reservoirs 44, and conduits 50 may be installed, removed, and/or discarded as needed.

In selected embodiments, a fluid system 16 and conduit 50 may be omitted from a wound-care device 10. In such embodiments, cleansing, desloughing, and/or debridement of a wound bed may be conducted in a "dry" manner without the addition of any fluid. Alternatively, fluid may be applied in a separate process. For example, a liquid, gel, paste, or the like may be applied to a wound bed in a first process that precedes and is separate from using a wound-care device 10 to clean, deslough, or debride the wound bed.

Figure 1:
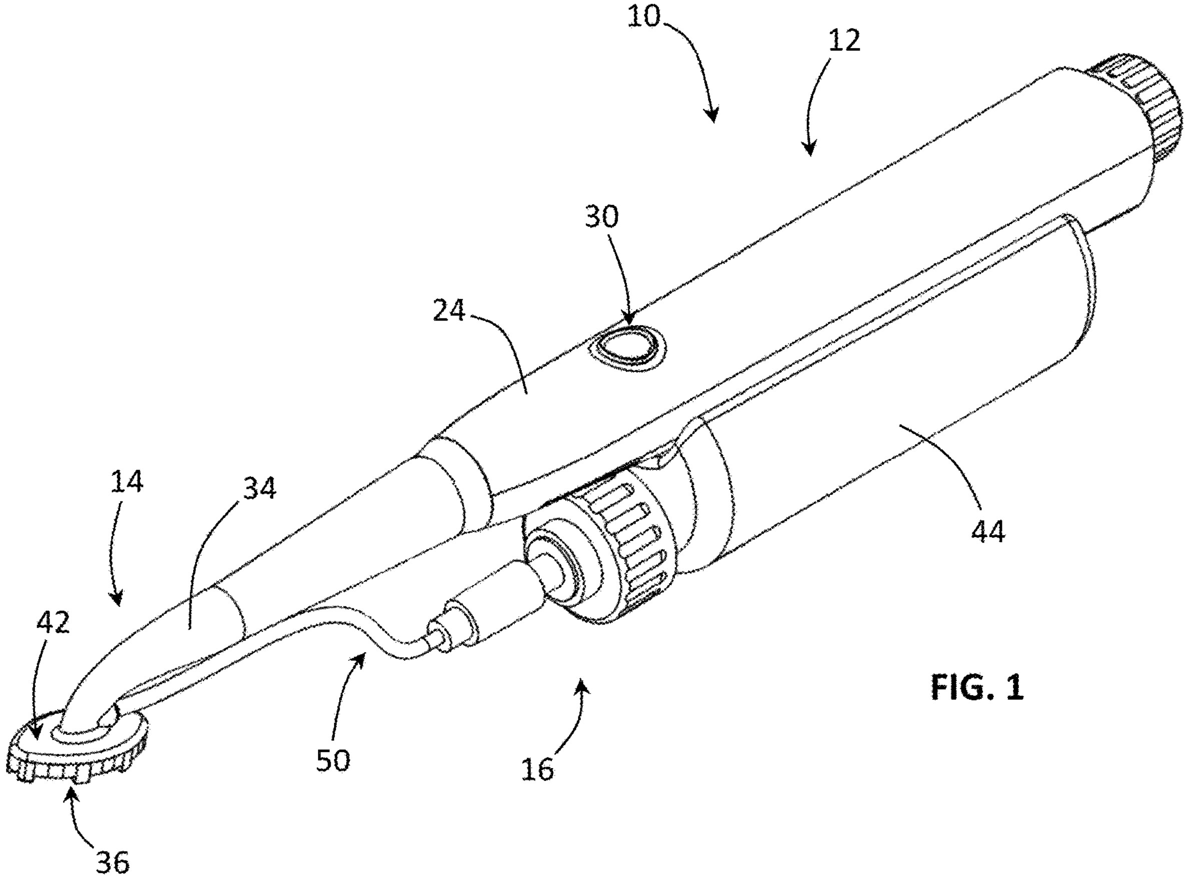
FIG. 1 is a perspective view of one embodiment of a wound-care device.
Figure 2:
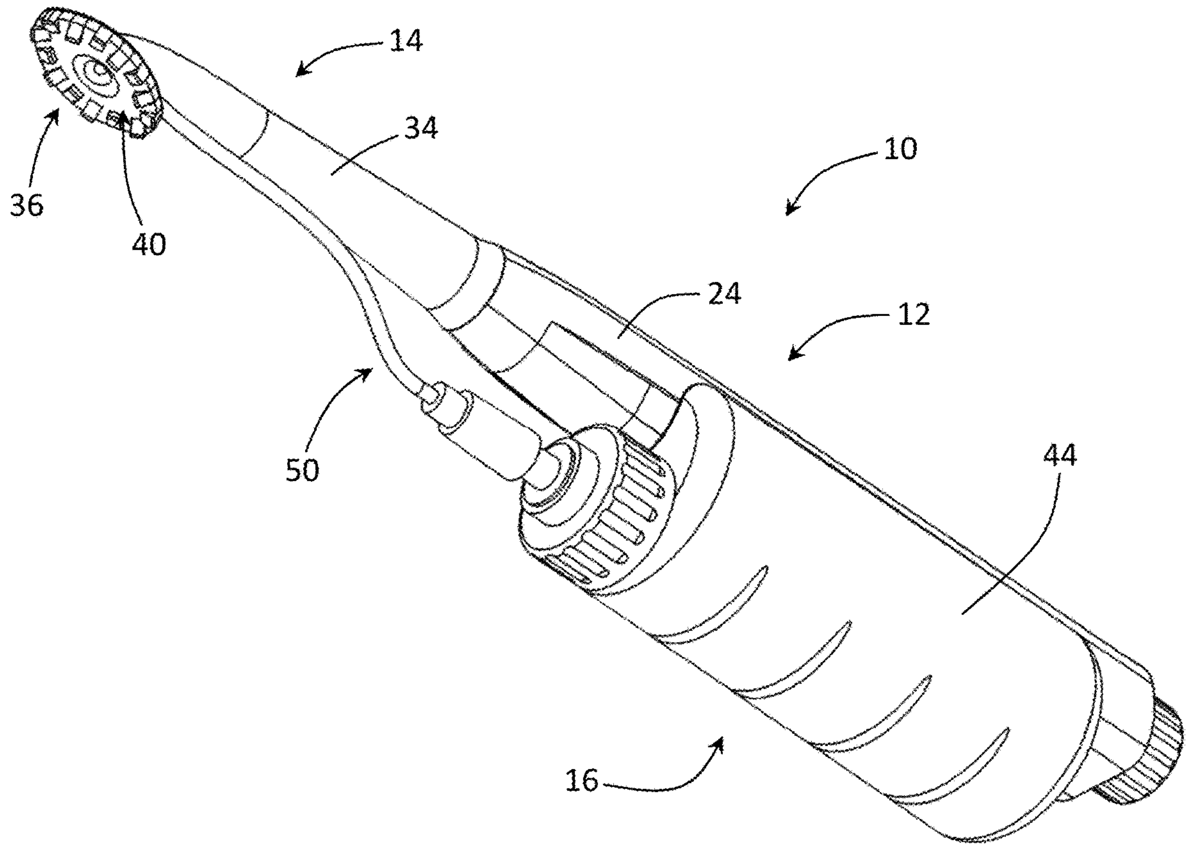
FIG. 2 is another perspective view of the wound-care device of FIG. 1.
Figure 3:
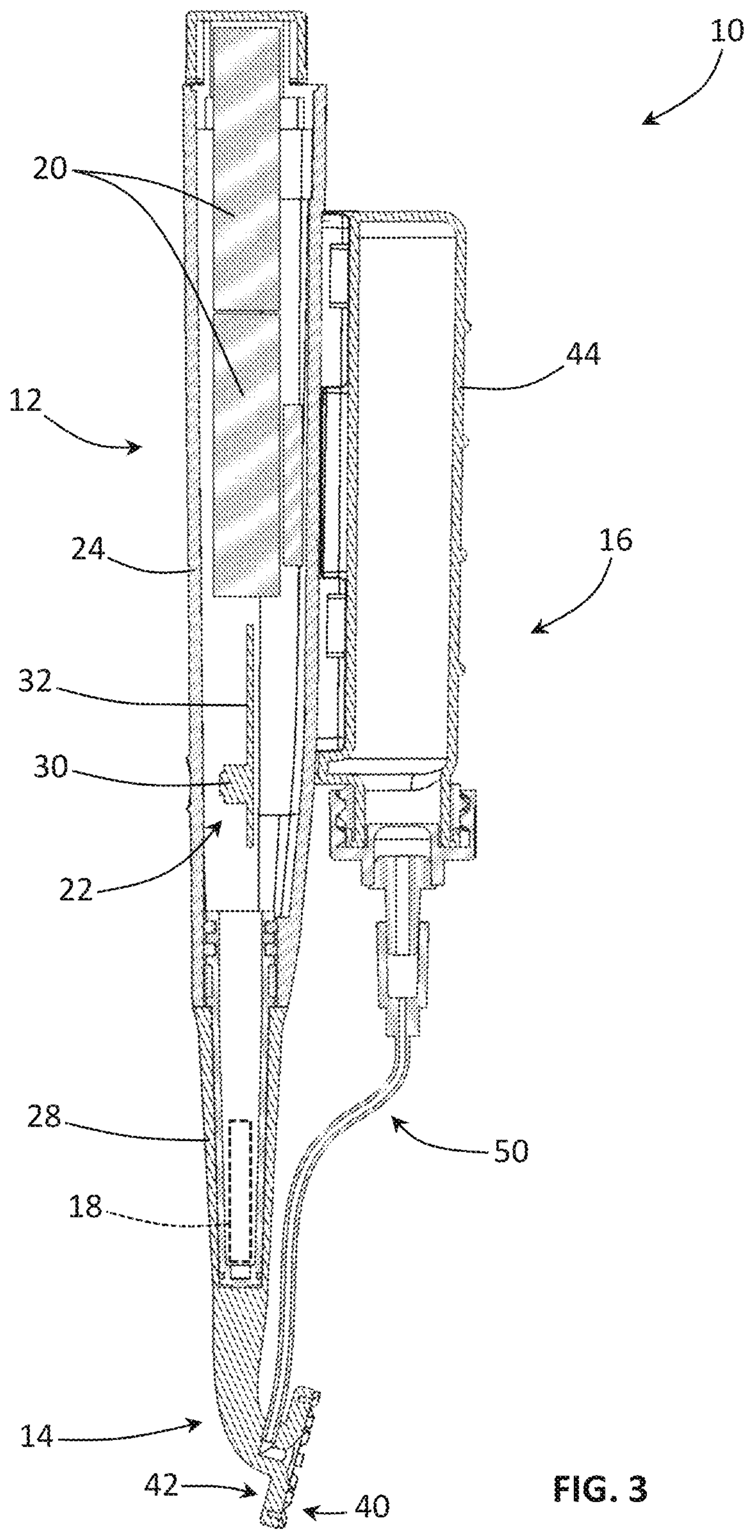
FIG. 3 is a side cross-sectional view of the wound-care device of FIG. 1.
Figure 4:
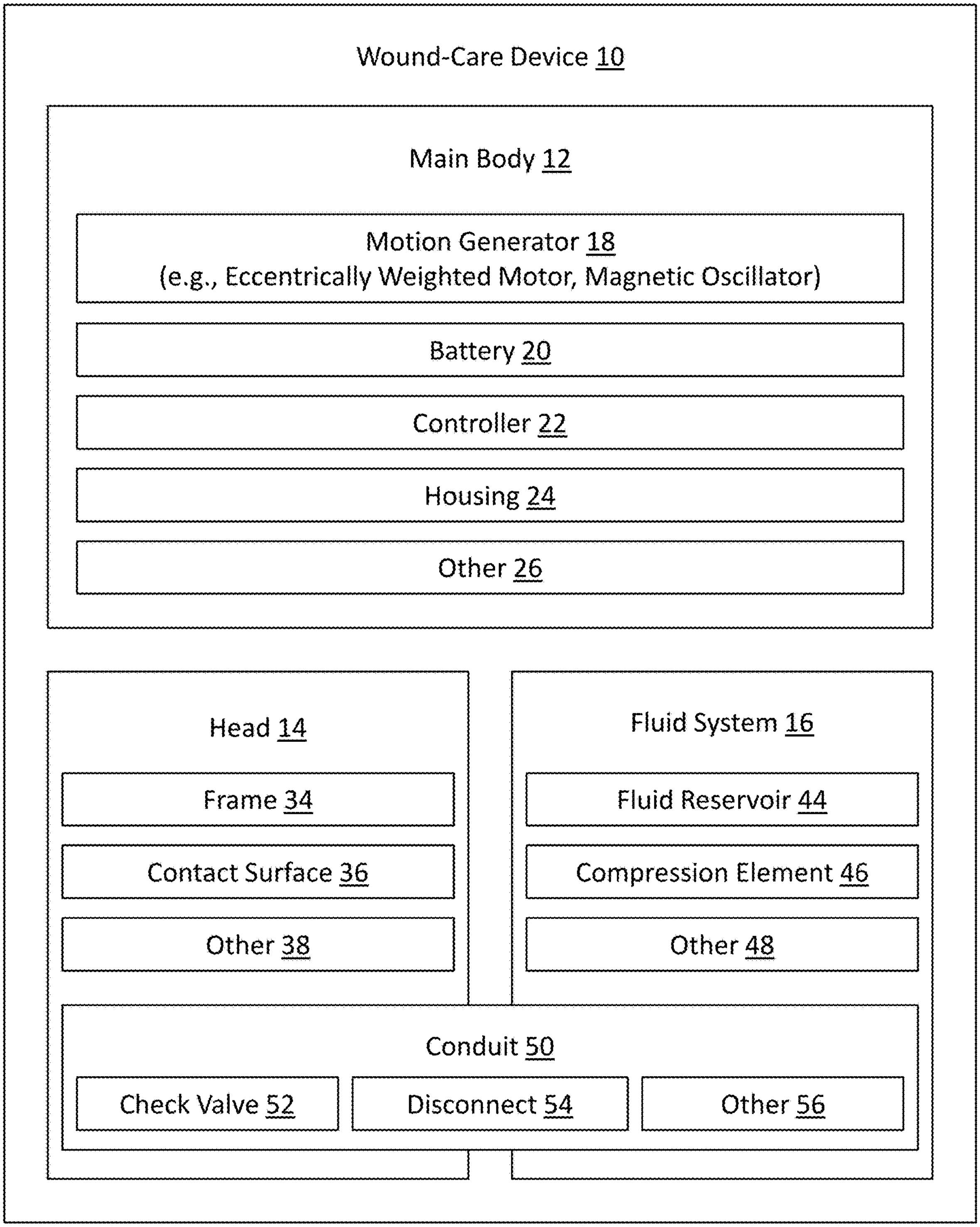
FIG. 4 is a schematic block diagram of one embodiment of a wound-care device.
Figure 5:
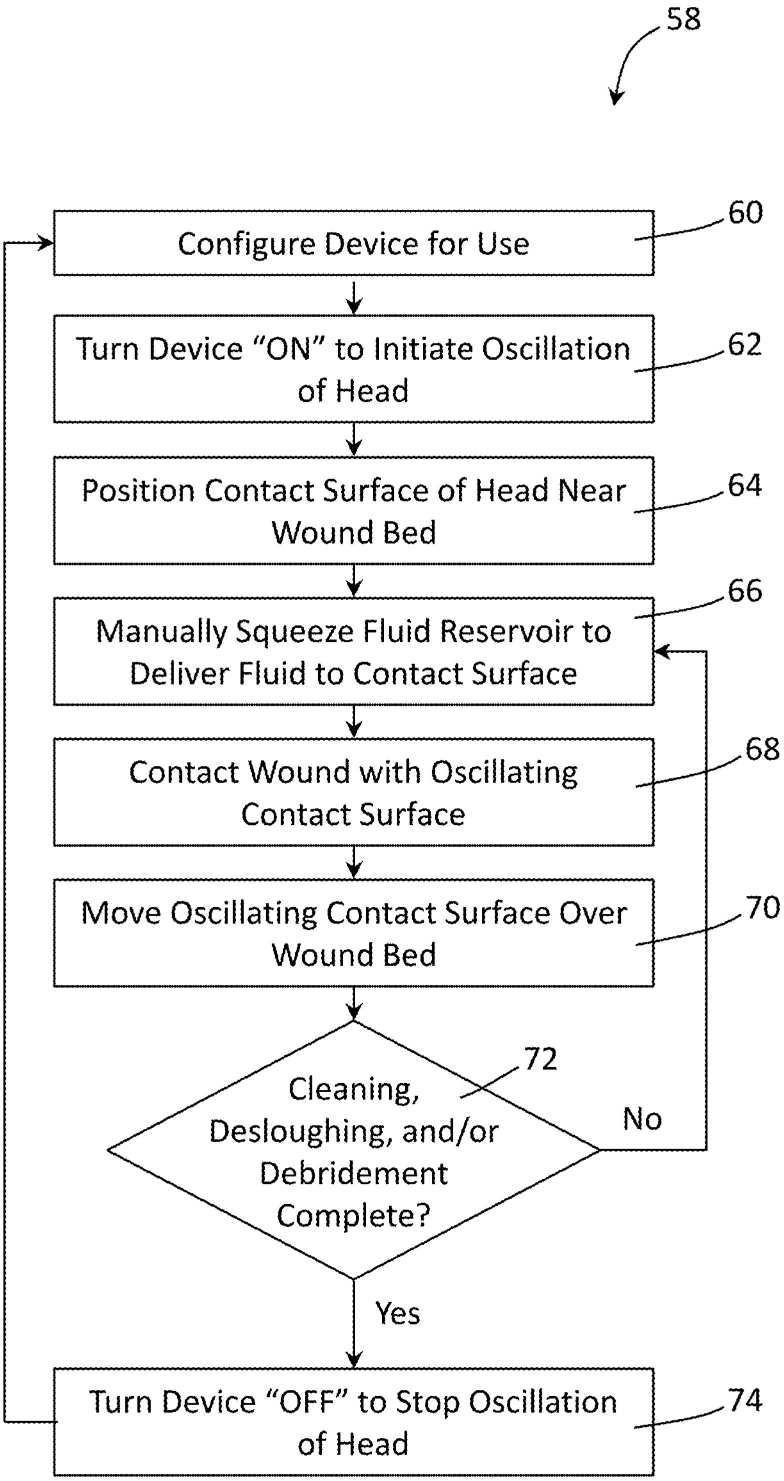
FIG. 5 is a block diagram of one embodiment of a method for using a wound-care device.

Referring to FIG. 5, in selected embodiments, a first method 58 for cleansing, desloughing, and/or debriding a wound bed may begin when a wound-care device 10 is configured 60 for use. Configuring 60 a wound-care device 10 for use may include selecting and installing a contact surface 36 or head 14 that is appropriate, selecting and installing a fluid reservoir 44 and/or conduit 50, or the like or a combination thereof. Thereafter, a wound-care device 10 may be turned 62 "on" (e.g., to start oscillation or other motion of a head 14) and then a contact surface 36 may be positioned 64 proximate a wound bed.

To initiate cleansing, desloughing, and/or debriding, a user may manually squeeze 66 a fluid reservoir 44 to create a flow of fluid to the contact surface 36 and/or place 68 a contact surface 36 in contact with the wound bed. Thereafter, the user may move 70 the contact surface 36 over the wound bed. Oscillation or other motion of the contact surface 36 alone or in combination with a rinsing effect produced by the fluid may tend to clean, deslough, and/or debride the wound bed. Accordingly, a user may continue to dispense fluid, apply the contact surface 36 to the wound bed, and move 70 the contact surface 36 over the wound bed until it is determined 72 that the cleansing, desloughing, and/or debriding is complete. Once it is complete, the wound-care device 10 may be turned 74 "off."

Figure 6:
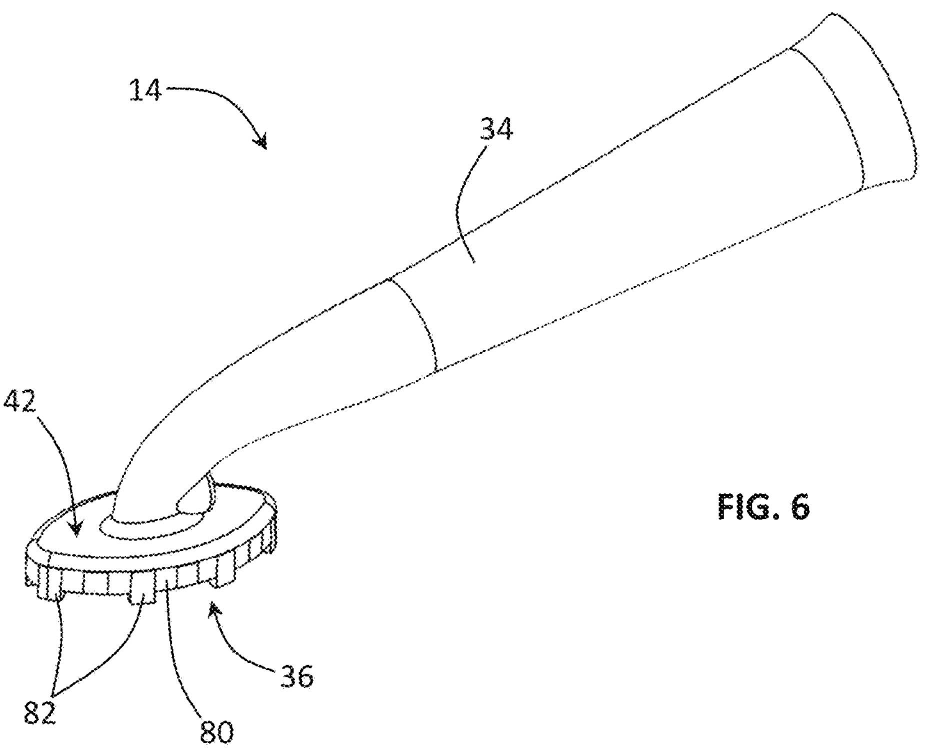
FIG. 6 is a perspective view of a removable head of the wound-care device of FIG. 1.
Figure 7:
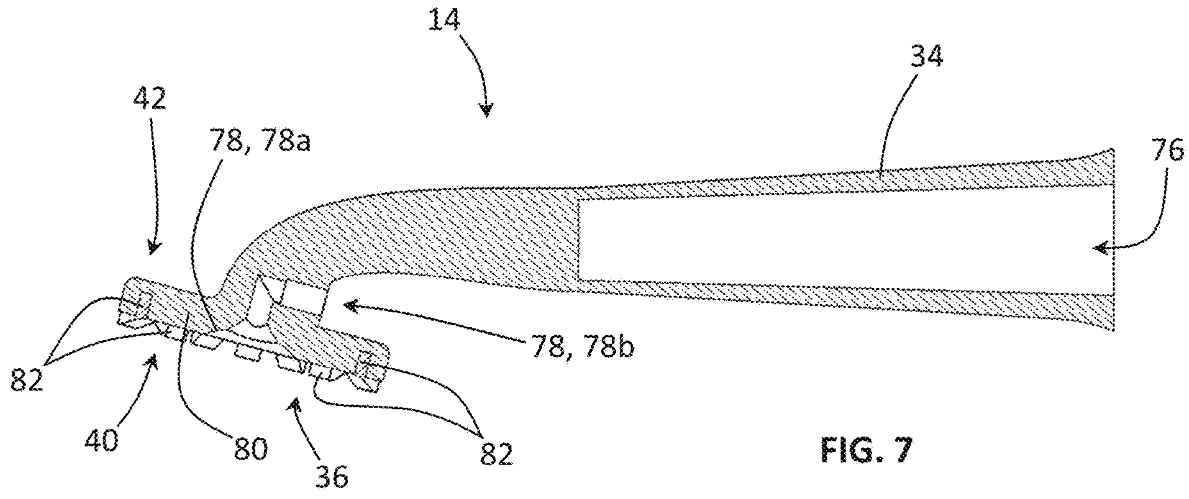
FIG. 7 is a side cross-sectional view of the removable head of FIG. 6.

Referring to FIGS. 6 and 7, in selected embodiments, a frame 34 of a head 14 may have an aperture 76 to support securement to a main body 12. In certain embodiments, such an aperture 76 may be shaped and sized to selectively receive (e.g., frictionally engage via mating tapers) a physical linkage, horn 28, or the like that conducts vibration, oscillation, and/or reciprocation from a main body 12 to a head 14.

In certain embodiments, an aperture 78 may be formed in a head 14 to enable fluid to pass therethrough. For example, a head 14 may include an aperture 78 extending from a back side 42 to a front side 40 of the head 14. A front portion **78*a* of an aperture 78 may be positioned centrally with respect to a contact surface 36. Accordingly, when fluid is expelled through that front portion 78a of the aperture 78, the fluid may flow, migrate, or otherwise move radially outward with respect to the contact surface 36. This radial flow or movement may tend to clean or flush the contact surface 36. A back portion 78b of an aperture 78 may be sized and shaped to receive and secure (e.g., frictionally secure) one end of a conduit 50 therewithin, thereby placing the aperture 78 in fluid communication with a fluid reservoir 44. In embodiments where a wound-care device 10 does not include a fluid system 16 and conduit 50, an aperture 78 in a head 14** may be omitted.

Contact surfaces 36 may have any suitable configuration. Suitable configurations may vary in shape (e.g., rectangular, circular, diamond, oval, or the like), size (e.g., have a length and width in a range from about 5 mm to about 30 mm and preferably a length of about 28 mm and a width of about 14 mm), surface area (e.g., have a footprint of about 200 square millimeters to about 400 square millimeters and preferably a footprint of about 300 square millimeters), surface contour (e.g., flat, convex, or the like), surface texture or profile (e.g., sharp, rounded, course, fine, or the like), channeling (e.g., no channels, radial channels, orthogonally intersecting channels, circumferential channels, or the like or combinations or sub-combinations thereof, composition (e.g., solid polymer, solid elastic polymer, silicone, open cell foam, closed cell foam, or the like), hardness, or the like or in various combinations or sub-combinations thereof. Accordingly, the configuration may be selected to provide a desired performance.

In selected embodiments, contact surfaces 36 may be formed of silicone elastomer or some other polymer in various hardnesses (e.g., having a Shore A hardness in the range from about 15 to about 100, Shore D hardness in the range from about 40 to about 90, or Rockwell R hardness in the range from about 50 to about 100). In certain embodiments, a contact surface 36 may comprise a base 80 and one or more extensions 82 extending from the base 80. The base 80 and the one or more extensions 82 may be formed of different materials to support different functions. For example, a base 80 may be formed of a material that is easily formable and relatively rigid (e.g., polymer), while one or more extensions 82 may be formed of a material that is compatible with the function of cleansing, desloughing, and/or debriding a wound (e.g., an elastomer having a desired Shore A hardness). In selected embodiments, one or more extensions 82 may be insert molded or otherwise embedded within a base 80 to enable the extensions 82 to securely extend away from the base 80 and define a texture or profile for the contact surface 36. In other embodiments, a base 80 and one or more extensions 82 extending from the base 80 may form a monolithic unit by themselves (e.g., be formed together of a polymeric material as a seamless unit in a molding process) or together with other portions (e.g., a frame 37 and aperture 78) of the head 14 corresponding thereto.

In selected embodiments, varying the number and sharpness of the edges of one or more extensions 82, the pointedness of one or more extensions 82, the height of one or more extensions 82, the lateral offset of one extension 82 with respect to one or more extensions 82 that are adjacent thereto, the hardness of the material (e.g., polymer, elastomer, or the like) forming the one or more extensions 82, and/or the pressure applied by the user (e.g., the force with which the user urges the contact surface 36 against a wound bed) may be used to control the aggressiveness of the cleansing, desloughing, and/or debrided. Accordingly, extensions 82 providing a high concentration of sharp edges formed of a relatively hard material may produce a contact surface 36 that is very aggressive, while extensions 82 having an absence (or lesser quantity) of sharp edges (e.g., rounded edges) and/or being formed of a relatively soft material may provide a contact surface 36 that is very gentle. Fluid dispensed from the one or more apertures 78 may flow over and in between extensions 82 and flush the contact surface 36 of debris during use of a wound-care device 10. This flushing action may better cleanse a wound bed and facilitate dislodgement and removal of bacteria, biofilm, and devitalized tissues during cleansing, desloughing, and/or debridement.

In certain embodiments, the extensions 82 of a contact surface 36 may have different edges and/or hardnesses associated therewith. For example, the extensions 82 associated with the ends (e.g., distal and proximal ends) of a contact surface 36 may be formed of a harder material than the more centrally located extensions 82. Alternatively, or in addition thereto, the extensions 82 associated with the ends (e.g., distal and proximal ends) of the contact surface 36 may have sharper edges than the more centrally located extensions 82. Accordingly, a user may apply different portions of a contact surface 36 to a wound bed to provide a different effect.

Figure 8:
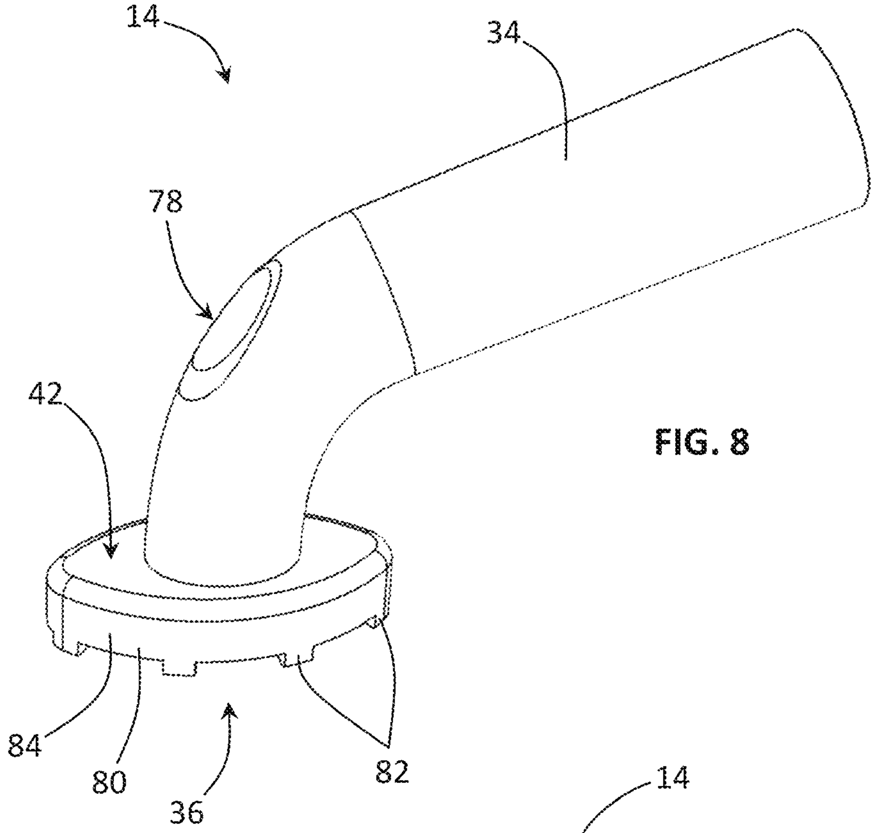
FIG. 8 is a perspective view of an alternative embodiment of a removable head for a wound-care device.
Figure 9:
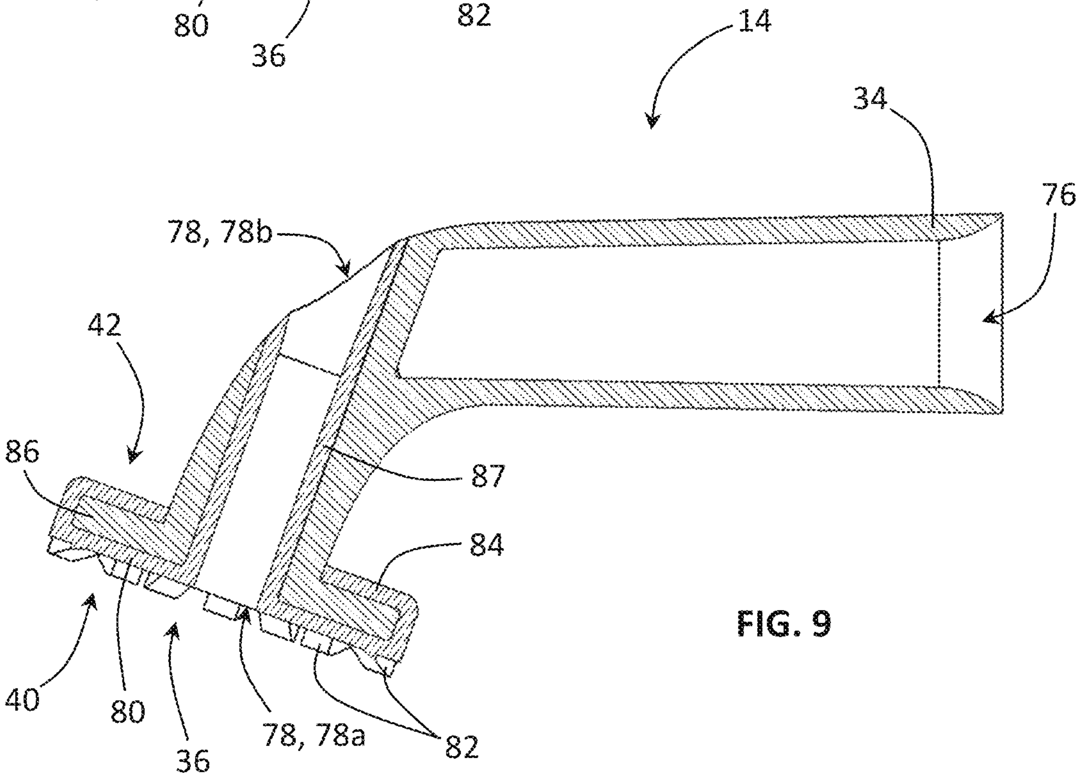
FIG. 9 is a side cross-sectional view of the removable head of FIG. 8.
Figure 10:
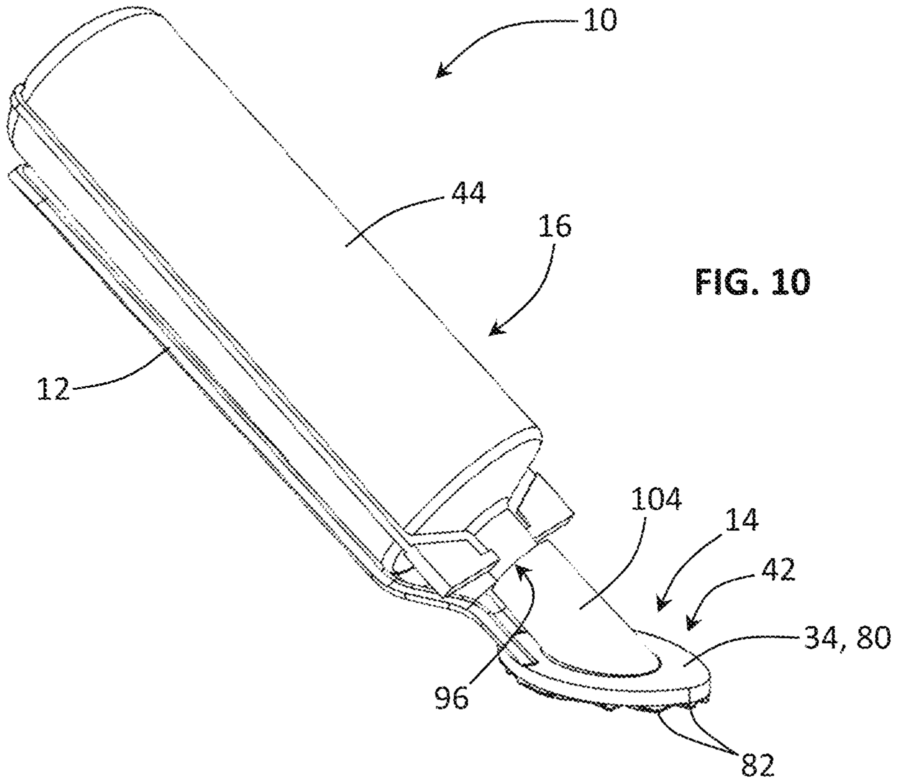
FIG. 10 is a perspective view of an alternative embodiment of a wound-care device.
Figure 11:
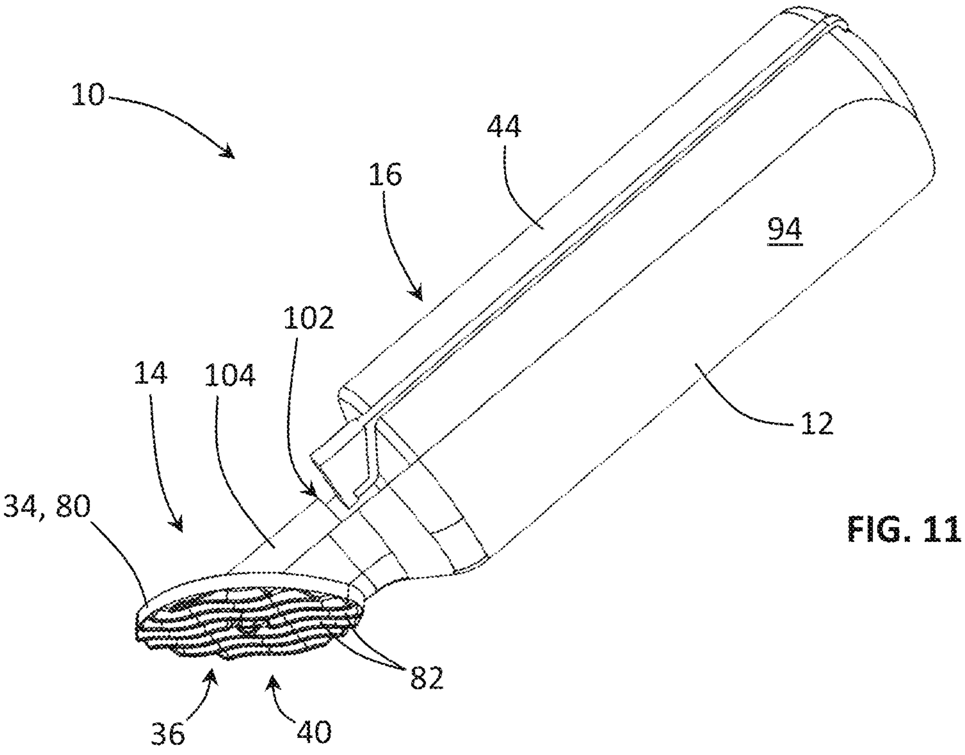
FIG. 11 is another perspective view of the wound-care device of FIG. 10.
Figure 12:
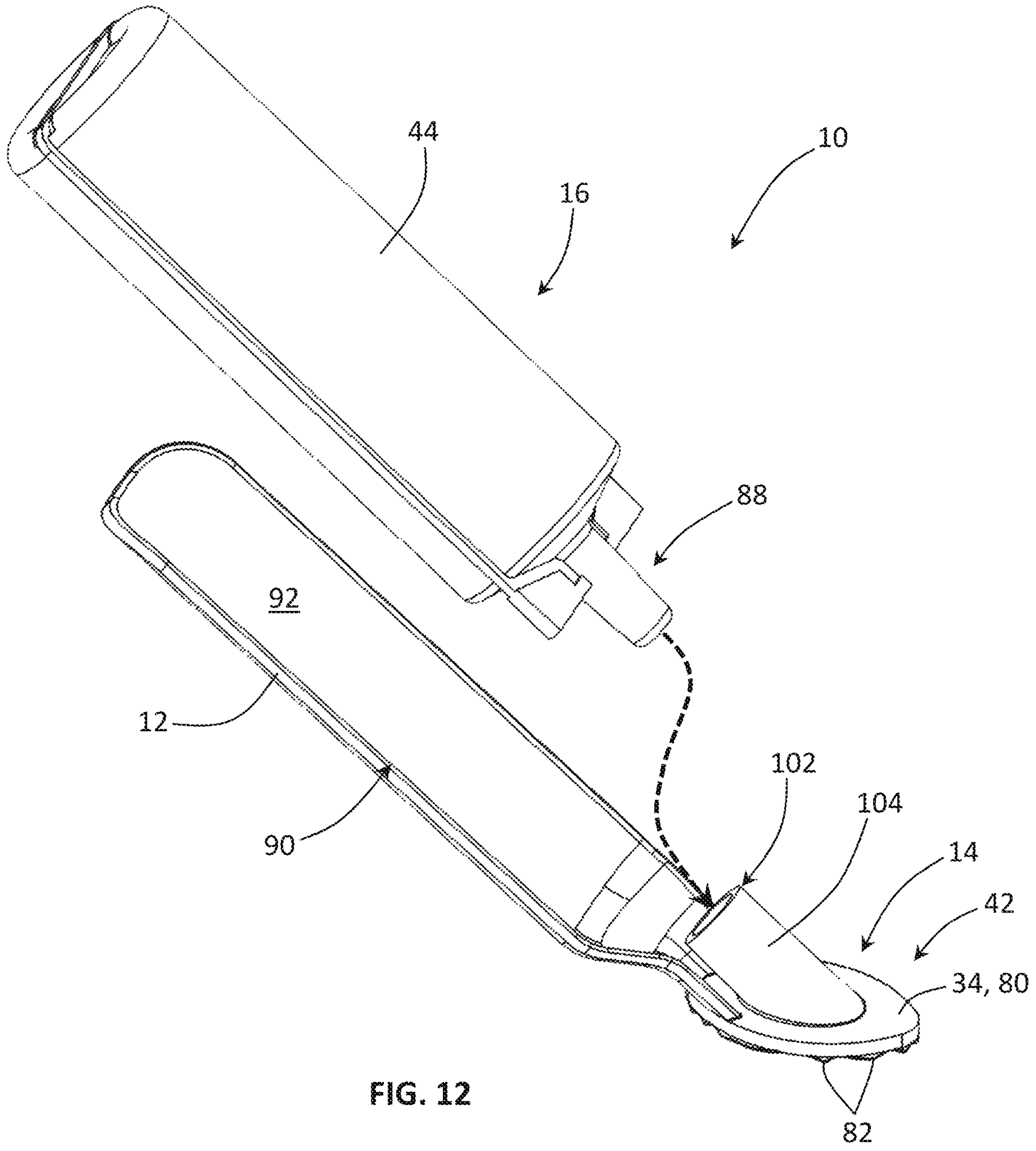
FIG. 12 is an exploded perspective view of the wound-care device of FIG. 10.
Figure 13:
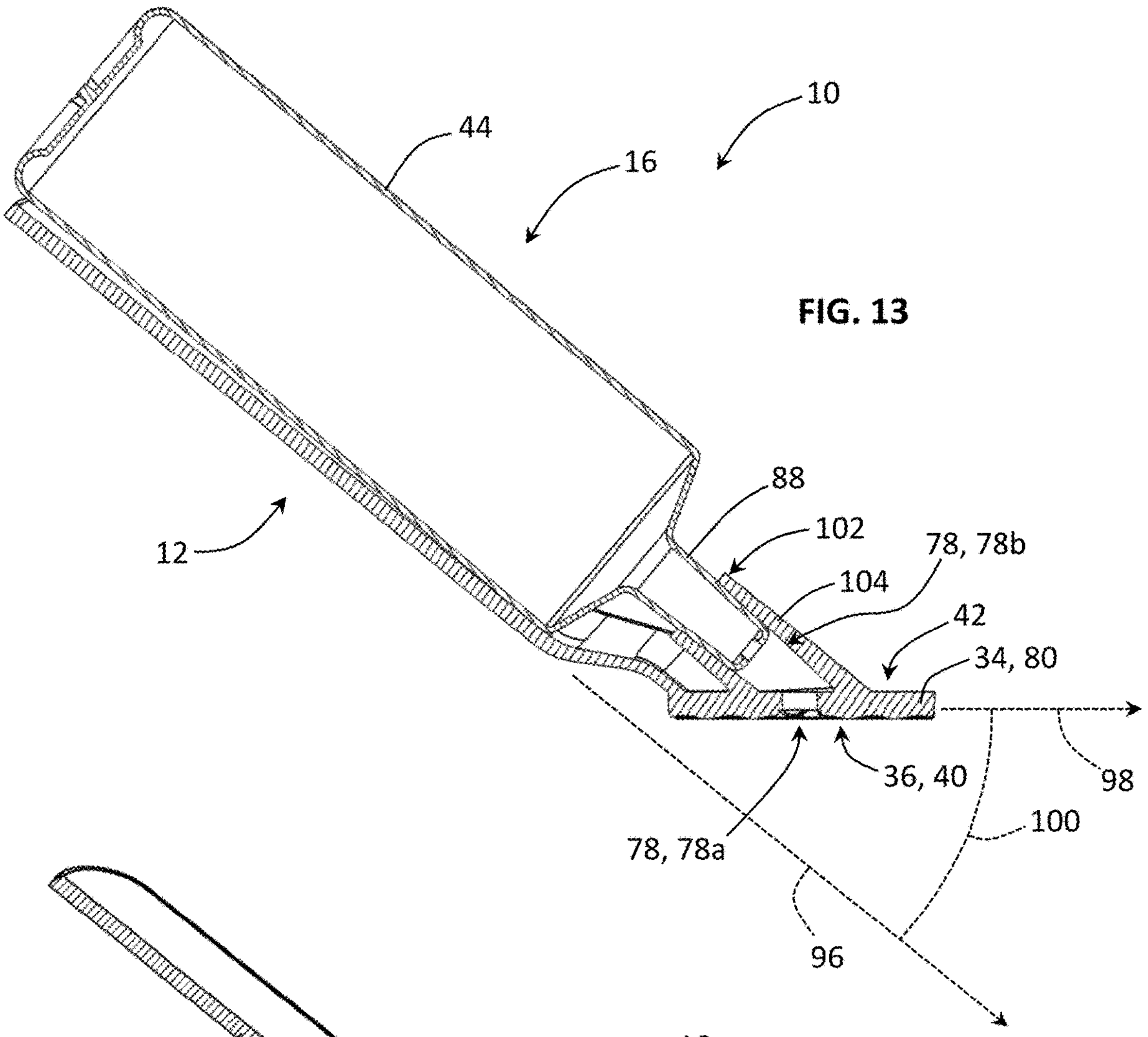
FIG. 13 is a side cross-sectional view of the wound-care device of FIG. 10.

Referring to FIGS. 8 and 9, in selected embodiments, a contact surface 36 may be formed as a boot 84 (e.g., a boot formed of an elastomer) that slips over a supporting structure 86 formed as part of a frame 34. In such embodiments, a boot 84 may form (e.g., monolithically form) both one or more of the extensions 82 and a base 80 from which the one or more extension 82 project. Such an embodiment may allow selected portions of a head 14 to be reusable, and the boot 84 to include the contact surface 36 and be a single use item formed of a very inexpensive elastomeric material, to reduce cost of use of the device. This may also simplify manufacturing, facilitate interchangeability, or the like. Alternatively, a boot 84 may be applied to a frame 34 in a two-step, over-molding process. In such embodiments, the resulting head 14 may be a single use item in its entirety.

In certain embodiments, a contact surface 36 that is removable (e.g., a base 80 portion of a contact surface 36) may include a length of tubing 87 extending away from a back thereof. A conduit 50 of a fluid system 16 may connect to such tubing to deliver fluid to the contact surface 36. Accordingly, in such embodiments, fluid may never contact a frame 34. The length of the tubing 87 may be selected to reduce the likelihood of biological contamination of the conduit 50. In selected embodiments, the length of the tubing 87 may be about 1 cm to about 13 cm. As a result, a contact surface 36 and associated tubing 87 may be discarded after use, while a conduit 50 may be used multiple times.

Referring to FIGS. 10-13, in selected embodiments, a wound-care device 10 may be configured for maximum utility and minimum cost. Accordingly, in certain embodiments, a wound-care device 10 may be non-electric (e.g., a motion generator and 18 and corresponding or related structures such as a battery 20, controller 22, housing 24, and/or horn 28 may be omitted from a wound-care device 10). Alternatively, or in addition thereto, a wound-care device 10 may be single use. For example, in selected embodiments, a wound-care device 10 may comprise a main body 12 or handle portion that is monolithically formed together with a head 14 (e.g., the main body 12 and head 14 may be injection molded as a single unit). The material forming the main body 12 and head 14, including the contact surface 36 of the head 14, may be homogeneous throughout. This may reduce the cost of manufacturing a wound-care device 10, make a wound-care device 10 viable as a single use device, and avoid all sanitation and sterilization issues associated with reuse of any part of a wound-care device 10.

In certain embodiments, the material used to form the main body 12 and head 14 of a wound-care device 10 may be or reflect a compromise between the structural requirements for the main body 12 and head 14 and the structural requirements for a contact surface 36 of the head 14. In selected embodiments, the material may be or comprise a polymer having a Rockwell R hardness of about 100 or lower. For example, the material may be or comprise polypropylene (e.g., polypropylene random copolymer with a Rockwell R hardness of about 90 and a flexural modulus of about 966 MPa). Accordingly, in certain embodiments, a wound-care device 10 may comprise a main body 12, head 14, and contact surface 36 that are monolithically formed (e.g., injection molded as a single unit) in a polymeric material such as polypropylene.

A fluid system 16 paired with a main body 12 that is simplified and head 14 combination may be similarly simplified. For example, a conduit 50 may be omitted and a fluid system 16 may comprise a fluid reservoir 44 (e.g., a fluid reservoir 44 in the form of a squeeze bottle, single use container, saline bullet, or the like) having an outlet 88 that directly engages (e.g., is inserted into a mating back portion **78*b* of) an aperture 78 of a head 14. In certain embodiments, a fluid reservoir 44** may be a sterile, single-use, 15 ml saline bullet.

In selected embodiments, a main body 12 or handle portion of a wound-care device 10 may have a concavity 90 formed therein. A concavity 90 may be sized and shaped to support a fluid reservoir 44 at least partially therewithin. For example, a fluid reservoir 44 (e.g., a squeeze bottle, saline bullet, or the like) may have a cylindrical side wall. Accordingly, a concavity 90 of a main body 12 may have an interior surface 92 that follows, tracks, or otherwise cradles at least a portion of a cylindrical side wall of a fluid reservoir 44. Such cradling, alone or in combination with insertion of an outlet 88 of a fluid reservoir 44 into an aperture 78 of a head 14, may secure a fluid reservoir 44 in place or make it easier for a user to hold a fluid reservoir 44 in place during use (e.g., during movement of a wound-care device 10 with respect to a wound bed and/or squeezing of a fluid reservoir 44 to expel fluid).

In certain embodiments, an exterior surface 94 of a main body 12 may track or follow an interior surface 92. Alternatively, or in addition thereto, the spacing between the interior surface 92 and the exterior surface 94 may be relatively small. Accordingly, a thickness of a material forming a main body 12 (e.g., a thickness of a material located between the interior surface 92 and the exterior surface 94) may be relatively thin and/or substantially uniform. This may reduce the amount of material needed to produce a wound-care device 10. Additionally, in selected embodiments, a curvature of a main body 12 that produces a concavity 90 may effectively define or form at least one corrugation running lengthwise from one end of a main body 12 to the other. Such a corrugation may stiffen a main body 12 against bending without requiring large or larger amounts of material.

In selected embodiments, a main body 12 may extend in a first direction 96 (e.g., may have a line or axis of symmetry that extends in a first direction 96). A head 14 may extend away from a main body 12 in a second direction 98 that is different from the first direction 96 (e.g., may have a line or axis of symmetry that extends in a second direction 98 that is different from the first direction 96). For example, in certain embodiments, a head 14 may extend away from a main body 12 in a second direction 98 that departs from the first direction 96 at an angle 100 in a range from about 25 to about 55 degrees and preferably at an angle 100 in a range from about 40 to about 50 degrees. In selected embodiments, a head 14 may extend away from a main body 12 in a second direction 98 that departs from the first direction 96 at an angle 100 of about 45 degrees.

In selected embodiments and/or uses, a fluid reservoir 44 may be omitted from a wound-care device 10 comprising a main body 12 that is simplified and head 14 combination. In such embodiments, cleansing, desloughing, and/or debridement of a wound bed may be conducted in a "dry" manner without the addition of any fluid. Alternatively, fluid may be applied in a separate process. For example, a liquid, gel, paste, or the like may be applied to a wound bed in a first process that precedes and is separate from using a wound-care device 10 to clean, deslough, or debride the wound bed.

When a fluid reservoir 44 is omitted, a concavity 90 formed in a main body 12 may provide a location for a finger (e.g., an index finger) of a user to extend and rest during use of the wound-care device 10 corresponding thereto. That is, rather than cradling a fluid reservoir 44 (e.g., a saline bullet having a diameter that is about equal to or slightly larger than a typical finger diameter), a concavity 90 may cradle a finger (e.g., an index finger) of a user. When using a wound-care device 10 in such a manner, a user may place the tip of whichever finger is cradled within a concavity 90 against a proximal end 102 of a structure 104 or conduit forming a back portion **78*b* of an aperture 78 extending through the head 14. This engagement or abutment with the tip of the finger may enable a user to apply a desired or sufficient amount of pressure to a head 14 as it contacts a wound bed and/or better sense or control how much pressure is applied through a head 14** to a wound bed.

In certain embodiments, a finger positioned within a wound-care device 10 may enable a user to selectively apply specific regions of a head 14 or contact surface 36 (e.g., a distal end of a head 14, either side of a head 14, a proximal end of a head 14) to a wound bed with greater user control of the force applied and the angle of the contact surface 36 relative to a wound bed. This may give a user superior control over a pressure and location of engagement between a head 14 and a wound bed and better results or performance for the medical procedure.

In selected embodiments, a main body 12 that is simplified and head 14 combination may be distributed in an individually wrapped, sterile condition. In certain embodiments, wound-care devices 10 that are individually wrapped may be combined into packs of a selected quantity (e.g., a pack of about five or some other quantity corresponding to about a two-week supply). Accordingly, when tending to a patient, a medical professional may select a pack of wound-care devices 10, open and use a wound-care device 10 to clean, deslough, or debride a wound bed of a patient and/or teach the patient how to do it, and then send the wound-care devices 10 that remain unopened in the pack home with the patient for the patient use in the interim before the next visit with a medical professional. In certain embodiments, such a pack may include or be provided to a patient with a selected number of fluid reservoirs 44 containing fluid (e.g., a selected number of saline bullets of a size that fits the main body 12 that is simplified and head 14 combination).

Figure 14:
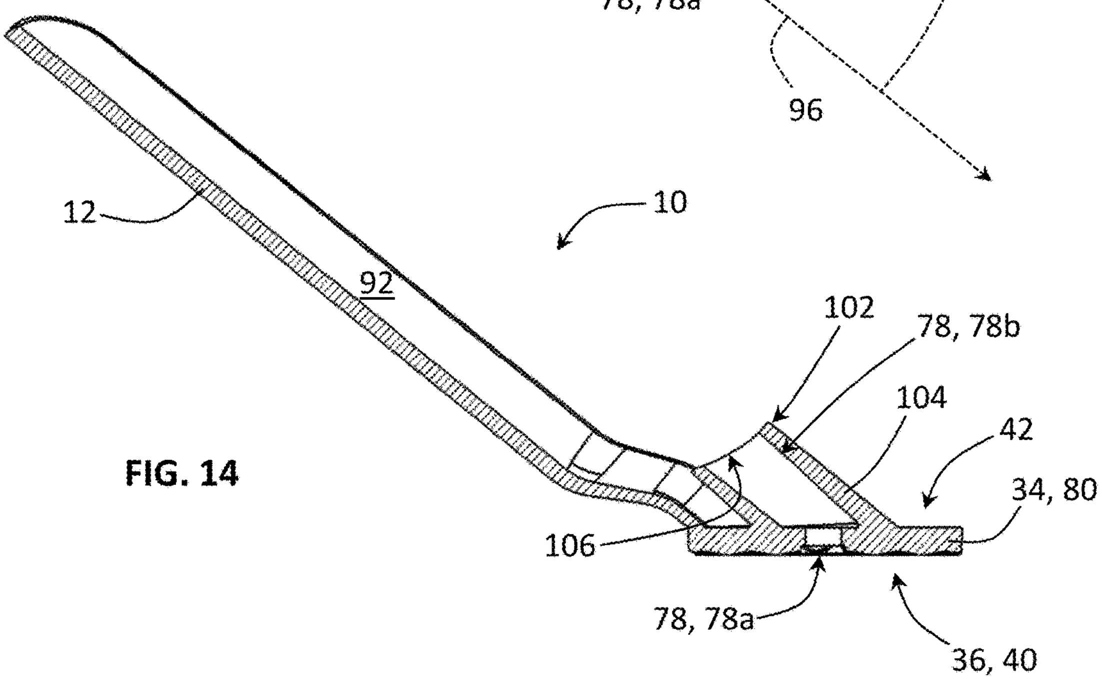
FIG. 14 is a side cross-sectional view of another alternative embodiment of a wound-care device.

Referring to FIG. 14, in selected embodiments, a proximal end 102 of a structure 104 or conduit forming a back portion **78*b* of an aperture 78 extending through the head 14** may be shaped so as to comfortably engage a fingertip of a user. For example, a proximal end 102 may have a curvature 106 formed therein that follows or replicates a portion of the curvature of a fingertip. Accordingly, a structure 104 or conduit may be configured to alternatively and with equal effectiveness engage an outlet 88 of a fluid reservoir 44 and a tip of a finger of a user.

In certain embodiments, a structure 104 or conduit may be sized and shaped to engage a conduit 50 with a Luer-taper type connection. For example, an interior surface of an aperture 78 may be sized and shaped to receive and frictionally engage a Luer-type, male, slip-fit connector. Alternatively, or in addition thereto, an exterior surface of a structure 104 or conduit may be sized and shaped to receive and frictionally engage a Luer-type, female, slip-fit connector. Such an arrangement may enable conduits 50 that are standard or commonly available intravenous tubing, intravenous connectors, saline bags, or the like to be used as part of a fluid system 16.

Figure 15:
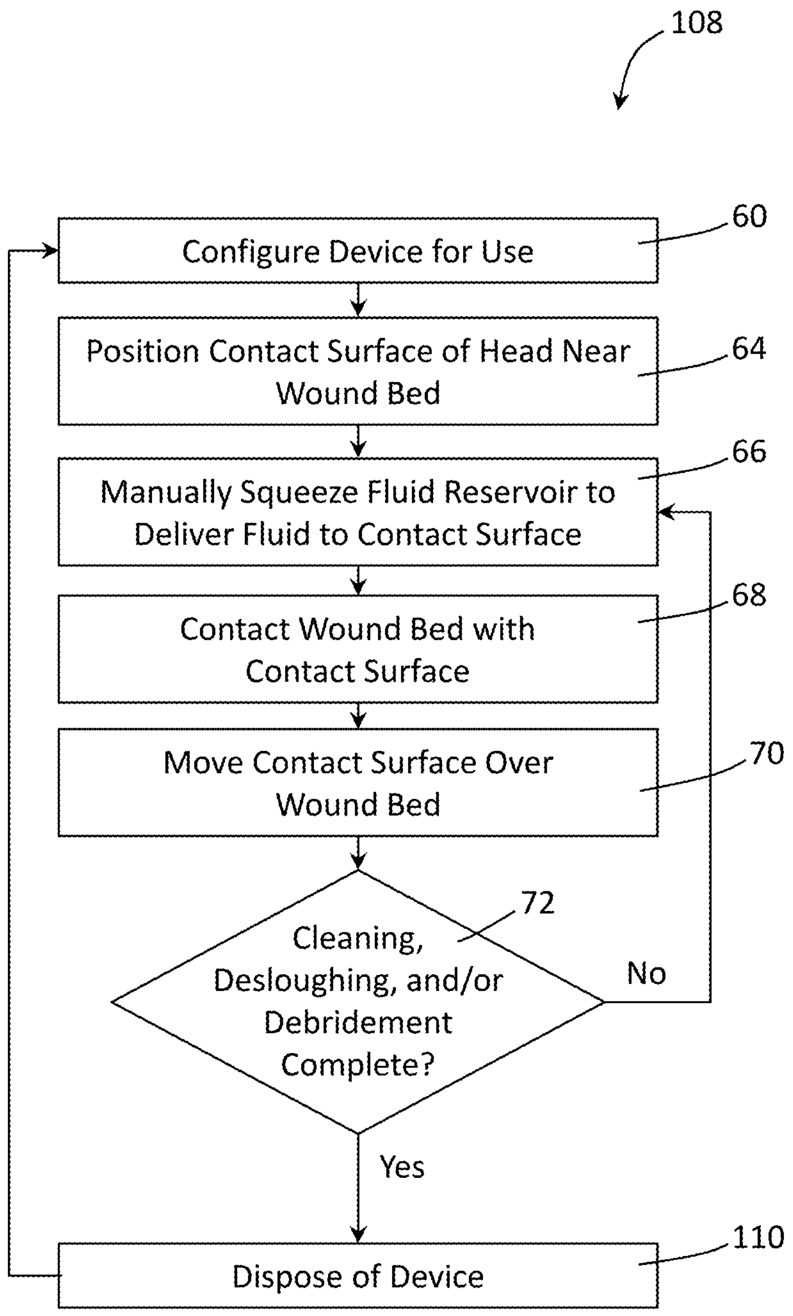
FIG. 15 is a block diagram of an alternative embodiment of a method for using a wound-care device.

Referring to FIG. 15, in selected embodiments, a second method 108 for cleansing, desloughing, and/or debriding a wound bed may begin when a wound-care device 10 is configured 60 for use. Configuring 60 a wound-care device 10 for use may include selecting a wound-care device 10 with a contact surface 36 that is appropriate, opening packaging containing the wound-care device 10, and installing a fluid reservoir 44 (e.g., selecting a saline bullet, removing a cap of the saline bullet, inserting an outlet 88 of the saline bullet into a back portion **78*b* of an aperture 78 of a head 14). Thereafter, a wound-care device 10 may be moved to position 64 a contact surface 36** proximate a wound bed.

To initiate cleansing, desloughing, and/or debriding, a user may manually squeeze 66 a fluid reservoir 44 to create a flow of fluid to the contact surface 36 and/or place 68 a contact surface 36 in contact with the wound bed. Thereafter, the user may move 70 the contact surface 36 over the wound bed. Moving 70 the contact surface 36 with respect to the wound bed in combination with a rinsing effect produced by the fluid may tend to clean, deslough, and/or debride the wound bed. The moving 70 of the contact surface may be side to side, front to back, at some angle, in small circles, or the like or a combination or sub-combination thereof. Accordingly, a user may continue to dispense fluid, apply the contact surface 36 to the wound bed, and move 70 the contact surface 36 over the wound bed until it is determined 72 that the cleansing, desloughing, and/or debriding is complete. Once it is complete, the wound-care device 10 may be discarded 110.

Figure 16:
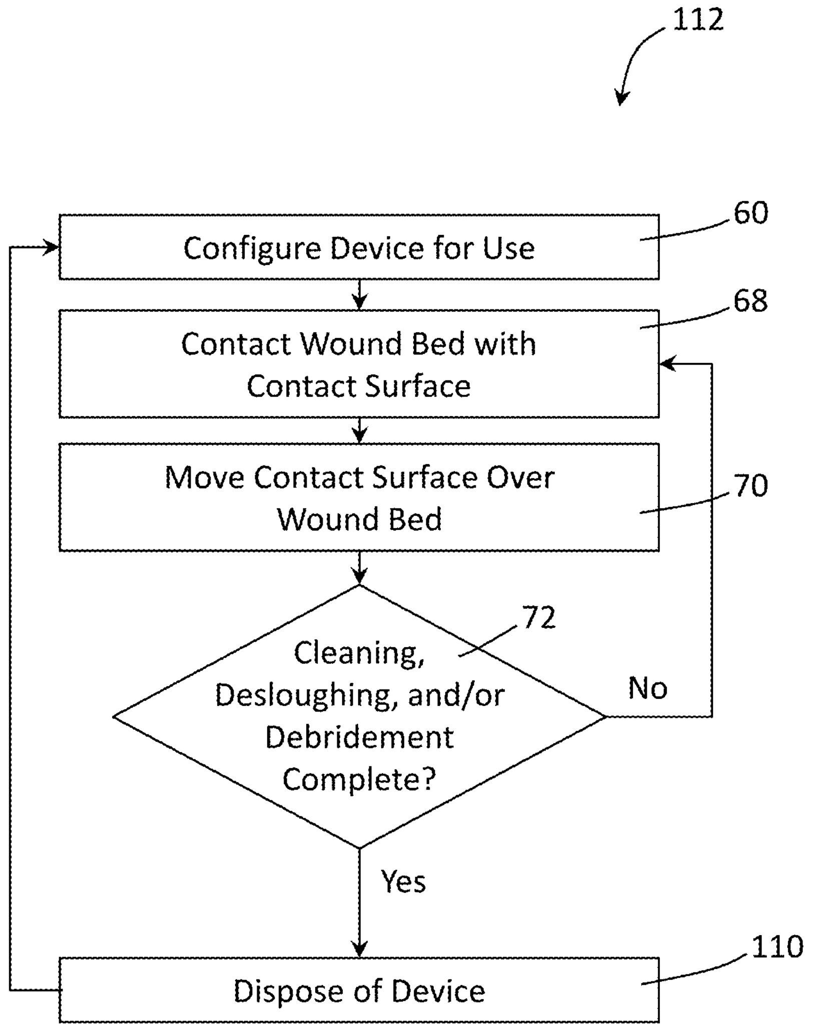
FIG. 16 is a block diagram of another alternative embodiment of a method for using a wound-care device.
Figure 20:
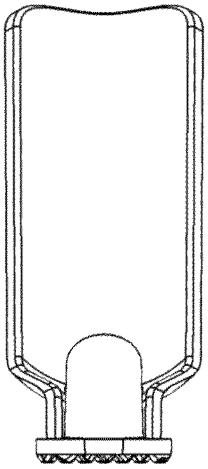
FIG. 20 is a front view of the main body and head portions of the wound-care device of FIG. 10.
Figure 22:
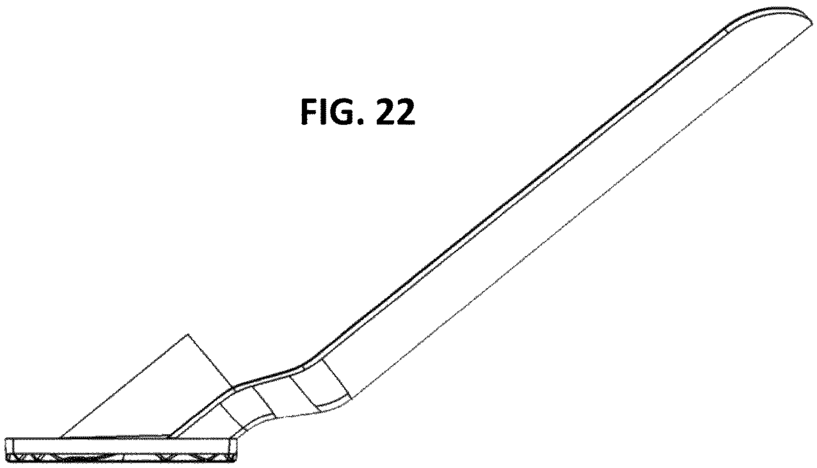
FIG. 22 is a first side view of the main body and head portions of the wound-care device of FIG. 10.
Figure 21:
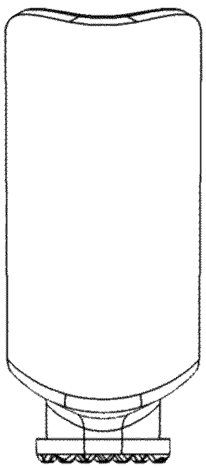
FIG. 21 is a rear view of the main body and head portions of the wound-care device of FIG. 10.
Figure 23:
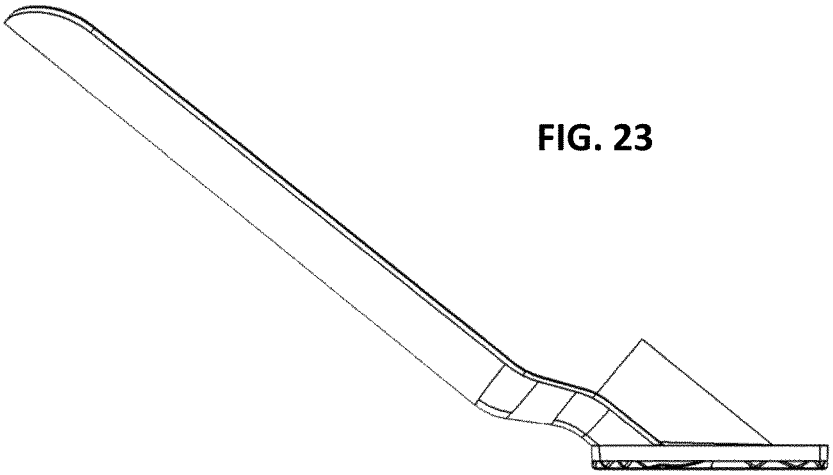
FIG. 23 is a second, opposite side view of the main body and head portions of the wound-care device of FIG. 10.
Figure 24:
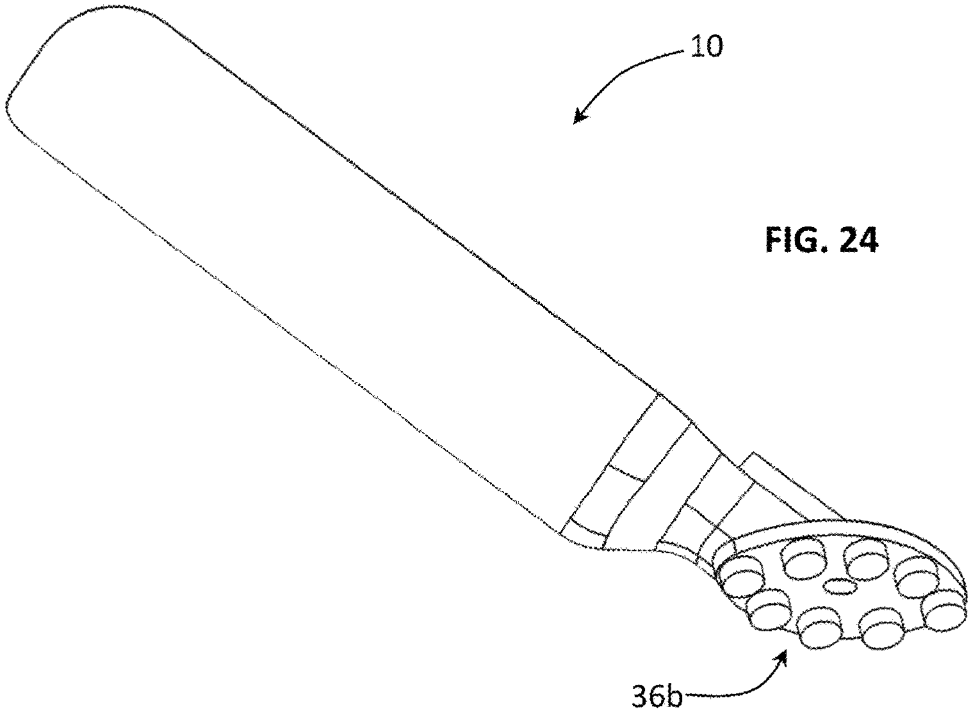
FIG. 24 is a perspective view of another alternative embodiment of a wound-care device.
Figure 25:
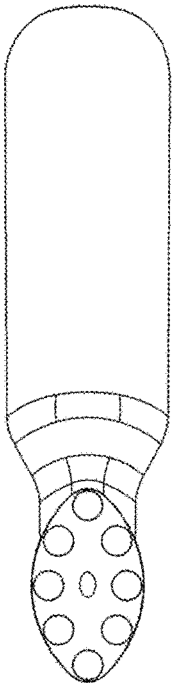
FIG. 25 is a bottom view of the wound-care device of FIG. 24.
Figure 26:
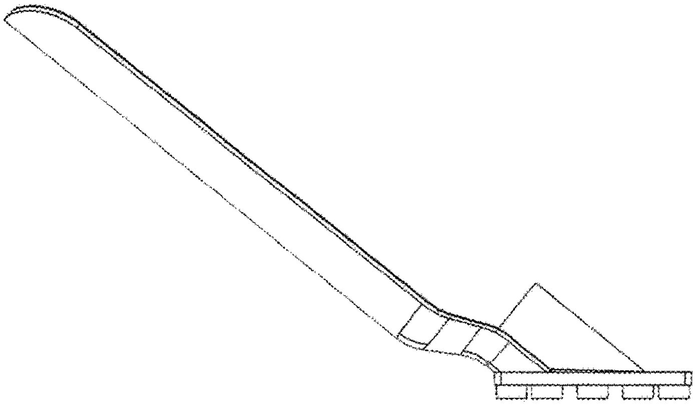
FIG. 26 is a side view of the wound-care device of FIG. 24.
Figure 27:
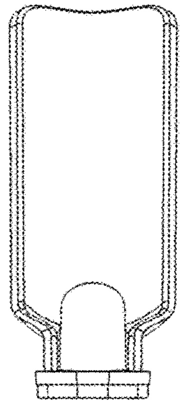
FIG. 27 is a front view of the wound-care device of FIG. 24.

Referring to FIG. 16, in selected embodiments, a third method 112 for cleansing, desloughing, and/or debriding a wound bed may begin when a wound-care device 10 is configured 60 for use. Configuring 60 a wound-care device 10 for use may include removing the device from sterile packaging. To initiate cleansing, desloughing, and/or debriding, a user may manually place 68 a contact surface 36 in contact with the wound bed. Thereafter, the user may move 70 the contact surface 36 over the wound bed. Moving 70 the contact surface 36 with respect to the wound bed may tend to clean, deslough, and/or debride the wound bed. If using a finger (e.g., an index finger) to guide a wound-care device 10 or a head 14 of a wound-care device 10, a user may selectively change a pressure and/or orientation of a head 14 with respect to a wound bed to more precisely control an outcome of the procedure. Accordingly, a user may continue to apply the contact surface 36 to the wound bed and move 70 the contact surface 36 over the wound bed until it is determined 72 that the cleansing, desloughing, and/or debriding is complete. Once it is complete, the wound-care device 10 may be discarded 110.

In certain embodiments, a third method 112 may be preceded by the application of a fluid or the like to a wound bed. Accordingly, a third method 112 may benefit from the fluid without the fluid being applied while a contact surface 36 is in contact with a wound bed or as a contact surface 36 is moved 70 over a wound bed.

In other embodiments, a wound may be treated in one session using a combination of two methods (e.g., a second method 108 and a third method 112). For example, for a first period of time, a user may employ various steps (e.g., positioning 64, squeezing 66, placing 68, and/or moving 70) corresponding to a second method 108 (e.g., a set method), then remove a fluid reservoir 44 (e.g., remove a saline bullet positioned within a concavity 90) and transition to employing various steps (e.g., placing 68 and/or moving 70) corresponding to a third method 112 (e.g., a dry method) wherein a finger placed within a concavity 90 to provide greater control over the force, orientation, etc. of a wound-care device 10. Such a hybrid method may end by using fluid remaining in the fluid reservoir 44 to flush or rinse of the wound bed.

Referring to FIGS. 17-31, different wounds may fall on different locations within a wound infection continuum. Accordingly, the treatment needed for different wounds may also vary. For example, in certain situations, a wound infection continuum may be divided into multiple zones (e.g., three zones). A first zone may correspond to a lower level of infection, while one or more other zones may correspond to one or more higher levels of infection. Accordingly, one or more methods (e.g., a first method 58, second method 108, or third method 112) may enable wounds corresponding to the first zone to be treated differently from wounds corresponding to one or more other zones.

For example, if an examination of a wound bed reveals that a wound corresponds to the second zone or other higher zone of a wound infection continuum, a user (e.g., a medical professional) may select, install, and/or use a contact surface 36 that is relatively aggressive. Conversely, if an examination of a wound bed reveals that a wound corresponds to the first zone of a wound infection continuum, a user may select, install, and/or use a contact surface 36 that is less aggressive.

Alternatively, in one or more methods (e.g., a first method 58, second method 108, or third method 112), a wound may be evaluated based on the presence and/or nature of devitalized tissue. For example, in certain situations, a wound may be classified into one of three situations. A first situation may correspond to devitalized tissue that is firmly adherent. A second situation may correspond to devitalized tissue that is loosely adherent. A third situation may correspond to a wound that could simply benefit from cleansing. Accordingly, one or more methods (e.g., a first method 58, second method 108, or third method 112) may enable wounds corresponding to the first, second, and third situations to be treated differently.

For example, if an examination of a wound bed reveals that a wound corresponds to devitalized tissue that is firmly adherent, a user may select, install, and/or use a contact surface 36 that is relatively aggressive. Such as a contact surface 36 may be referred to as a debridement surface **36*a*. If an examination of a wound bed reveals that a wound corresponds to devitalized tissue that is loosely adherent, a user may select, install, and/or use a contact surface 36 that is intermediately aggressive. Such a contact surface 36 may be referred to as a desloughing surface 36*b*. If an examination of a wound bed reveals that a wound could simply benefit from cleansing, a user may select, install, and/or use a contact surface 36 that is not aggressive. Such a contact surface 36 may be referred to as a cleansing surface 36***c*.

A contact surface 36 may have any suitable configuration. In general, increasing the sharpness and/or number of the edges of the extensions 82 of a contact surface 36 may result in a more aggressive effect when applied to a wound bed. Accordingly, a cleansing surface 36*c* may have few if any sharp edges, a desloughing surface 36*b* may have an intermediate number of edges and/or edges of intermediate sharpness, and a debridement surface 36*a* may have a significant number of edges and/or edges of increased sharpness.

FIGS. 17-23 show one embodiment of a main body 12 that is simplified and head 14 combination where the head 14 includes (e.g., is monolithically formed or molded to have) a cleansing surface 36*c*.

FIGS. 24-27 show one embodiment of a main body 12 that is simplified and head 14 combination where the head 14 includes (e.g., is monolithically formed or molded to have) a desloughing surface 36*b*.

Figure 28:
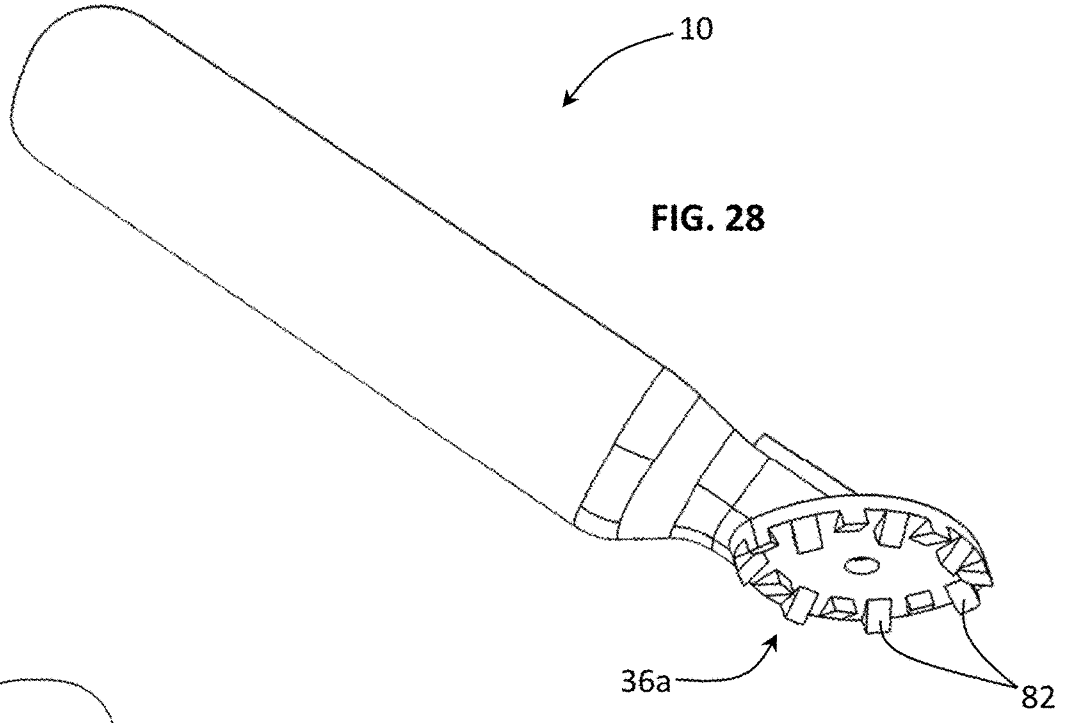
FIG. 28 is a perspective view of another alternative embodiment of a wound-care device.
Figure 29:
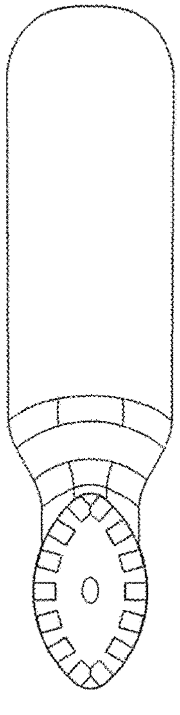
FIG. 29 is a bottom view of the wound-care device of FIG. 28.
Figure 30:
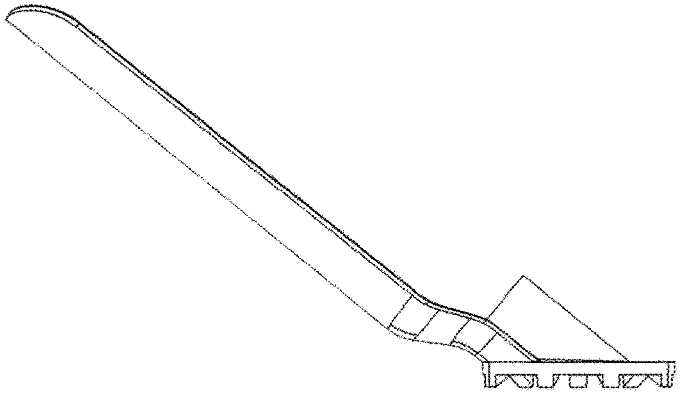
FIG. 30 is a side view of the wound-care device of FIG. 28.
Figure 31:
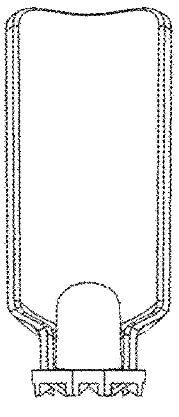
FIG. 31 is a front view of the wound-care device of FIG. 28.
Figure 35:
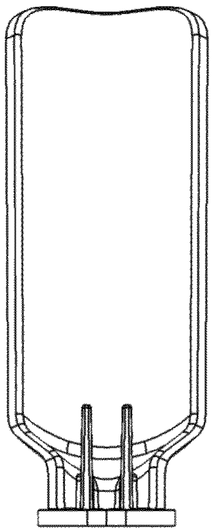
FIG. 35 is a front view of the wound-care device of FIG. 32.
Figure 37:
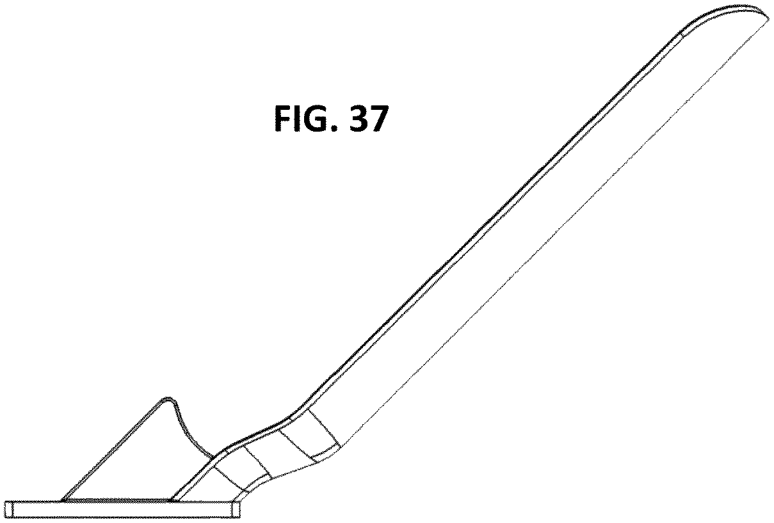
FIG. 37 is a first side view of the wound-care device of FIG. 32.
Figure 36:
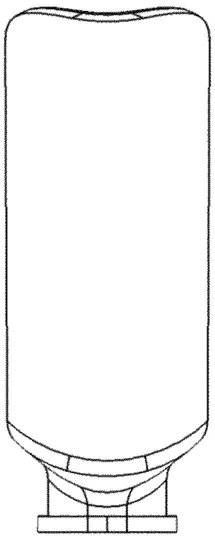
FIG. 36 is a rear view of the wound-care device of FIG. 32.
Figure 38:
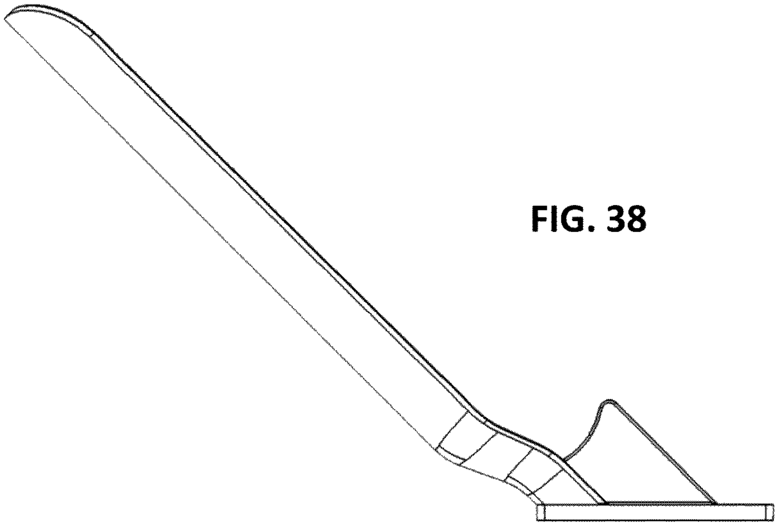
FIG. 38 is a second, opposite side view of the wound-care device of FIG. 32.
Figure 42:
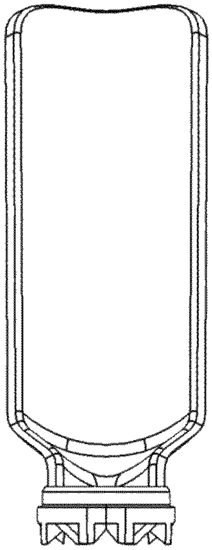
FIG. 42 is a front view of the wound-care device of FIG. 39.
Figure 44:
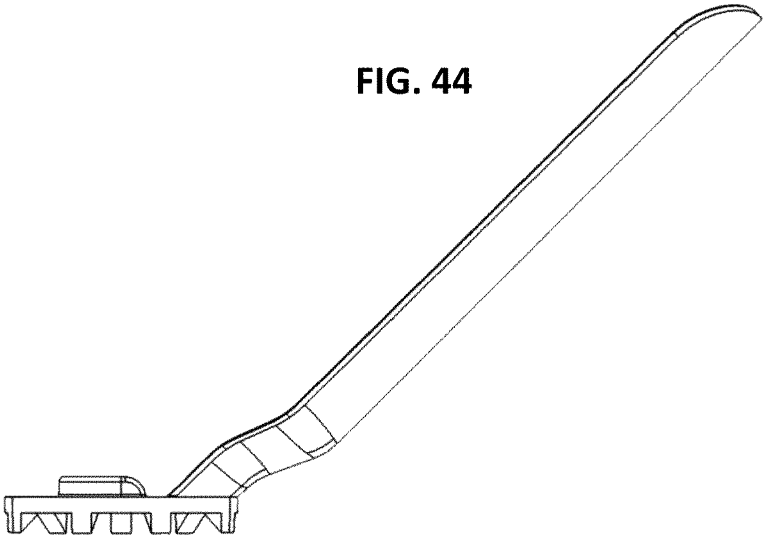
FIG. 44 is a first side view of the wound-care device of FIG. 39.
Figure 43:
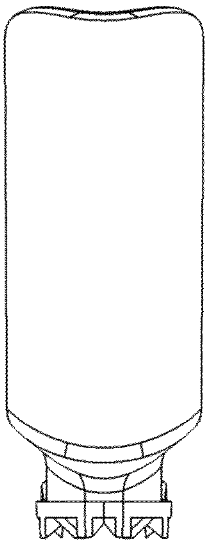
FIG. 43 is a rear view of the wound-care device of FIG. 39.
Figure 45:
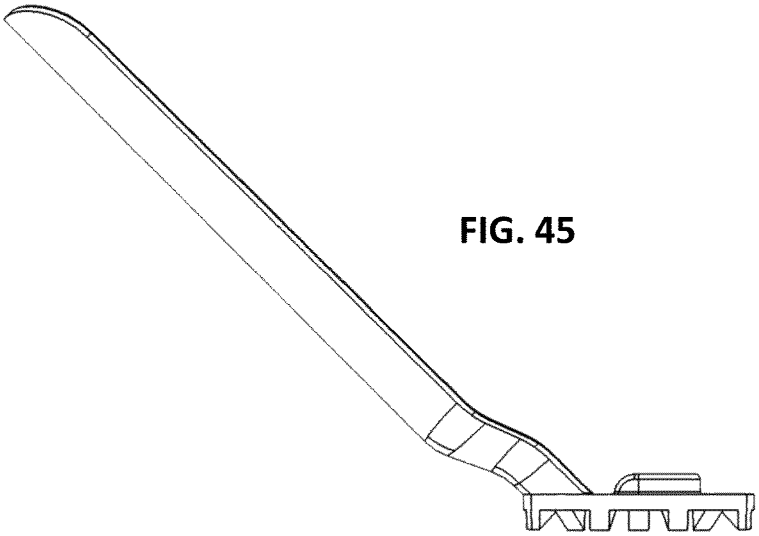
FIG. 45 is a second, opposite side view of the wound-care device of FIG. 39.
Figure 49:
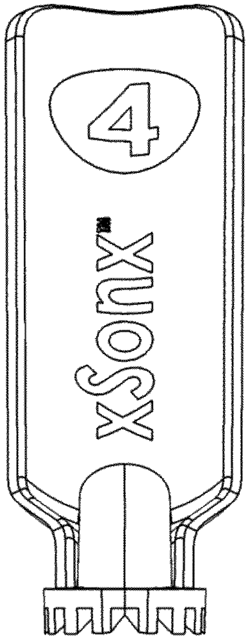
FIG. 49 is a front view of the wound-care device of FIG. 46.
Figure 51:
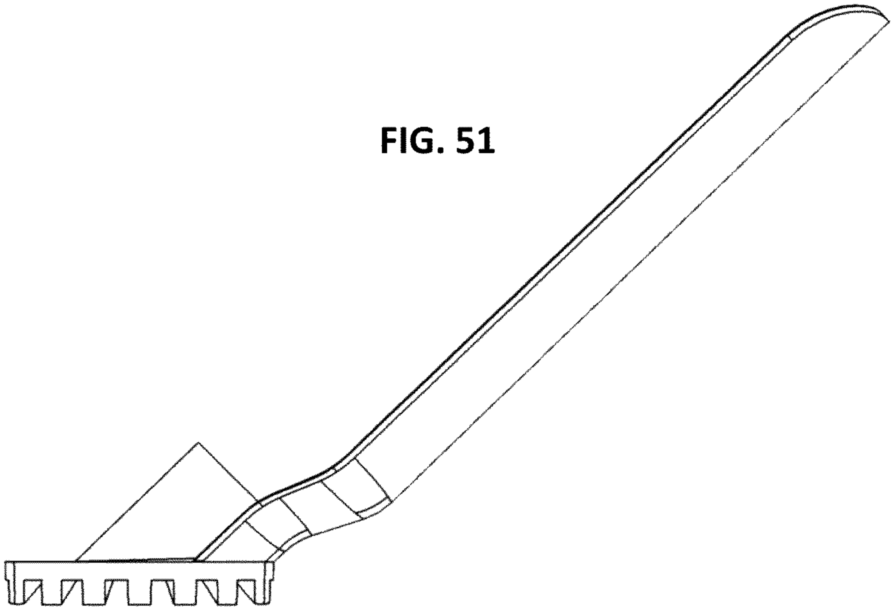
FIG. 51 is a first side view of the wound-care device of FIG. 46.
Figure 50:
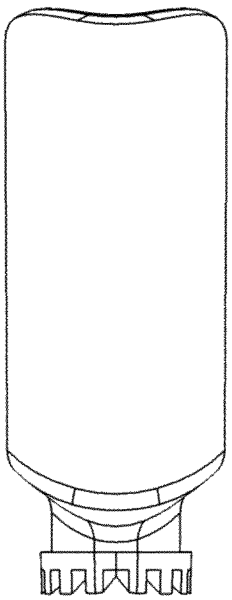
FIG. 50 is a rear view of the wound-care device of FIG. 46.
Figure 52:
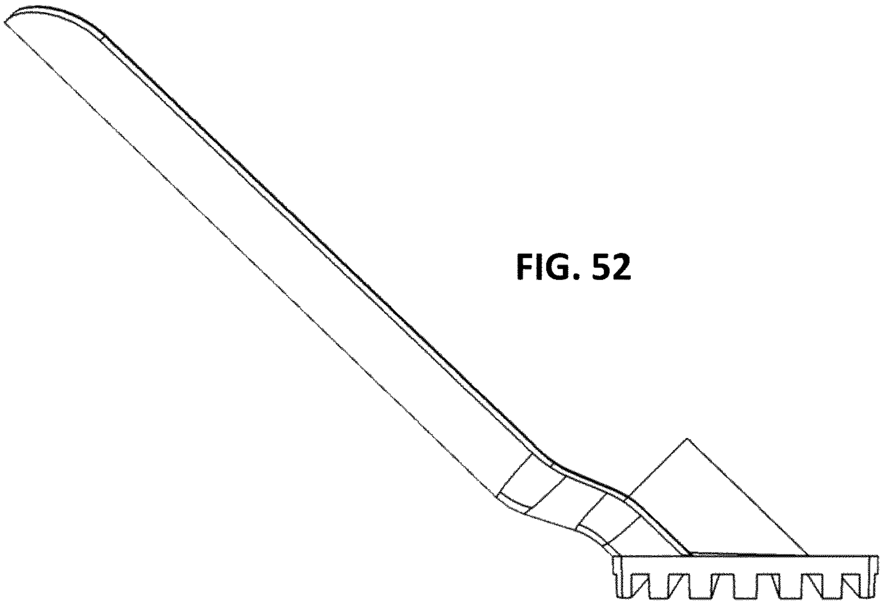
FIG. 52 is a second, opposite side view of the wound-care device of FIG. 46.
Figure 53:
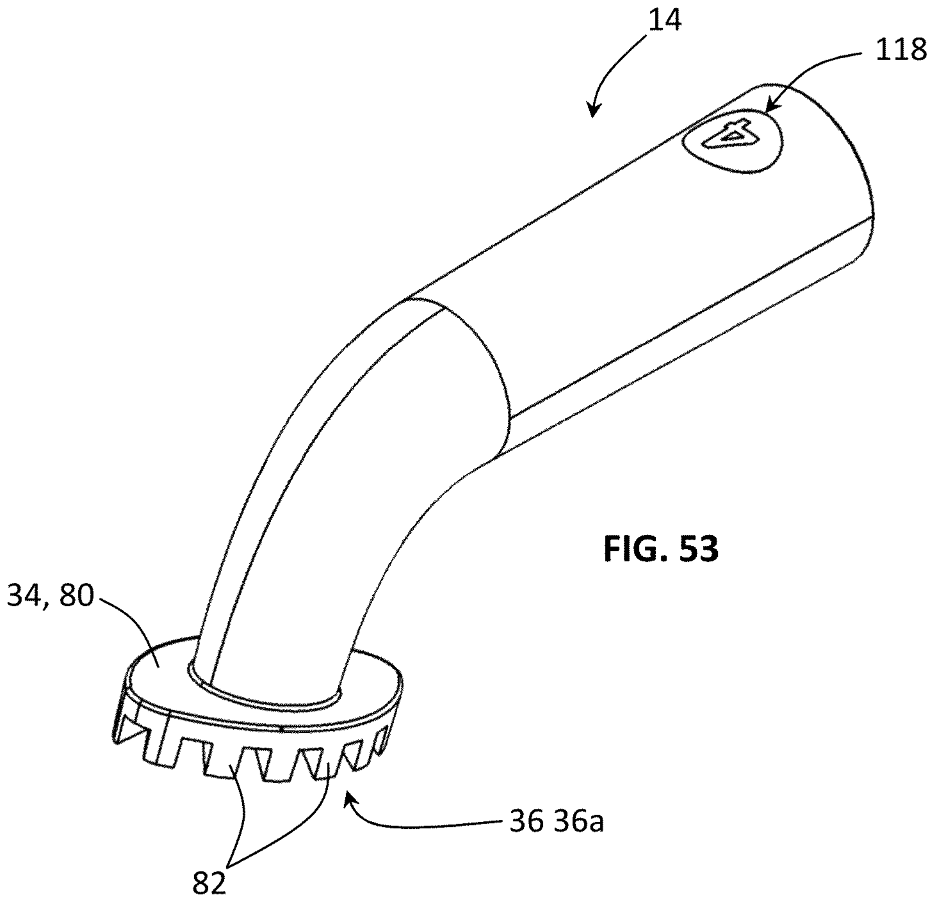
FIG. 53 is a perspective view of another alternative embodiment of a removable head for a wound-care device.
Figure 54:
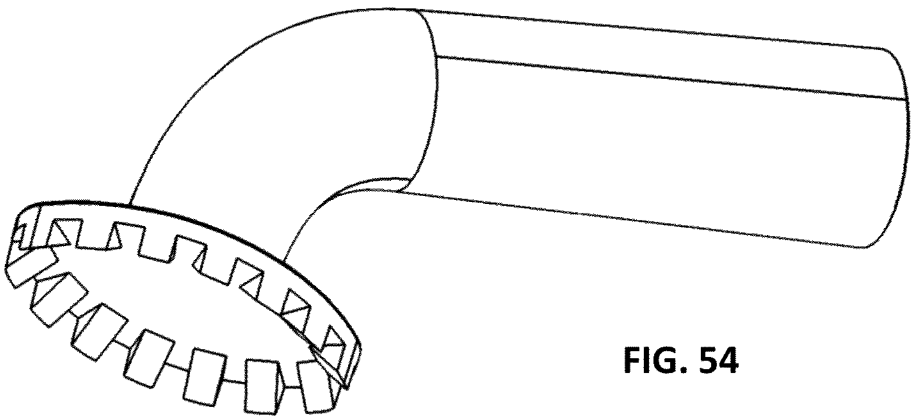
FIG. 54 is another perspective view of the removable head of FIG. 53.
Figure 59:
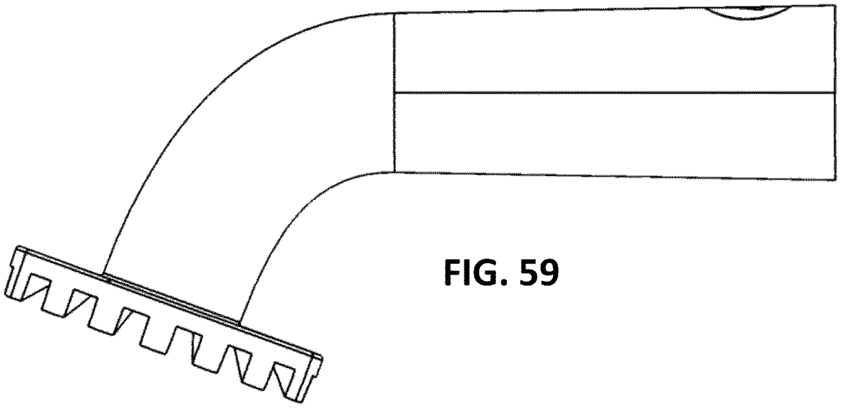
FIG. 59 is a first side view of the removable head device of FIG. 53.
Figure 60:
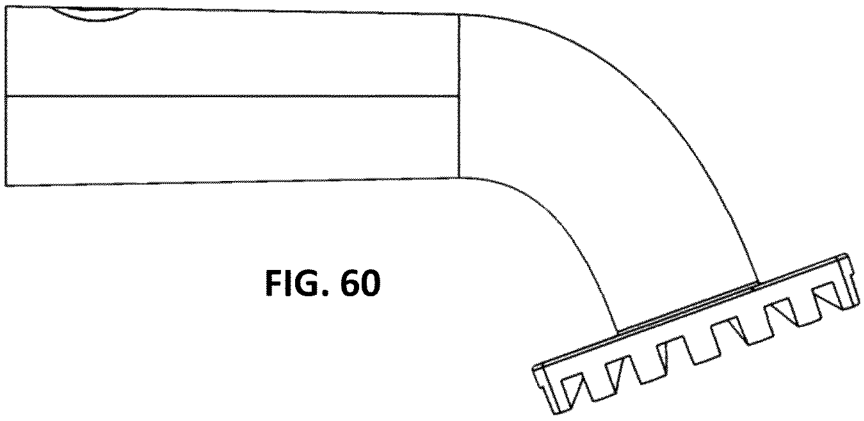
FIG. 60 is a second, opposite side view of the removable head of FIG. 53.
Figure 61:
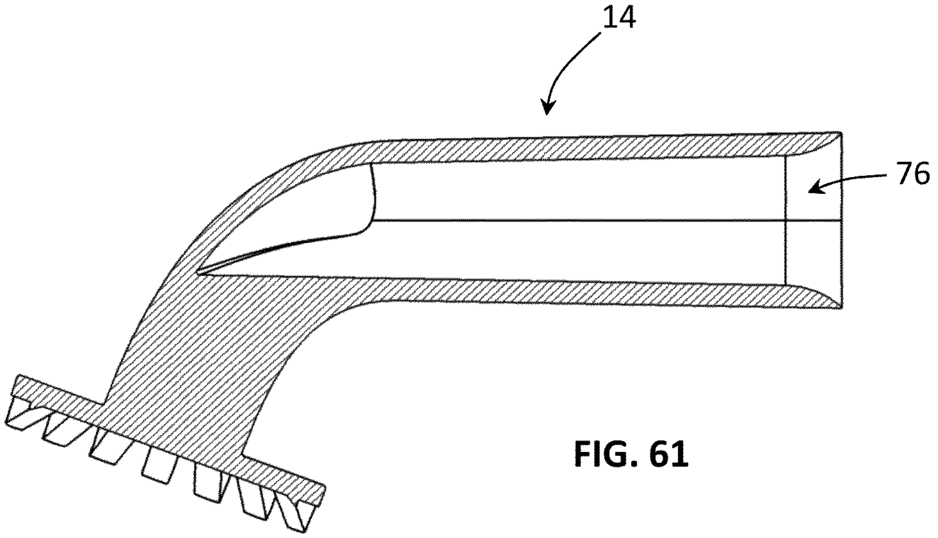
FIG. 61 is a side cross-sectional view of the removable head of FIG. 53.
Figure 62:
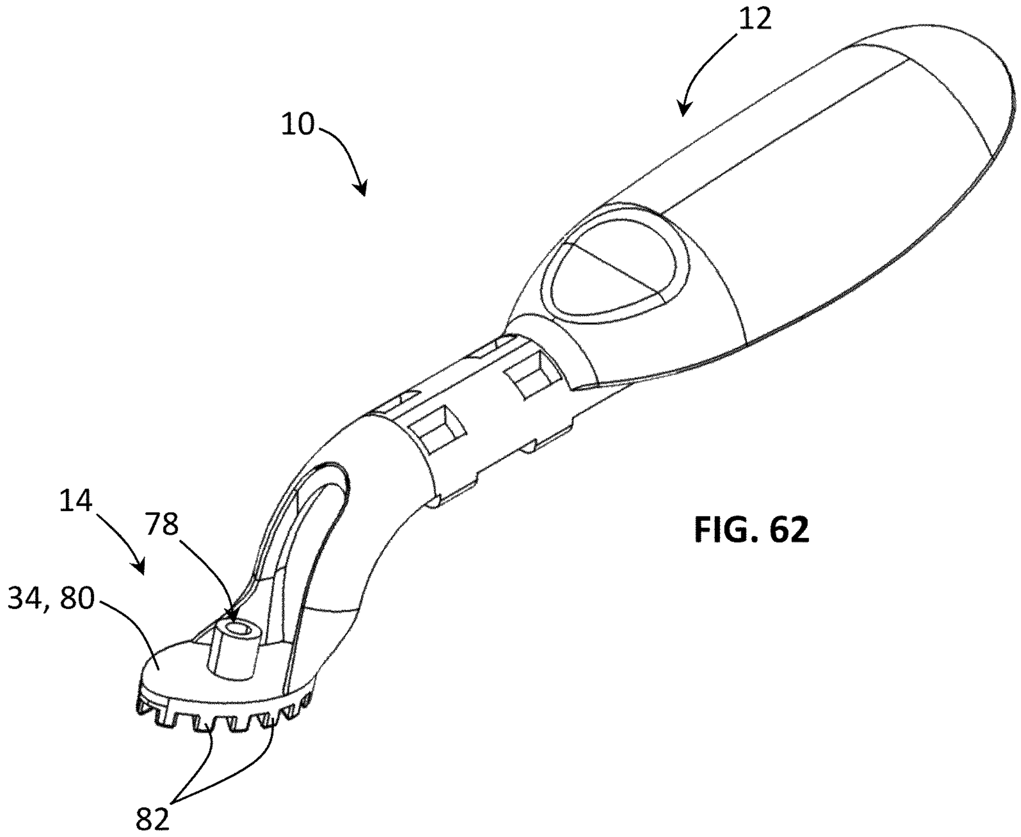
FIG. 62 is a perspective view of another alternative embodiment of a wound-care device.
Figure 63:
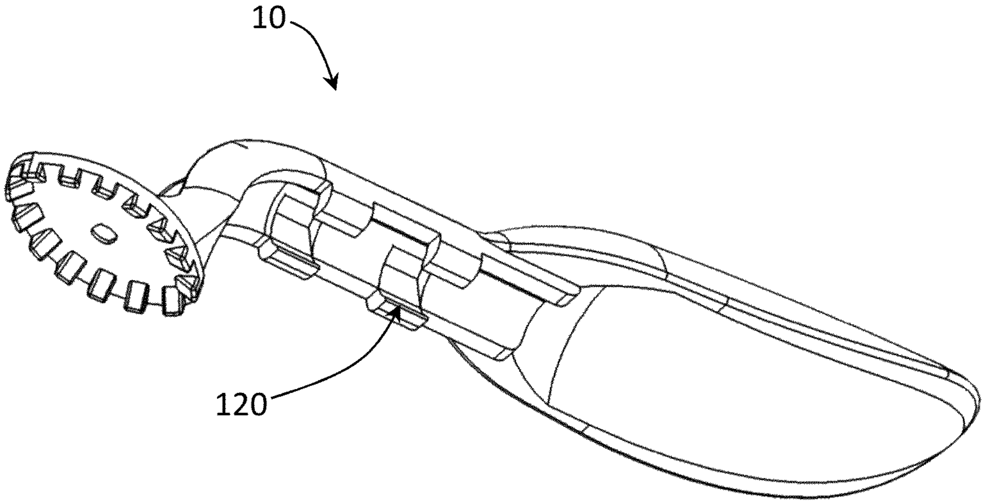
FIG. 63 is another perspective view the wound-care device of FIG. 62.
Figure 64:
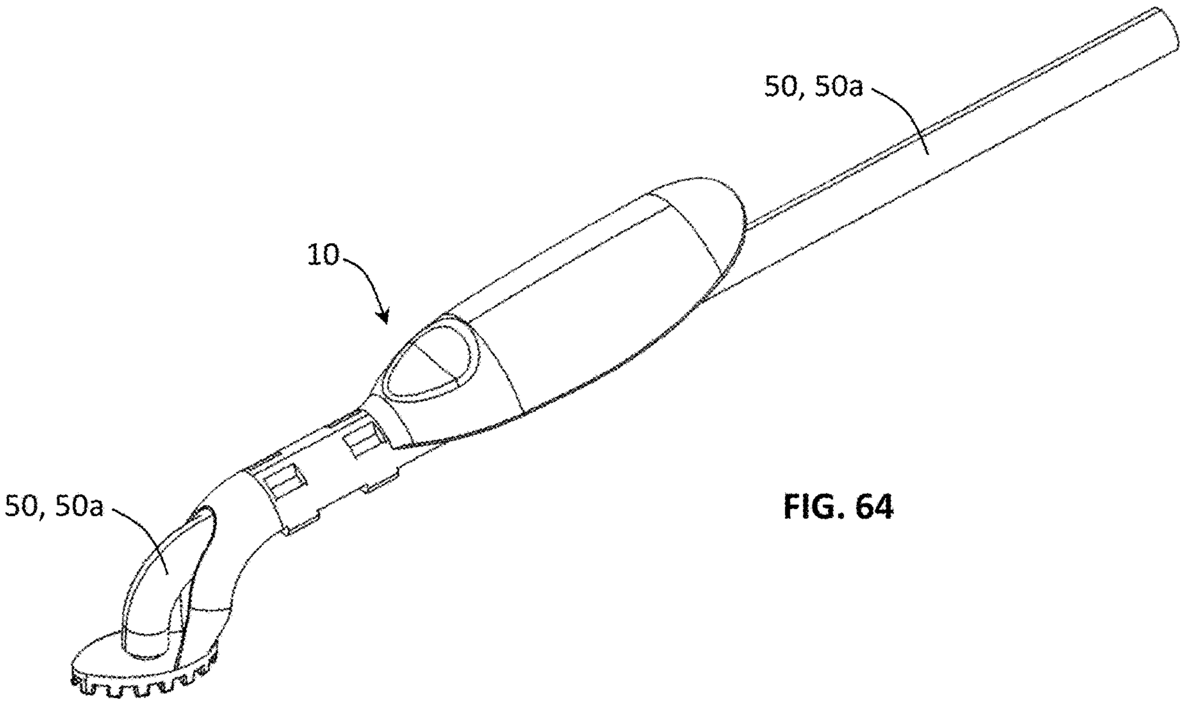
FIG. 64 is a perspective view the wound-care device of FIG. 62 with a tube applied thereto that may extend to a remote fluid reservoir.
Figure 65:
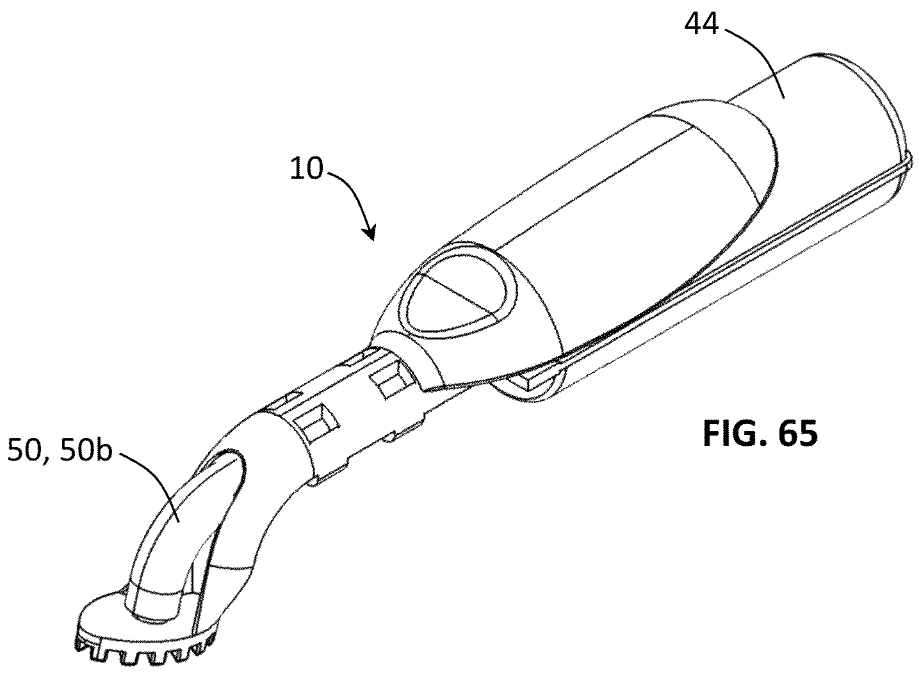
FIG. 65 is a perspective view the wound-care device of FIG. 62 with a fluid reservoir applied thereto.
Figure 66:
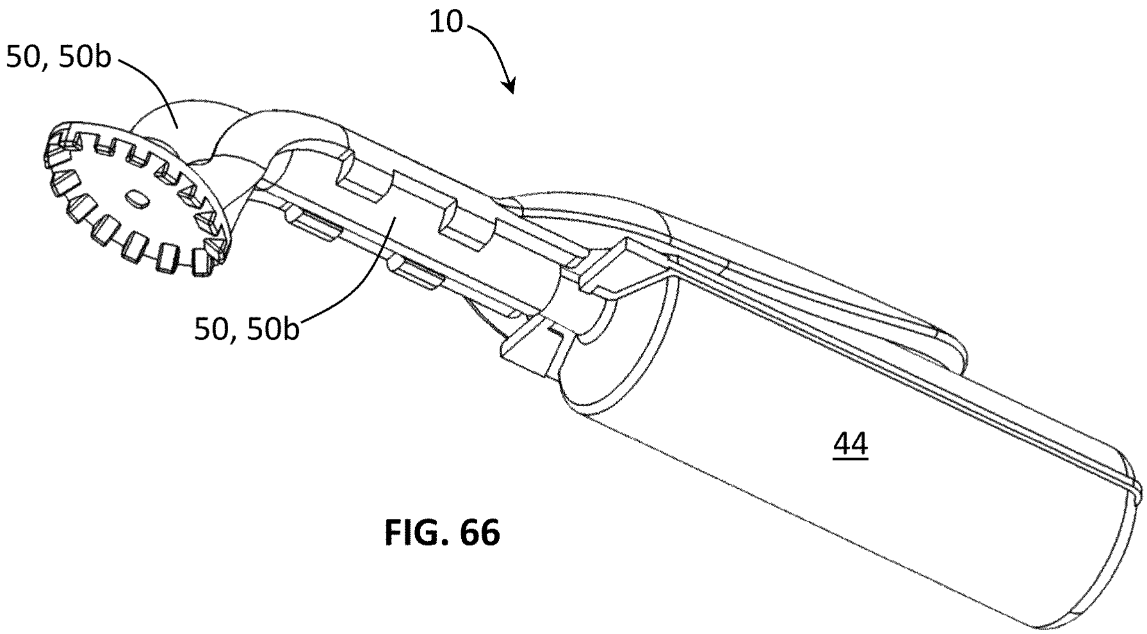
FIG. 66 is another perspective view the wound-care device of FIG. 62 with a fluid reservoir applied thereto.
Figure 67:
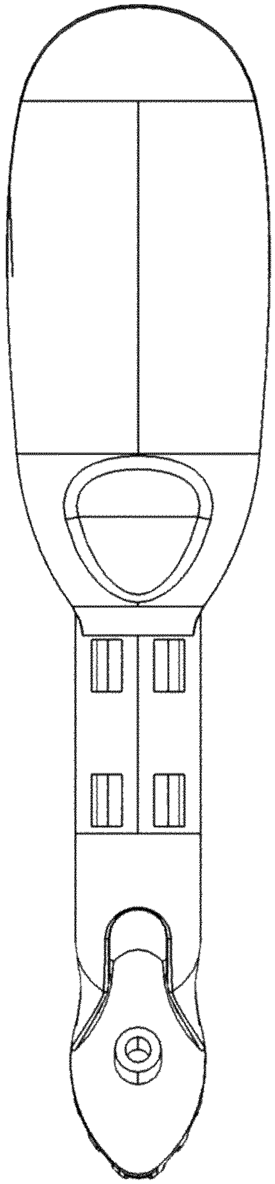
FIG. 67 is a top view of the wound-care device of FIG. 62.
Figure 68:
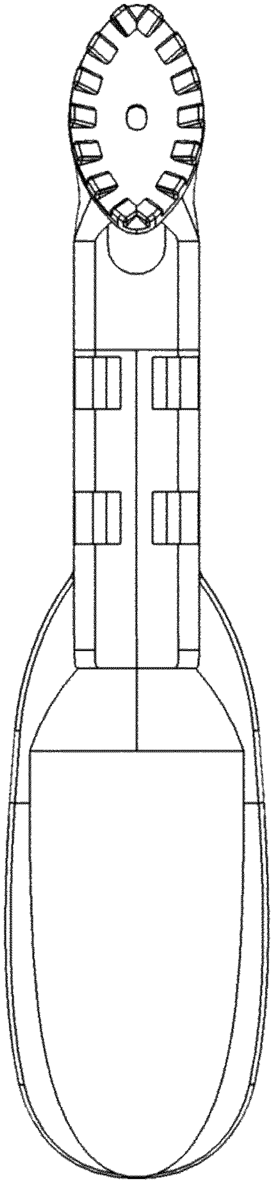
FIG. 68 is a bottom view of the wound-care device of FIG. 62.
Figure 69:
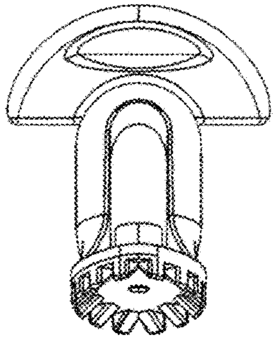
FIG. 69 is a front view of the wound-care device of FIG. 62.
Figure 70:
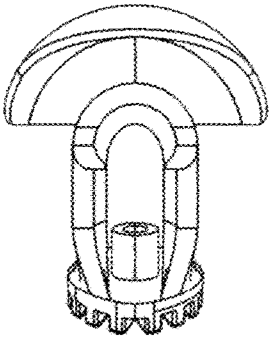
FIG. 70 is a rear view of the wound-care device of FIG. 62.
Figure 71:
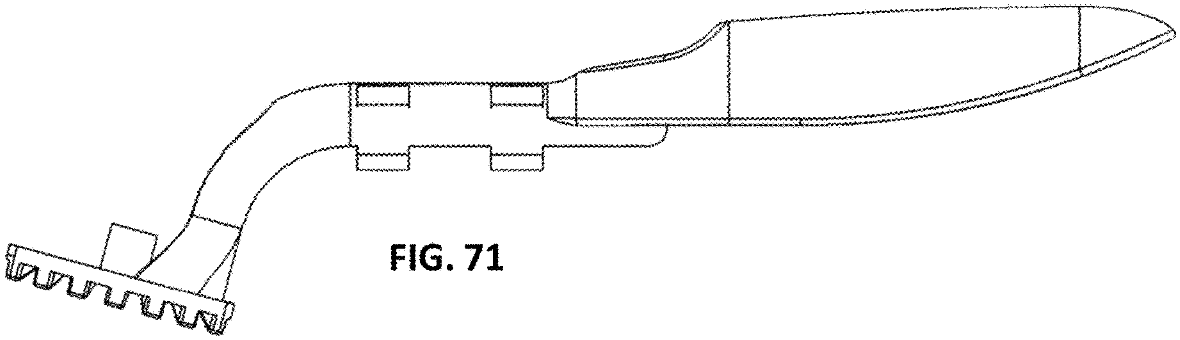
FIG. 71 is a first side view of the wound-care device of FIG. 62.
Figure 72:
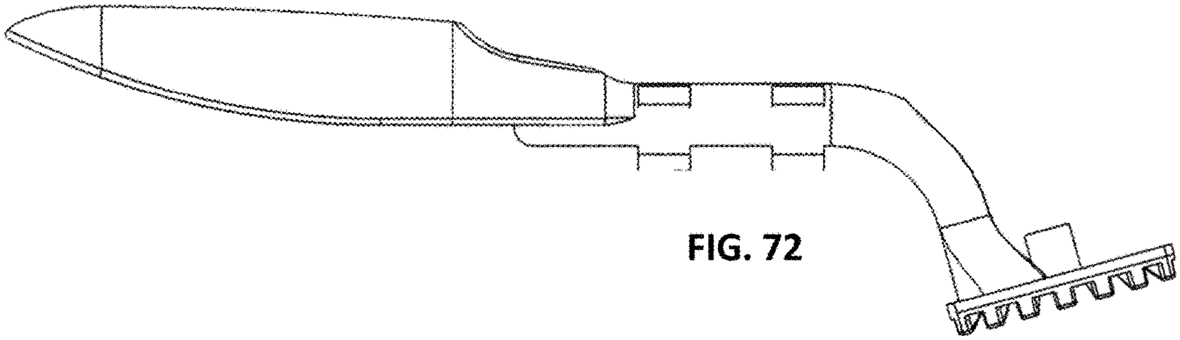
FIG. 72 is a second, opposite side view of the wound-care device of FIG. 62.
Figure 73:
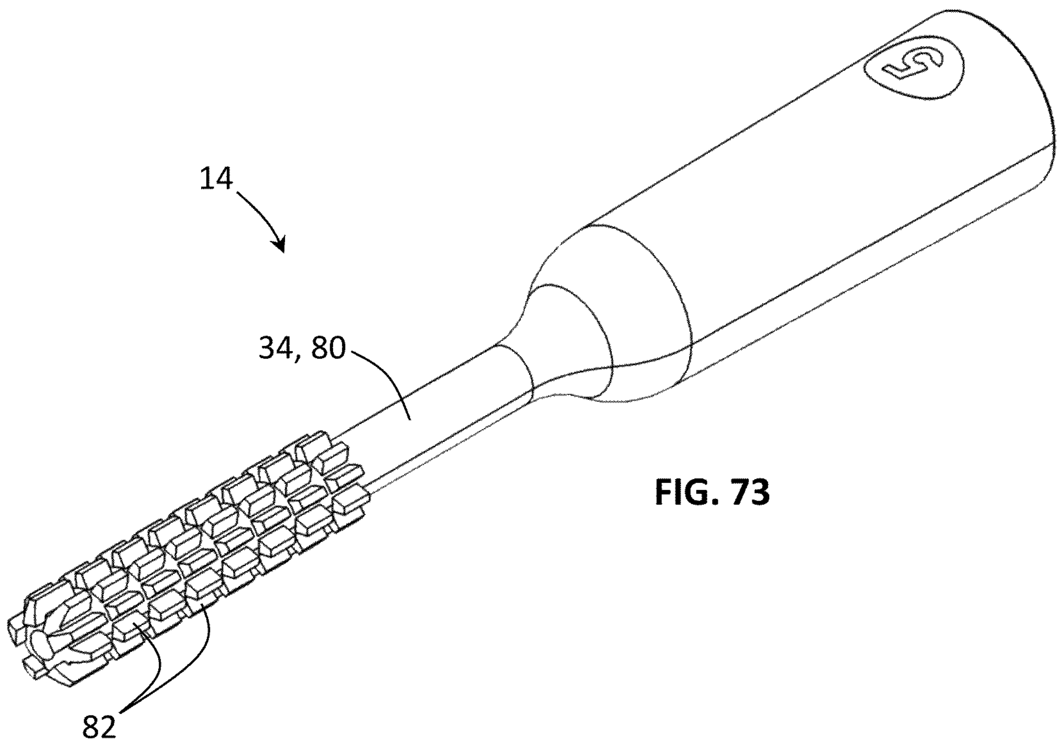
FIG. 73 is a perspective view of another alternative embodiment of a removable head for a wound-care device.
Figure 74:
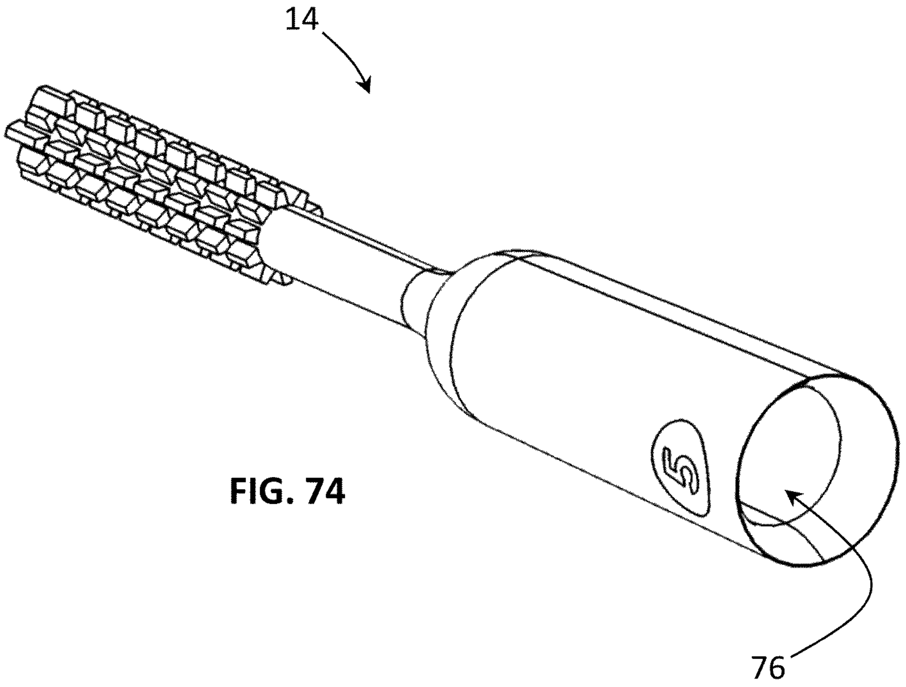
FIG. 74 is another perspective view of the removable head of FIG. 73.
Figure 75:
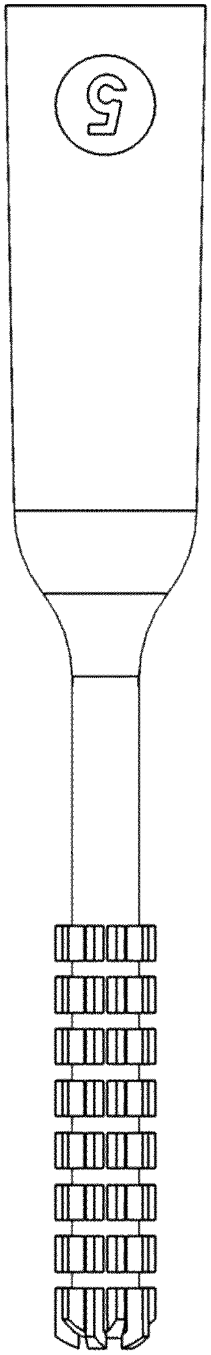
FIG. 75 is a top view of the removable head of FIG. 73.
Figure 76:
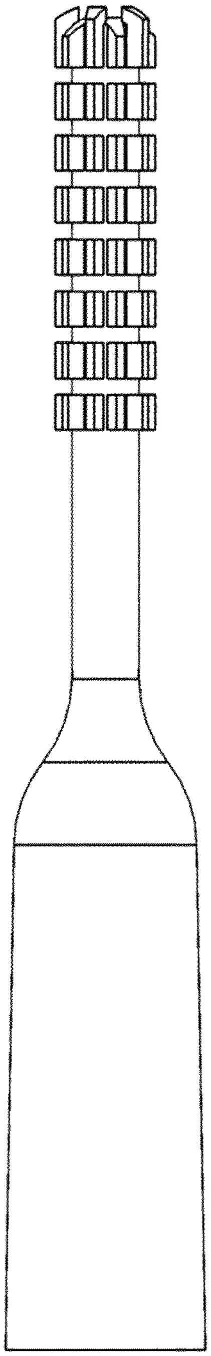
FIG. 76 is a bottom view of the removable head of FIG. 73.
Figure 77:
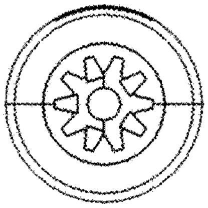
FIG. 77 is a front view of the removable head of FIG. 73.
Figure 78:
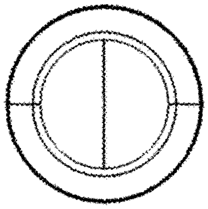
FIG. 78 is a rear view of the removable head device of FIG. 73.
Figure 79:
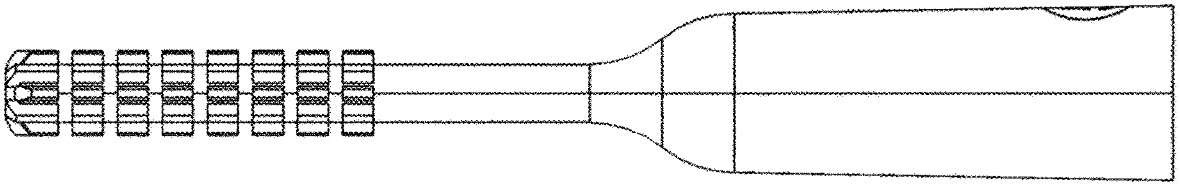
FIG. 79 is a first side view of the removable head device of FIG. 73.
Figure 80:
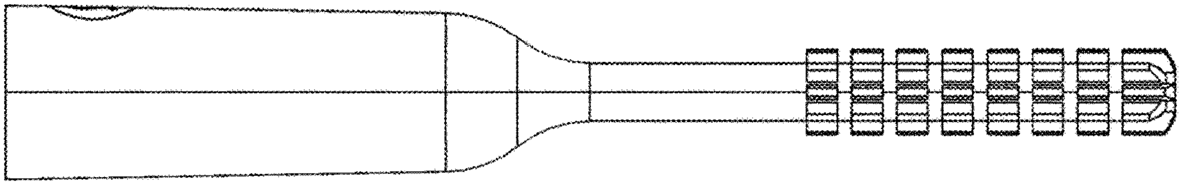
FIG. 80 is a second, opposite side view of the removable head of FIG. 73.
Figure 81:
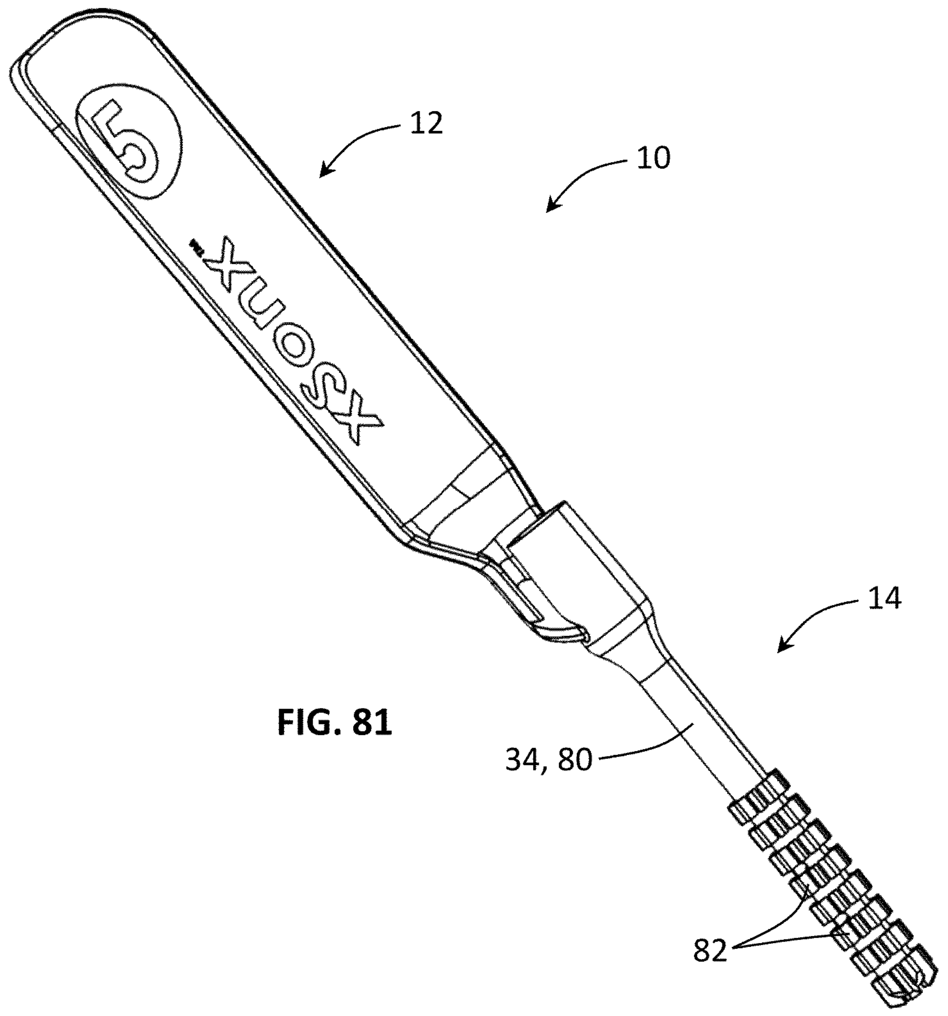
FIG. 81 is a perspective view of another alternative embodiment of a wound-care device.
Figure 82:
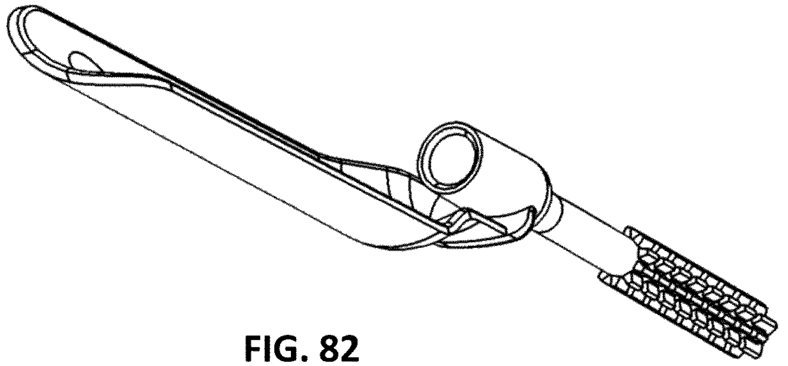
FIG. 82 is another perspective view of the removable head of FIG. 81.
Figure 83:
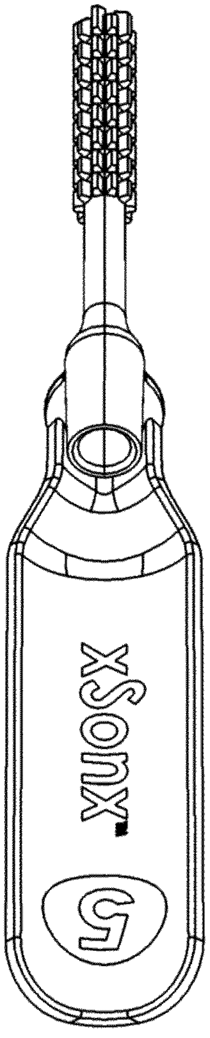
FIG. 83 is a top view of the wound-care device of FIG. 81.
Figure 84:
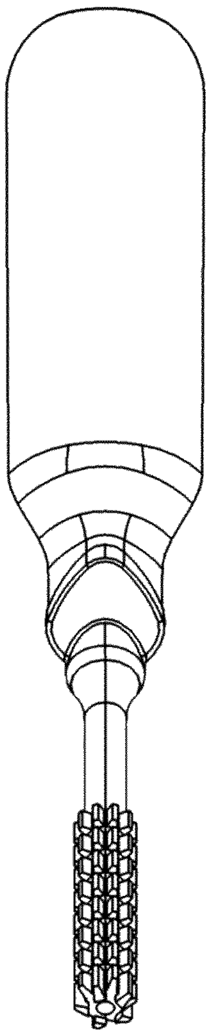
FIG. 84 is a bottom view of the wound-care device of FIG. 81.
Figure 85:
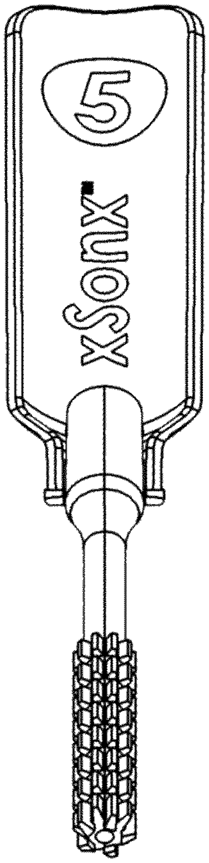
FIG. 85 is a front view of the wound-care device of FIG. 81.
Figure 86:
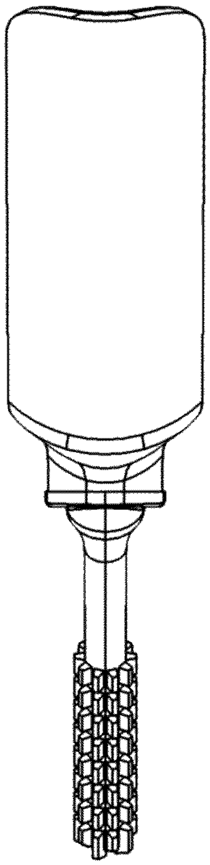
FIG. 86 is a rear view of the wound-care device of FIG. 81.
Figure 87:
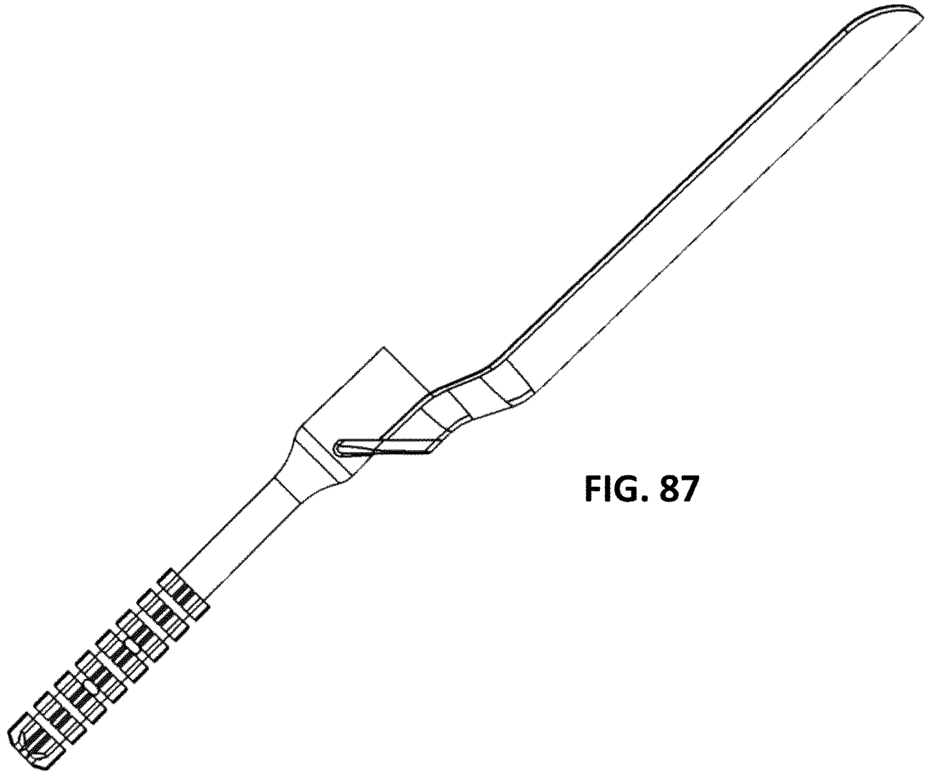
FIG. 87 is a first side view of the wound-care device of FIG. 81.
Figure 88:
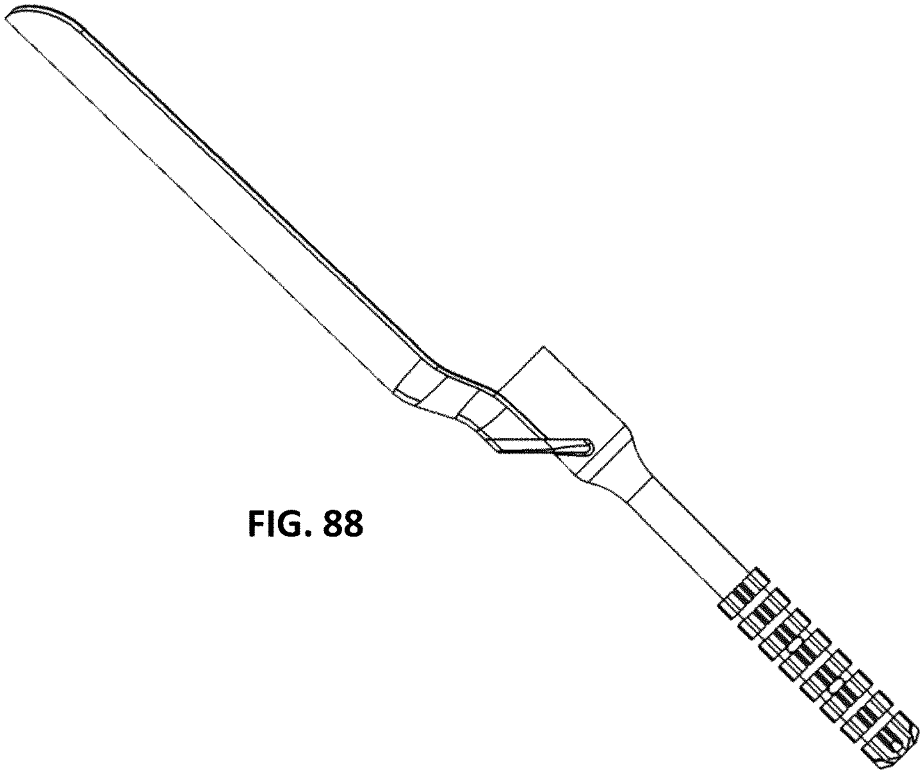
FIG. 88 is a second, opposite side view of the wound-care device of FIG. 81.

FIGS. 28-31 show one embodiment of a main body 12 that is simplified and head 14 combination where the head 14 includes (e.g., is monolithically formed or molded to have) a debridement surface 36*a*. In selected embodiments, the extensions 82 of a contact surface 36 (e.g., a debridement surface 36*a*) may alternate in height or be laterally offset side to side. For example, as shown in FIG. 28, the two distal most and two proximal most instances of the extensions 82 may be oriented so that the highest portion thereof is positioned to the outside for better cutting at the apices of the head 14, but the extensions 82 may otherwise alternate to make a broader cutting path.

Referring to FIGS. 32-38, in selected embodiments, a main body 12 and head 14 combination that is simplified may be formed without an aperture 78 for fluid to pass through the head 14. Rather, the combination may include one or more ribs 114 that extend to connect and/or reinforce a base 80 of a head 14 with respect to a main body 12 or handle portion. In certain embodiments, one or more ribs 114 may include proximal ends 102 having a curvature 106 formed therein that follows or replicates a portion of the curvature of a fingertip. Accordingly, one or more ribs 114 may be configured to engage a tip of a finger of a user.

In selected embodiments, a head 14 may include a base 80 without any extensions 82 projecting therefrom. For example, as shown in FIG. 32-38, a front side 40 of a base 80 may be substantially flat. Such a flat surface may provide a location for adhering a contact surface 36 comprising a scrubbing pad (e.g., open cell foam, closed cell foam, soft silicone, or other semi-abrasive surface). Alternatively, a base 80 may provide a location or structure to which a contact surface 36 that is appropriate may be fastened, snapped, slid over both ends of the base 80, or otherwise secured to a head 14. A main body 12 may, therefore, be provided in a non-sterile condition and still be safely used when a contact surface 36 that is sterile is secured in place. Accordingly, in such embodiments, a contact surface 36 may comprise or be formed by a scrubbing pad or the like of a material that is dissimilar to a material forming a head 14 or a head 14 and main body 12.

Referring to FIGS. 39-45, in selected embodiments, a main body 12 that is simplified and head 14 combination may be formed with a base 80 that includes a wedge 116, ramp, crescent, or the like that provides an abutment for a fingertip of a user. Accordingly, there are various ways in which a base 80 may be configured to engage a tip of a finger of a user.

Referring to FIGS. 46-52, an alternative embodiment of a main body 12 that is simplified and head 14 combination is illustrated. As shown, a head 14 may include (e.g., may be monolithically formed or molded to have) a debridement surface 36*a*. In selected embodiments, the extensions 82 of a contact surface 36 (e.g., a debridement surface 36*a*) may face outside (i.e., have a highest portion along an outside edge) so that the outer edge of the head 14 may better engage and cut into tissue in need of debridement. Additionally, a head 14 may be manipulated as it engages a wound bed to pull the head 14 along an outer edge thereof, thereby making a more sharply debrided wound edge as may be desired by a medical professional using the wound-care device 10 or supervising use thereof. For example, a head 14 may be manipulated in a carving motion along the edges thereof, thereby giving the medical professional maximal control over the aggressiveness of the debridement obtained during the procedure.

In selected embodiments, a wound-care device 10 (e.g., a main body 12 and/or a head 14) in accordance with the present may have a number 118, letter, marking, symbol, color code, or the like applied thereto that is indicative of where a contact surface 36 corresponding thereto falls on an aggressiveness scale. For example, on a number scale from one to four, a number one may indicate a cleansing surface 36*c* or some other contact surface 36 that is least aggressive, while a number four may indicate a debridement surface 36*a* that is sharp or some other contact surface 36 that is most aggressive. Accordingly, a medical professional or other user may refer to a number 118 or the like when selecting a wound-care device 10 for use.

Referring to FIGS. 53-61, in selected embodiments, an aperture 78 may be omitted from a removeable version of a head 14 of a wound-care device 10. In such embodiments, a frame 34 of the head 14 may still include an aperture 76 to support securement to a main body 12. Such an aperture 76 may be shaped and sized to selectively receive a physical linkage, horn 28, or the like that conducts vibration, oscillation, and/or reciprocation from a main body 12 to a head 14.

Referring to FIGS. 62-72, in selected embodiments, a fluid system 16 may be separated from (e.g., located somewhat remotely with respect to) a main body 12 and/or head 14. For example, a fluid system 16 may comprise a pump (e.g., a peristaltic pump) that draws fluid from a fluid reservoir 44 (e.g., a saline bag) and urges the fluid through a conduit 50*a* that is relatively long to an aperture 78 in a head 14. In this manner, the flow of liquid to head 14 may be controlled (e.g., finely controlled) and may be set to a relatively low flow rate so as to avoid creating a puddling, liquid control, or liquid absorption problem for a user and/or patient. In such embodiments, a main body 12 may provide a channel 120 for receiving and engaging the conduit 50*a*. The channel 120 may grip the conduit 50*a* and ensure that the conduit 50*a* moves with the main body 12 and is not inadvertently pulled away or disengaged from a head 14.

In certain embodiments, a main body 12 and/or head 14 configured for use with a fluid reservoir 44 that is located remotely may also be configured for use with an on-board or attached fluid reservoir 44. For example, a main body 12 may be shaped to house, extend over, or cradle at least a portion of a fluid reservoir 44 (e.g., at least a portion of a saline bullet). In such arrangements, a channel 120 may receive and secure a relatively short conduit 50*b*. Insertion of an outlet 88 of a fluid reservoir 44 into one end of the relatively short conduit 50*b* may secure or connect the fluid reservoir 44 to the rest of the wound-care device 10.

Referring to FIGS. 73-88, in selected embodiments, a head 14 may be configured for use on an open, deep wound or in undermined areas or tunneling wound-care situations. Accordingly, a contact surface 36 and frame 34 for such embodiments may be sized, shaped, and of sufficient length to support or facilitate that function. In certain embodiments, such a "deep pocket" head 14 may have an aperture 76 to support securement to a main body 12. Such an aperture 76 may be shaped and sized to selectively receive a physical linkage, horn 28, or the like that conducts vibration, oscillation, and/or reciprocation from a main body 12 to a head 14. In other embodiments, a head 14 for use on a deep pocket may be monolithically connected to (e.g., molded as a single unit with) a main body 12 or handle portion that is shaped to cradle a finger of a user or fluid reservoir 44 as described hereinabove.

Figure 89:
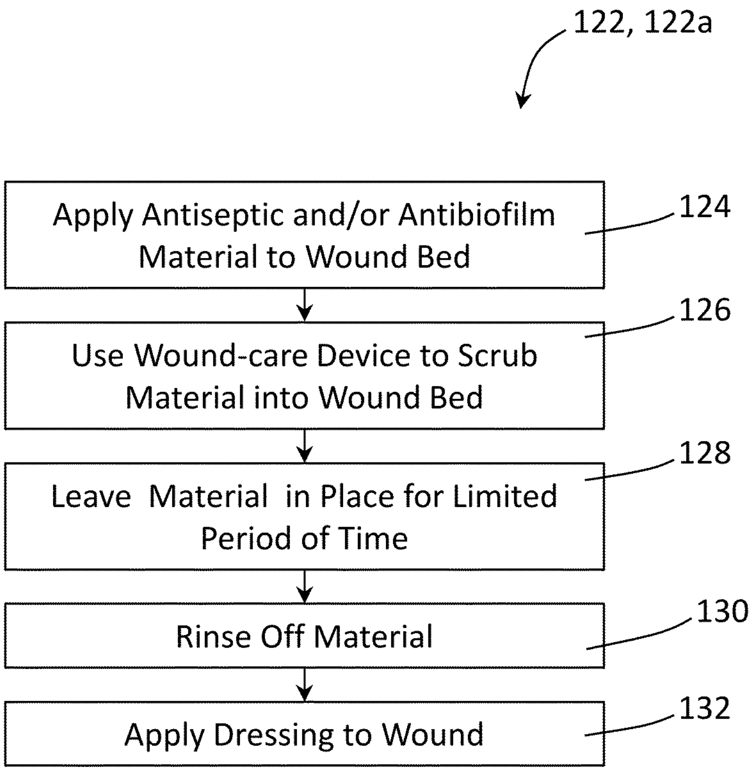
FIG. 89 is a block diagram of an alternative embodiment of a method for using a wound-care device.
Figure 90:
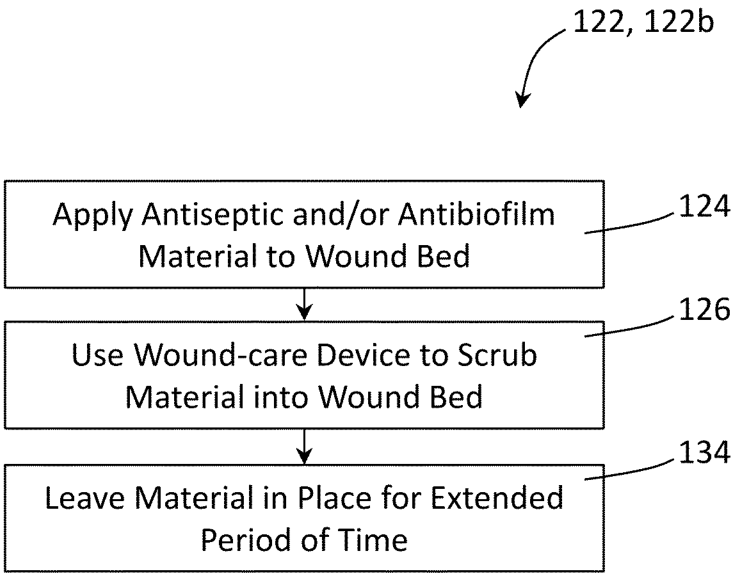
FIG. 90 is a block diagram of another alternative embodiment of a method for using a wound-care device.

Referring to FIGS. 89 and 90, in selected embodiments, a wound-care device 10 may be used in alternative methods 122. Alternative methods 122 may be performed as standalone methods of wound care or may be incorporated into one or more other methods set forth hereinabove (e.g., after it is determined 72 that the cleansing, desloughing, and/or debriding is complete in the first method 58 of FIG. 5, in the second method 108 of FIG. 15, in the third method 112 of FIG. 16, or the like). In certain embodiments, one or more alternative methods 122 may involve applying an antiseptic and/or antibiofilm gel, paste, powder, or the like to a wound bed. This may assist in physically breaking up any biofilm (e.g., disrupt the Extra Polymeric Substance (EPS) of the biofilm) while, at the same time, actively working to (1) expose, lift up, flush away, and/or kill bacteria, and/or (2) otherwise chemically disrupt the biofilm.

For example, in first alternative method 122*a*, an antiseptic and/or antibiofilm material (e.g., gel, paste, powder, or the like) may be applied 124 to a wound bed. Thereafter, a wound-care device 10 may be used to scrub 126 the material into the wound bed. The material may be left 128 in place for a limited period of time (e.g., a time period in a range from about 1 minute to about 15 minutes) and then rinsed 130 off. Thereafter, a dressing may be applied 132 if desired or necessary.

If an antiseptic and/or antibiofilm material is of a nature that prolonged application or exposure to a wound bed is beneficial and not potentially harmful, a second alternative method 122*b* may be used. Specifically, after the material is applied 124 and scrubbed 126, it may be left 134 in place for an extended period of time. For example, a material may be left 134 in place for hours to days (e.g., up to seven days) in the case of an acutely infected wound. Accordingly, an antiseptic and/or antibiofilm material may affirmatively act to prevent bacterial growth, biofilm regrowth, and to provide an appropriate moist wound healing environment for an extended period of time.

In selected embodiments, an example of an antiseptic and/or antibiofilm material that may be rinsed 130 off after a few minutes may be hypochlorous acid, iodine, polyhexamethylene biguanide (PHMB), or the like. In certain embodiments, a preferred material may combine one or more antiseptics and/or antibiotics with one or more surfactants. Surfactants may break down the protective outer layer(s) of bacteria and/or viruses, kill bacteria or viruses, bind to dead or living bacteria and lift them off a wound bed, or the like. Therefore, one or more surfactants may be a valuable contributor to a gel, paste, power, or the like applied to a wound bed in one or more methods (e.g., a first method 58, second method 108, third method 112, or alternative method 122).

Ethylenediaminetetraacetic acid (EDTA) is a metal chelator that may help break up biofilm and work well when combined with one or more surfactants. Adding EDTA to a combination of antiseptics such as iodine and PHMB may produce or enable a liquid material (e.g., an emulsified gel) suitable for application to a wound bed in one or more methods such as a first method 58, second method 108, third method 112, or alternative method 122 (i.e., when combined with a manual and/or low sonic frequency electromechanical manipulation of a wound bed using a wound-care device 10).

An example of an antiseptic and/or antibiofilm material that may be left 134 in place for an extended period of time may be a slow-release iodine dressing, a PHMB dressing, or a combination or sub-combination of iodine, PHMB, EDTA, one or more surfactants, and the like. If such a combination is made in the context of a viscous gel or paste, it may be applied to a contact surface 36 of a head 14 and then scrubbed into a wound bed to break up biofilm bacteria and EPS and kill the bacteria.

Figure 91:
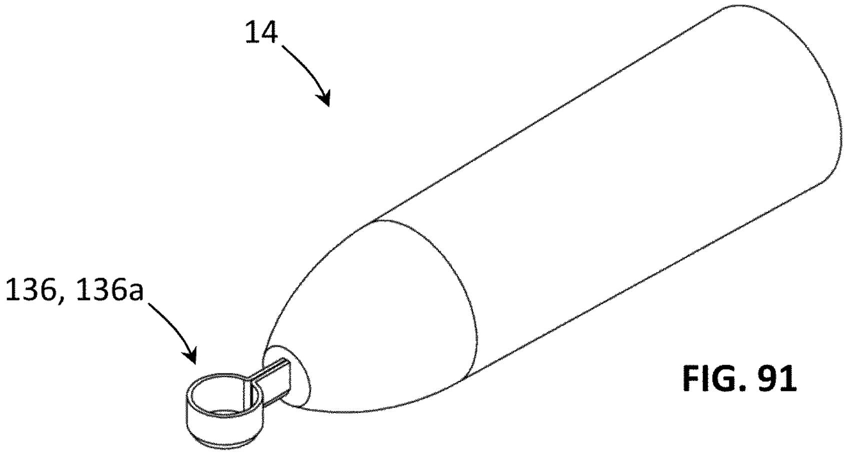
FIG. 91 is a perspective view of another alternative embodiment of a removable head for a wound-care device.
Figure 92:
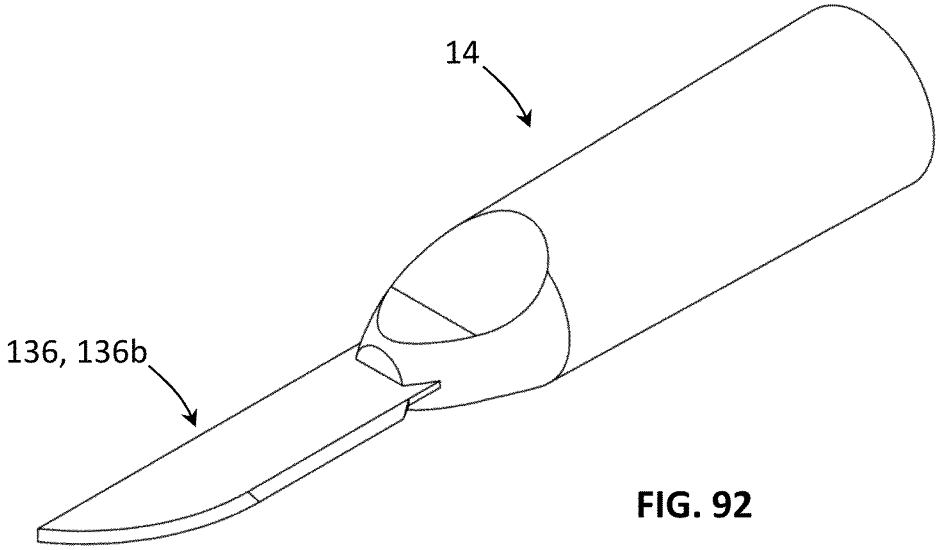
FIG. 92 is a perspective view of another alternative embodiment of a removable head for a wound-care device.

Referring to FIGS. 91 and 92, in selected embodiments, one or more heads 14 may include a cutting element 136 (e.g., a curette 136*a*, scalpel 136*b*, or the like) rather than a contact surface 36. For example, a head 14 may configured as a removable version having an aperture 76 for receiving a horn 28 or the like therewithin. Accordingly, when such a head 14 is applied to a horn 28 and the wound-care device 10 corresponding thereto is turned "on," a motion generator 18 may cause a cutting element 136 to vibrate, oscillate, and/or reciprocate at a desired frequency. This motion may enable a user to remove dead tissue, callous material, or the like more easily or in a more controlled manner.

In view of the foregoing, a wound-care device 10 may be supplied with or simply fit a variety of heads 14 that are different (e.g., be supplied with or fit one or more heads 14 for cleansing, one or more heads 14 for desloughing, one or more heads 14 for debriding, one or more heads 14 for cutting, or the like or a combination or sub-combination thereof). Accordingly, a user may select and install a head 14 to perform a particular task. When that task is complete, the user may remove that head 14 and install a head 14 that is different to perform a different task.

Figure 93:
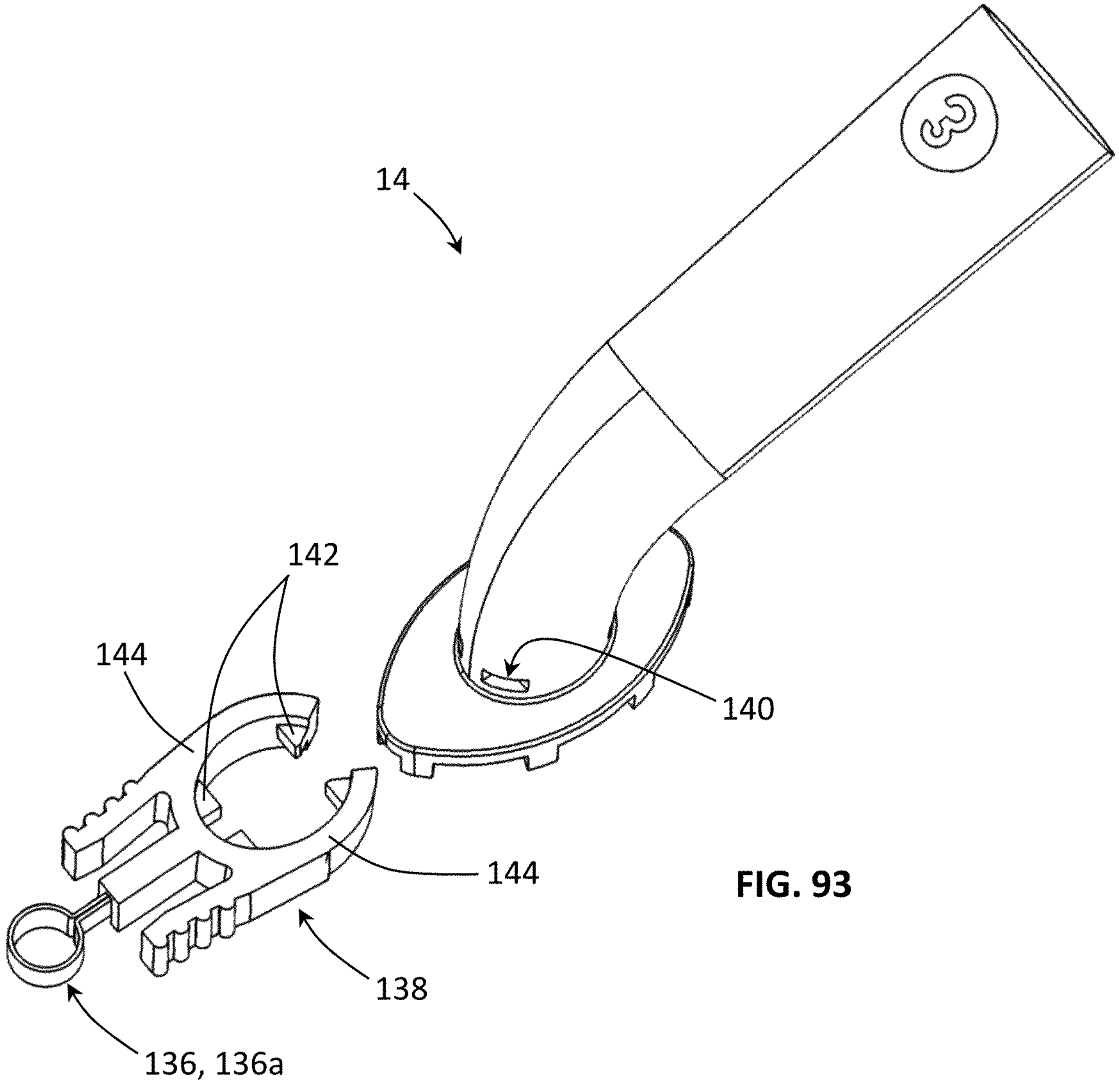
FIG. 93 is an exploded perspective view of another alternative embodiment of a removable head for a wound-care device.
Figure 94:
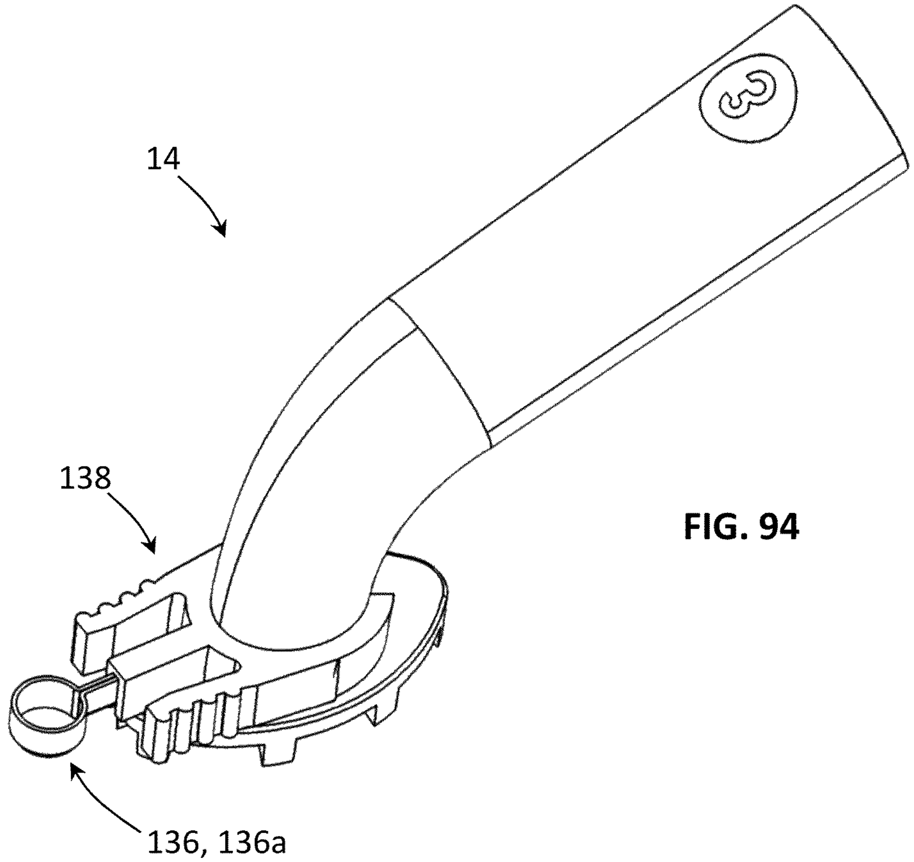
FIG. 94 is a perspective view of the removable head of FIG. 93 in an assembled configuration.
Figure 95:
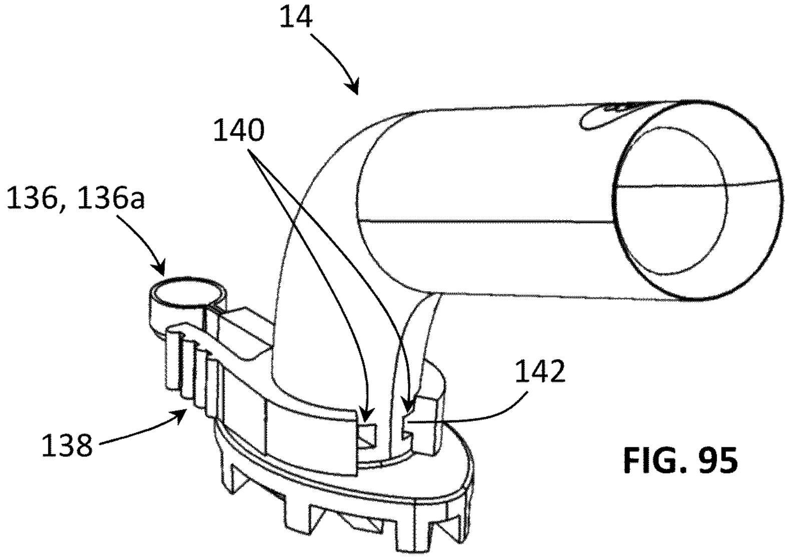
FIG. 95 is another perspective view of the removable head of FIG. 93 in an assembled configuration.
Figure 96:
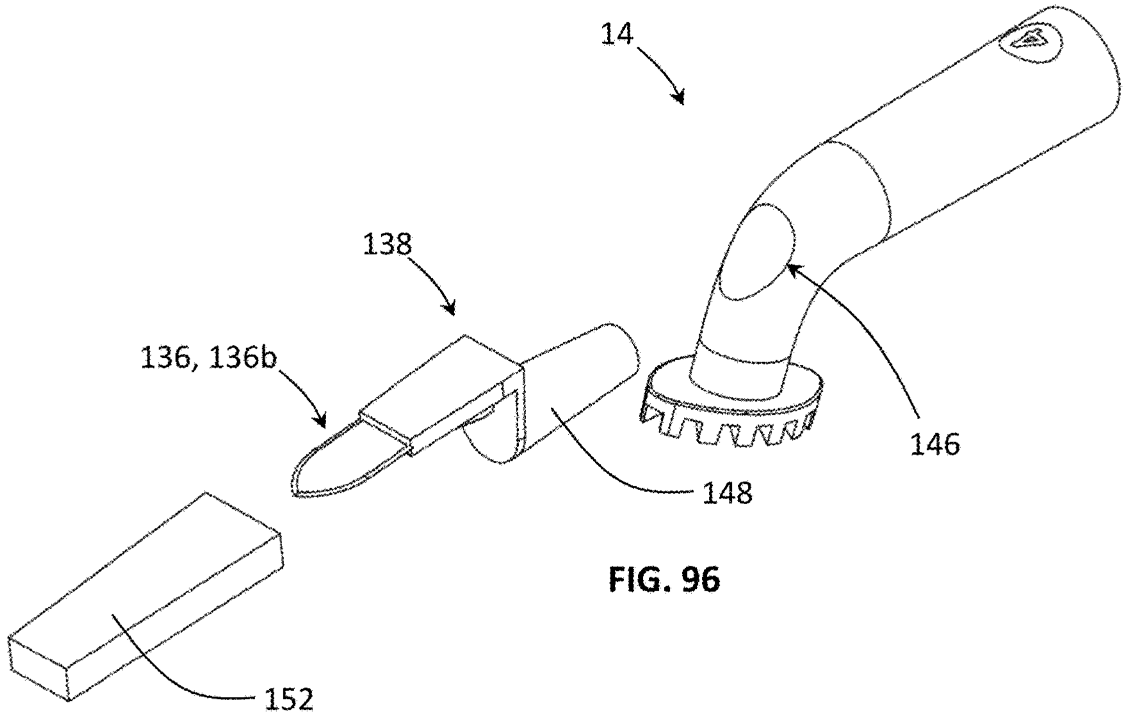
FIG. 96 is an exploded perspective view of another alternative embodiment of a removable head for a wound-care device.
Figure 97:
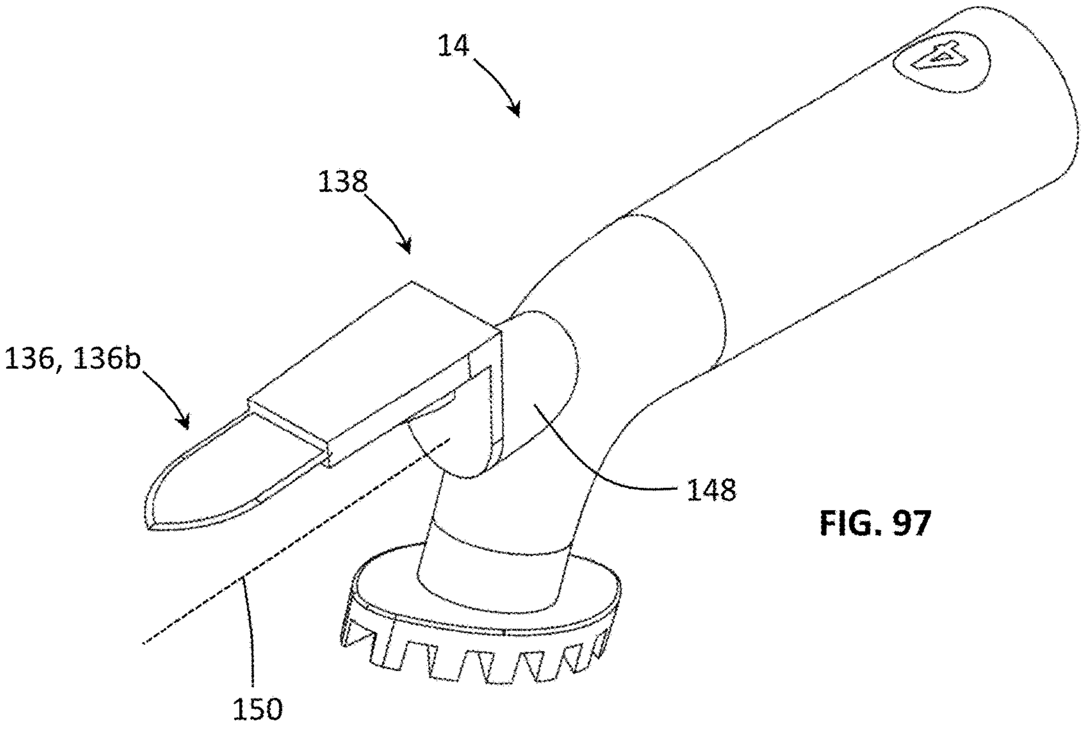
FIG. 97 is a perspective view of the removable head of FIG. 96 in an assembled configuration with the protective cover removed.
Figure 98:
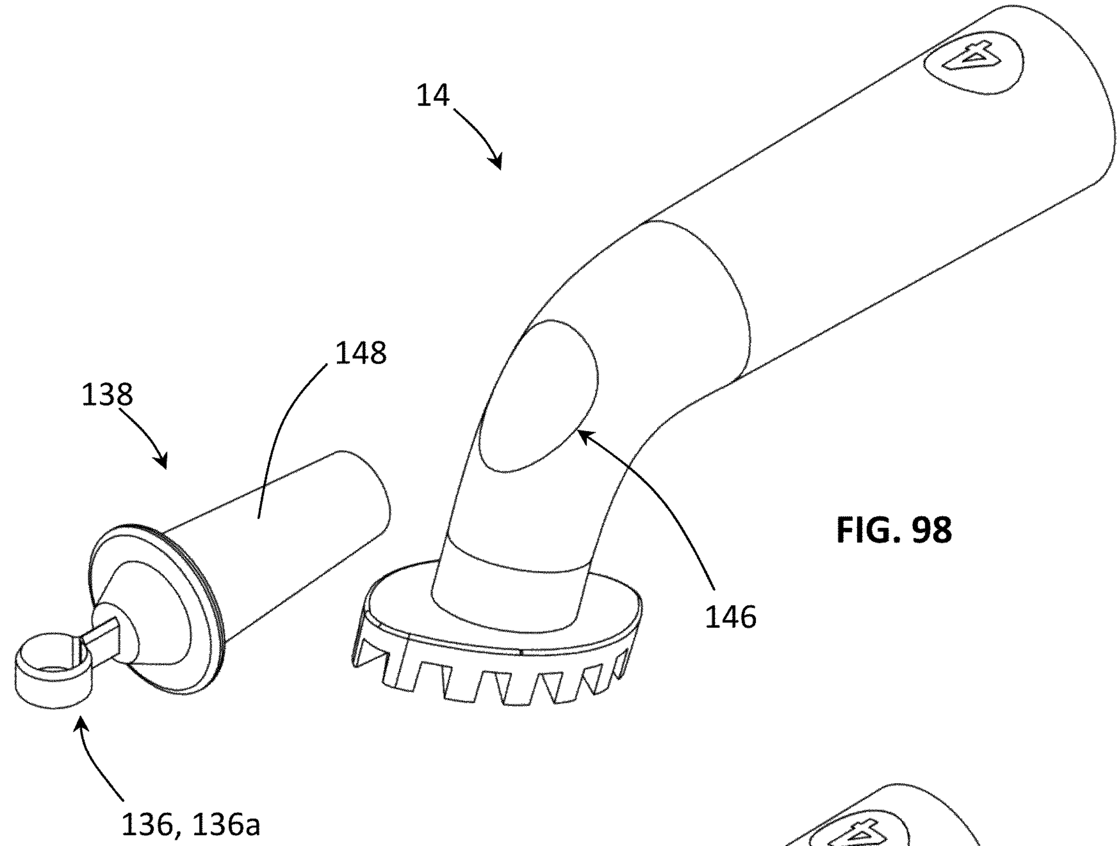
FIG. 98 is an exploded perspective view of another alternative embodiment of a removable head for a wound-care device.
Figure 99:
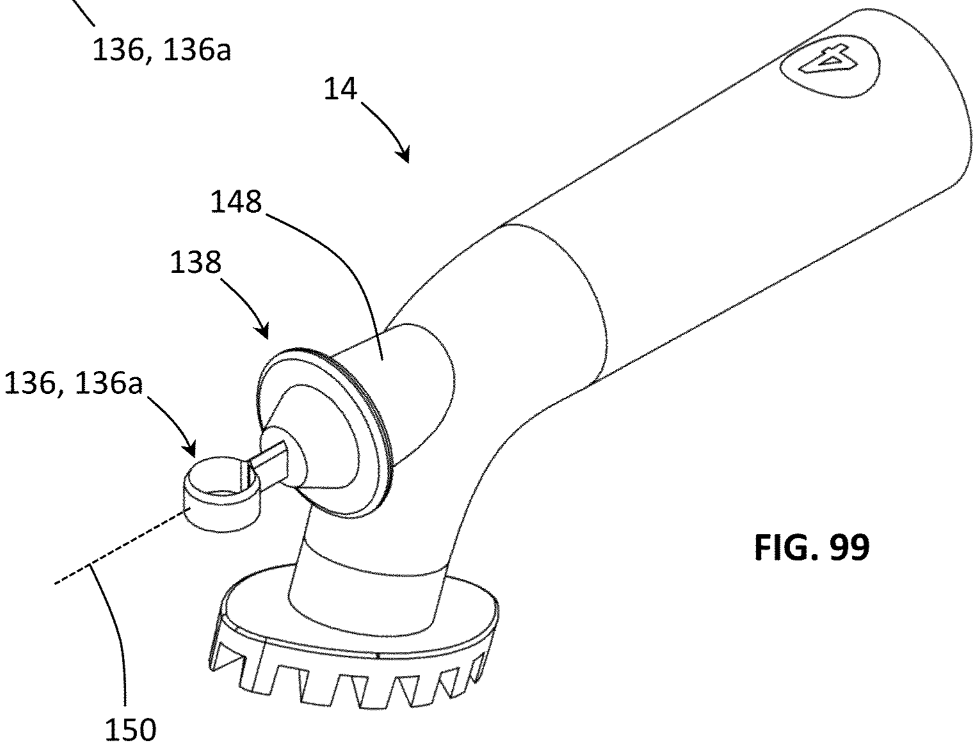
FIG. 99 is a perspective view of the removable head of FIG. 98 in an assembled configuration.

Referring to FIGS. 93-95, in selected embodiments, one or more heads 14 may include a cutting element 136 (e.g., a curette 136*a*, scalpel 136*b*, or the like) in addition to a contact surface 36. For example, a head 14 may configured to receive and retain a cutting element 136 that is removable. Accordingly, when such a head 14 is applied to a horn 28 and the wound-care device 10 corresponding thereto is turned "on," a motion generator 18 may cause a cutting element 136 that is removable to vibrate, oscillate, and/or reciprocate at a desired frequency.

In selected embodiments, an engagement mechanism 138 may selectively and/or removably secure a cutting element 136 to the rest of a head 14. For example, a main portion of a head 14 may include one or more recesses 140 and an engagement mechanism 138 may include one or more extensions 142 shaped to engage the one or more recesses 140. Clamping "jaws" 144 or the like may be manually flexed to open an engagement mechanism 138 sufficiently that it may engage the rest of a head 14 (e.g., sufficiently that one or more extensions 142 may be positioned so as to align with one or more recesses 140). When manual flexing of the engagement mechanism 138 ends, the engagement mechanism 138 may return to a closed position wherein the clamping jaws 144 thereof are in a neutral and/or undeflected position. The tendency of an engagement mechanism 138 to remain in the closed position may hold the one or more extensions 142 within the one or more recesses 140 and, thereby, selectively and/or removably secure the cutting element 136 to the rest of the head 14.

Referring to FIGS. 96-99, in selected embodiments, an engagement mechanism 138 may selectively and/or removably secure within a tapered aperture 146 formed in a main portion of a head 14. For example, a main portion of a head 14 may include a tapered aperture 146 and an engagement mechanism 138 may include a tapered shaft 148 shaped to engage the tapered aperture 146. A frictional engagement between a tapered aperture 146 and a tapered shaft 148 of an engagement mechanism 138 may be sufficient to secure a cutting element 136 to the rest of a head 14.

In certain embodiments, an axis of symmetry 150 may exist between a tapered shaft 148 and a tapered aperture 146. Accordingly, before inserting an engagement mechanism 138 into a tapered aperture 146 of a head 14, a user may select a desired orientation for the cutting element 136 corresponding thereto. Once the orientation is selected and the tapered shaft 148 is seated within the tapered aperture 146, a friction engagement between the tapered aperture 146 and the tapered shaft 148 may resist relative rotation of one with respect to the other about the axis of symmetry 150.

In selected embodiments, a kit or system may include a removable cover 152 for a cutting element 136. A removable cover 152 may protect a user and/or patient from inadvertent or unwanted contact with the cutting element 136 before the user is ready to use the cutting element 136. Alternatively, or in addition thereto, a removeable cover 152 may preserve sterility of a cutting element 136 prior to use.

Figure 100:
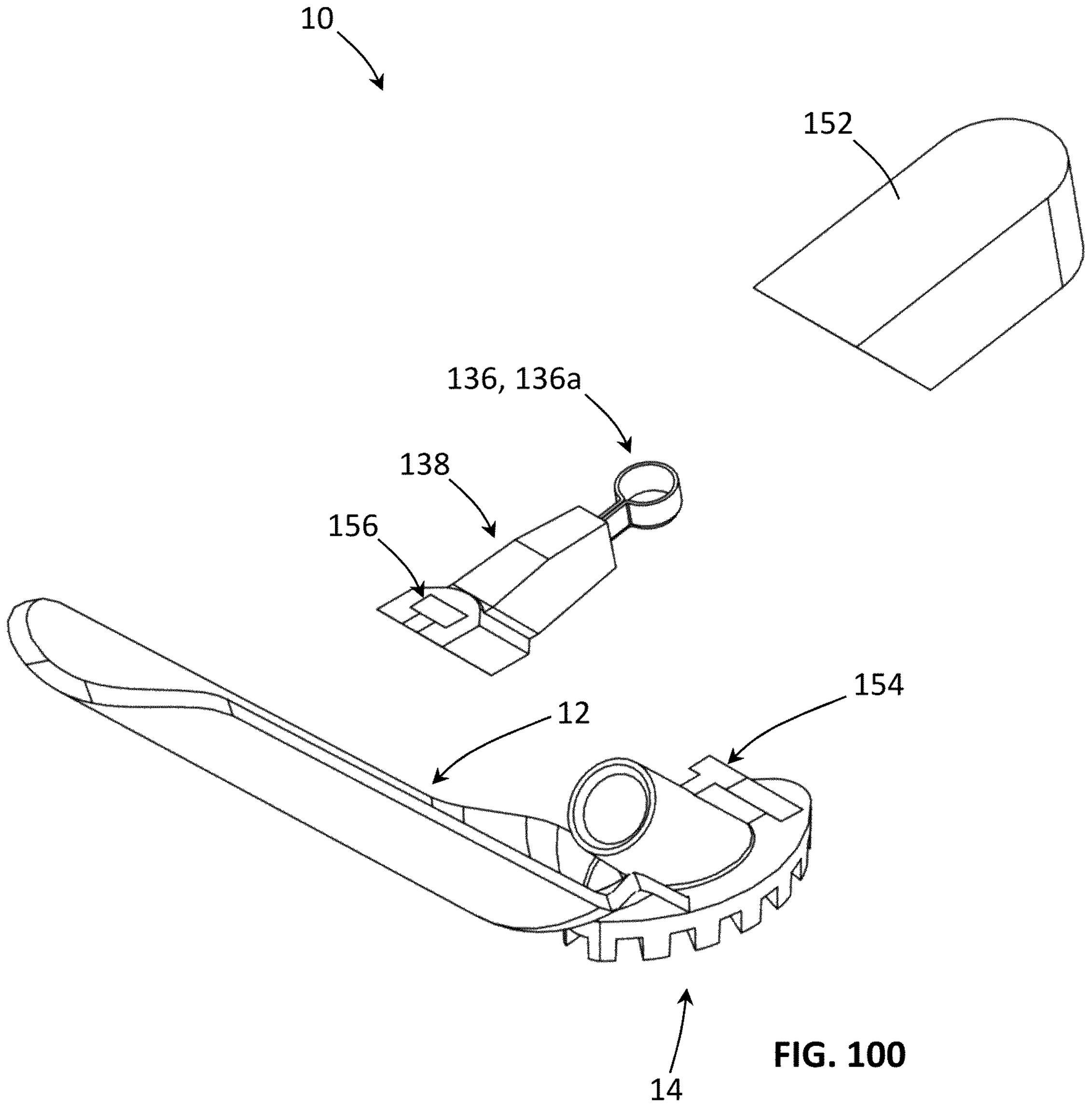
FIG. 100 is an exploded perspective view of another alternative embodiment of a wound-care device.
Figure 101:
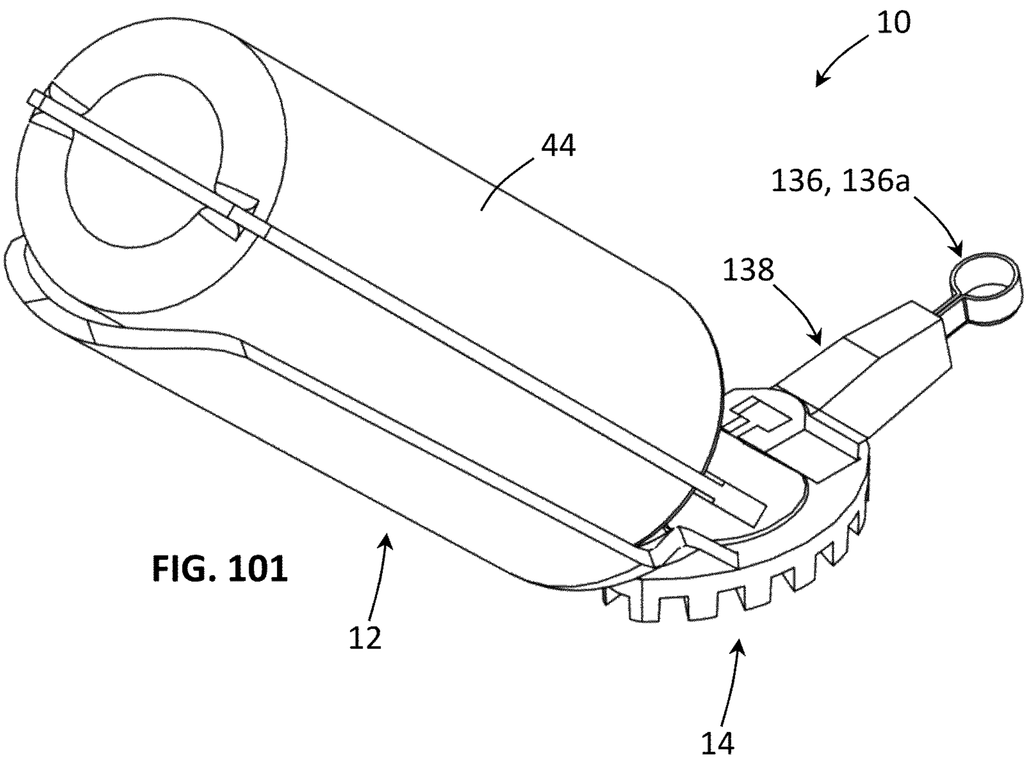
FIG. 101 is a perspective view of the wound-care device of FIG. 100 in an assembled configuration with the protective cover removed and a fluid reservoir installed.
Figure 102:
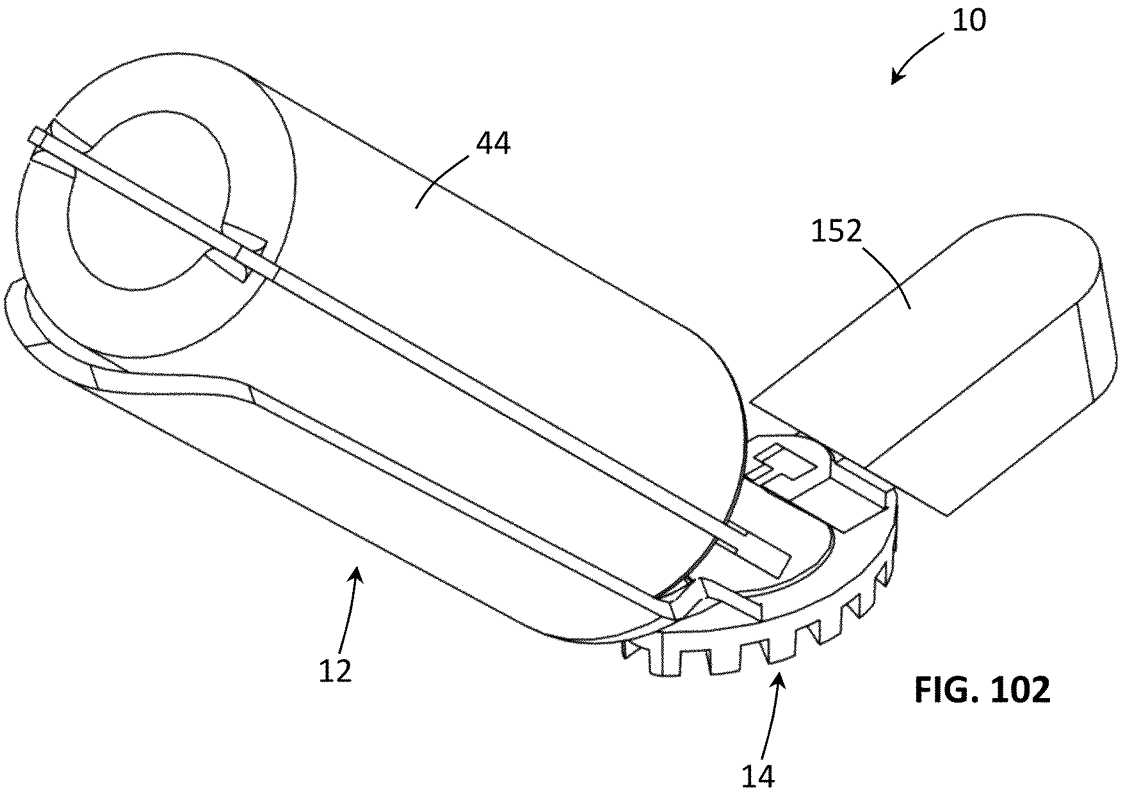
FIG. 102 is a perspective view of the wound-care device of FIG. 100 in an assembled configuration with a fluid reservoir installed.

Referring to FIGS. 100-102, in selected embodiments, a main body 12 that is simplified and head 14 combination may include a cutting element 136 (e.g., a curette 136*a*, scalpel 136*b*, or the like) in addition to a contact surface 36. In such embodiments, an engagement mechanism 138 may selectively and/or removably secure a cutting element 136 to the rest of a head 14. For example, a main portion of a head 14 may include a rail 154 and an engagement mechanism 138 may include an aperture 156 shape to engage the rail 154. When the aperture 156 is slid onto the rail 154, the engagement mechanism 138 may frictionally and/or mechanically engage the rail 154 and, thereby, selectively and/or removably secure the cutting element 136 to the rest of the head 14.

Figure 103:
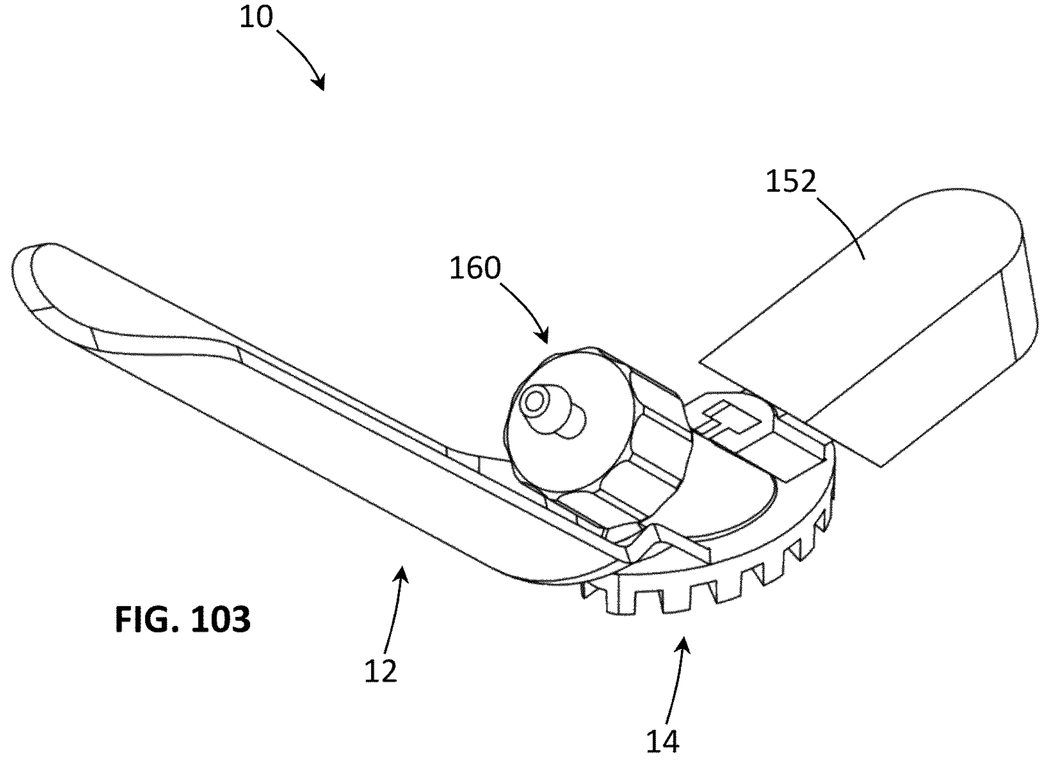
FIG. 103 is a perspective view of the wound-care device of FIG. 100 in an assembled configuration with a Luer-type connector installed.
Figure 104:
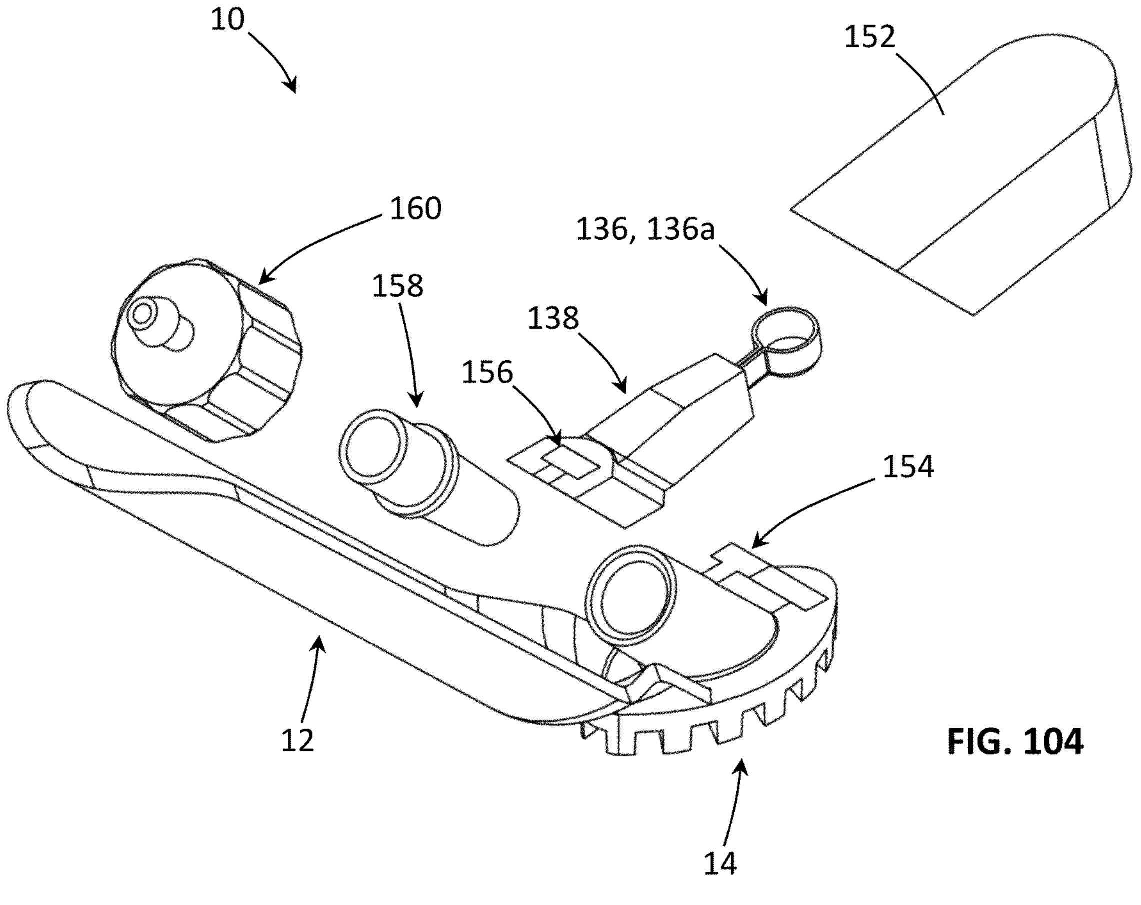
FIG. 104 is an exploded perspective view of the wound-care device of FIG. 103.

Referring to FIGS. 103 and 104, a wound-care device 10 may enable conduits 50 that are standard or commonly available intravenous tubing, intravenous connectors, saline bags, or the like to be used as part of a fluid system 16. For example, in certain embodiments, a kit corresponding to a wound-care device 10 may include an adaptor 158. The adaptor 158 may interface between an aperture 78 (e.g., an aperture 78 suitable for receiving an outlet 88 of a saline bullet) and a standard connector 160 (e.g., a Luer-type connector). That is, an adaptor 158 may have one end sized and shaped to be inserted within and frictionally engage an aperture 78 in a head and have a second, opposite end sized and shaped to receive and frictionally or mechanically engage a standard connector.

Referring to FIG. 105-116, in selected embodiments, a housing 24 may include a horn 28, a forward housing 162, and a rearward housing 164. The rearward housing 164 may be selectively removeable to provide access for inserting or removing one or more batteries 20 from within the main body 12 of the wound-care device 10. In certain embodiments, a first seal 166 may seal an interface between the forward housing 162 and the rearward housing 164 and resist the incursion of liquids or unwanted substances inside of the main body 12.

A housing 24 (e.g., a forward housing 162) may have include selected portions 168 formed in an overmolding process. Accordingly, the selected portions 168 may have different physical characteristics. For example, the selected portions 168 may be formed of or comprise elastomeric material that is softer to enhance comfort or grip for a user.

A horn 28 may extend from inside the housing 24 (e.g., inside the forward housing 162) to a location outside of the housing 24. In certain embodiments, a second seal 170 may seal an interface between the housing (e.g., the forward housing 162) and the horn 28 and resist the incursion of liquids or unwanted substances inside of the main body 12. In selected embodiments, one or more suspension elements 172 may hold the horn 28 in a desired location within the housing 24 (e.g., hold the horn 28 centered within the forward housing 162). For example, a first suspension element 172*a* may interface between the horn 28 and the housing 24 at a location forward of the second seal 170, while a second suspension element 172*b* may interface between the horn 28 and the housing 24 at a location rearward of the second seal 170.

In certain embodiments, the one or more suspension elements 172 may be formed of elastomeric material that may flex and/or compress to enable the horn 28 to move (e.g., oscillate, vibrate, etc.) with respect to the housing 24. Accordingly, not all of the motion generated by the motion generator 18 (e.g., by an electric motor 174 turning a shaft 176 with an eccentric weight 178 applied thereto) positioned within the horn 28 may be transmitted from the horn 28 to the housing 24. That is, the one or more suspension elements 172 may enable the horn 28 to move somewhat independently with respect to the housing 24.

In selected embodiments, a main body 12 may comprise an internal frame 180. The internal frame 180 may be positioned within the housing 24. The internal frame 180 may provide a structure to which other component of the main body 12 may secure. For example, the internal frame 180 may define a battery bay for receiving one or more batteries 20. Accordingly, one or more battery terminals 182 may be secured to or supported by the internal frame 180. Alternatively, or in addition thereto, the internal frame 180 may provide a location for a controller 22 (e.g., a printed circuit board (PCB) 32, one or more integrated circuits, one or more processors (e.g., an application-specific integrated circuit (ASIC), a programmable logic controller (PLC), or the like), memory, or the like or a combination or subcombination thereof) may secure.

Figure 117:
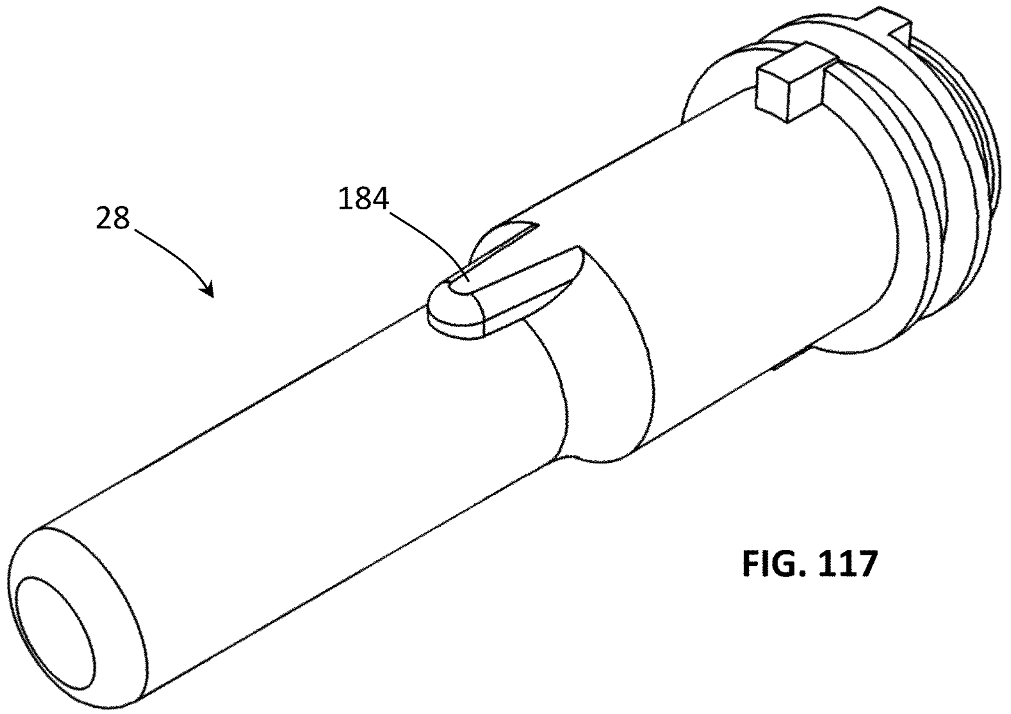
FIG. 117 is a perspective view of a horn of the wound-care device of FIG. 105.
Figure 118:
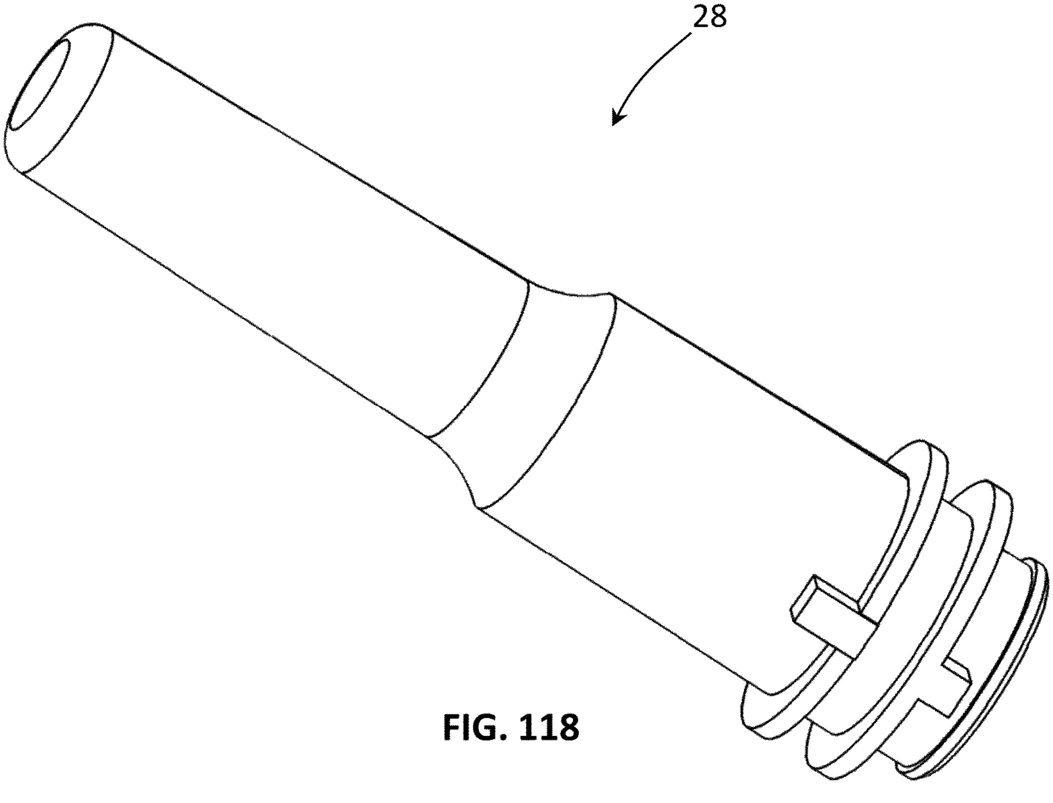
FIG. 118 is another perspective view of the horn of the wound-care device of FIG. 105.
Figure 119:
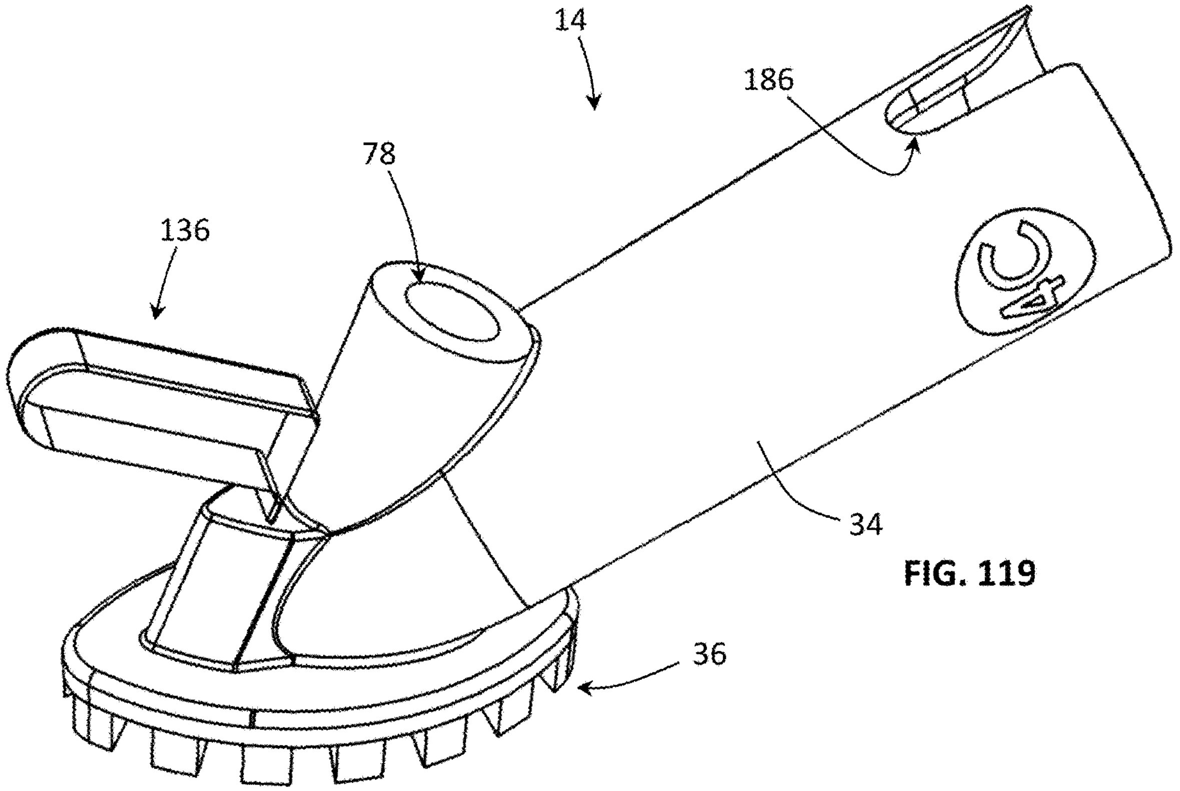
Figure 120:
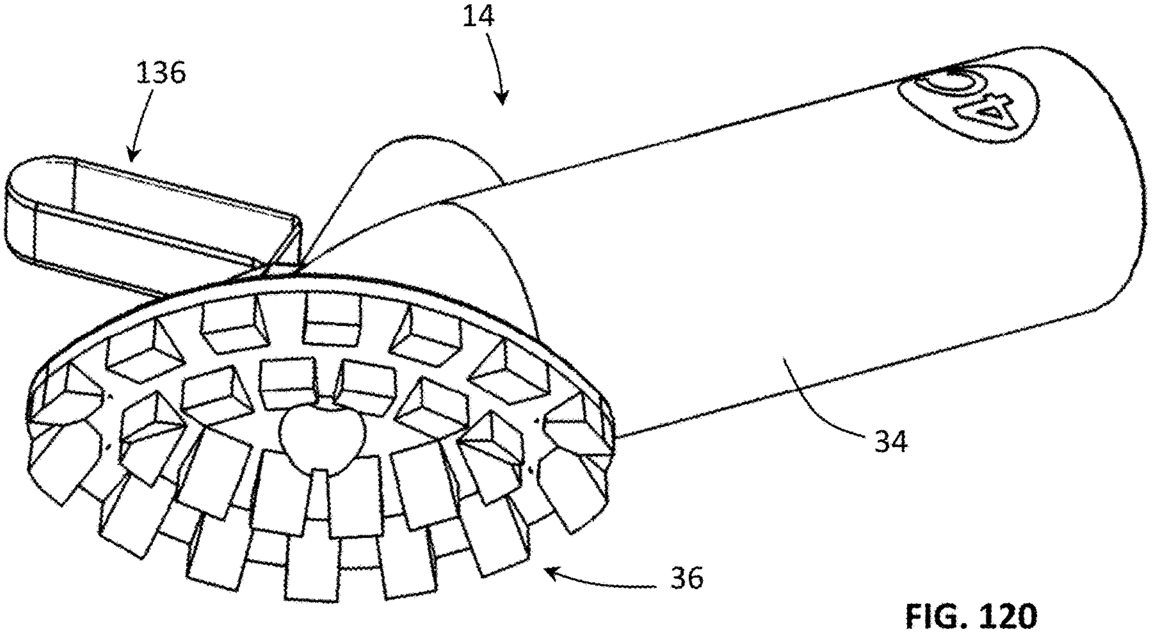
Figure 121:
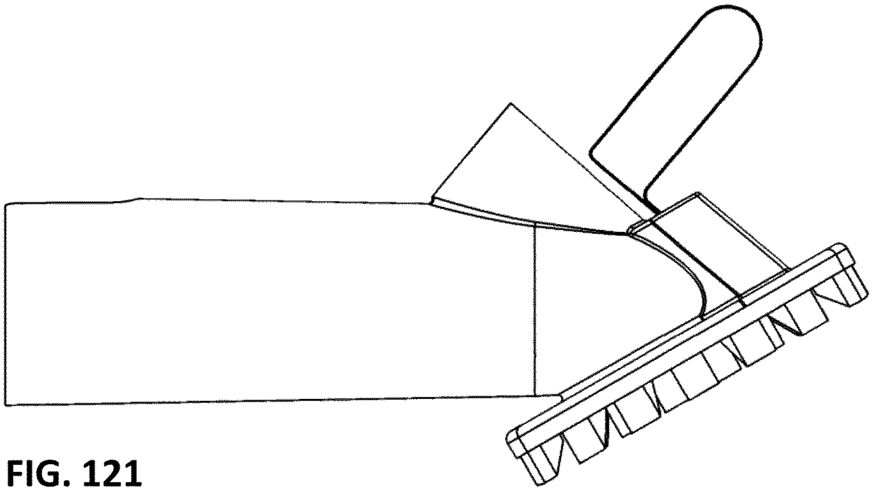
Figure 122:
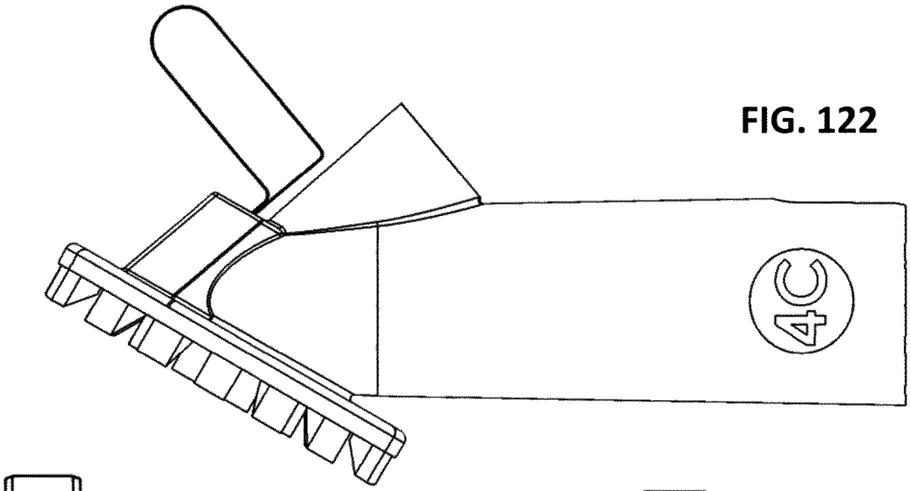
Figure 123:
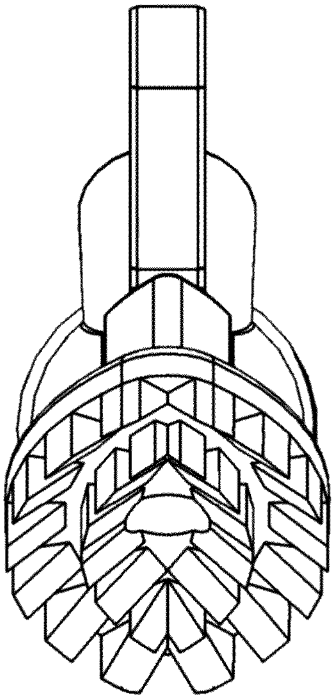
Figure 124:
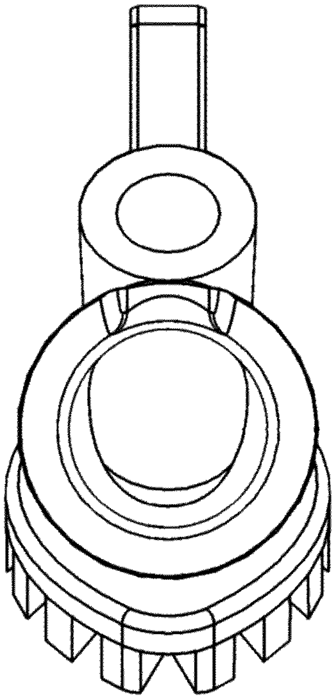
Figure 125:
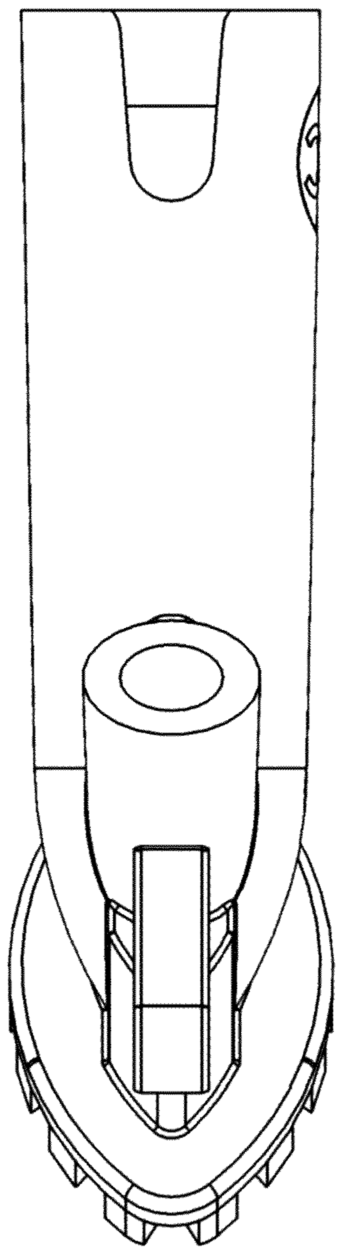
Figure 126:
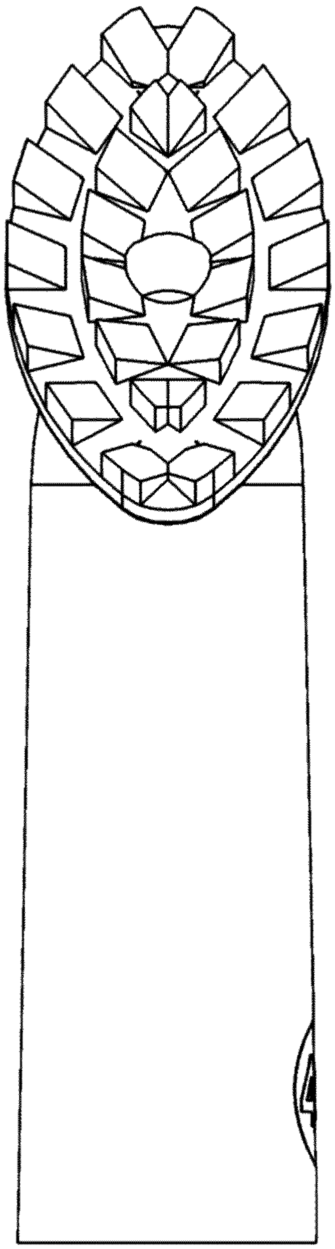
Figure 127:
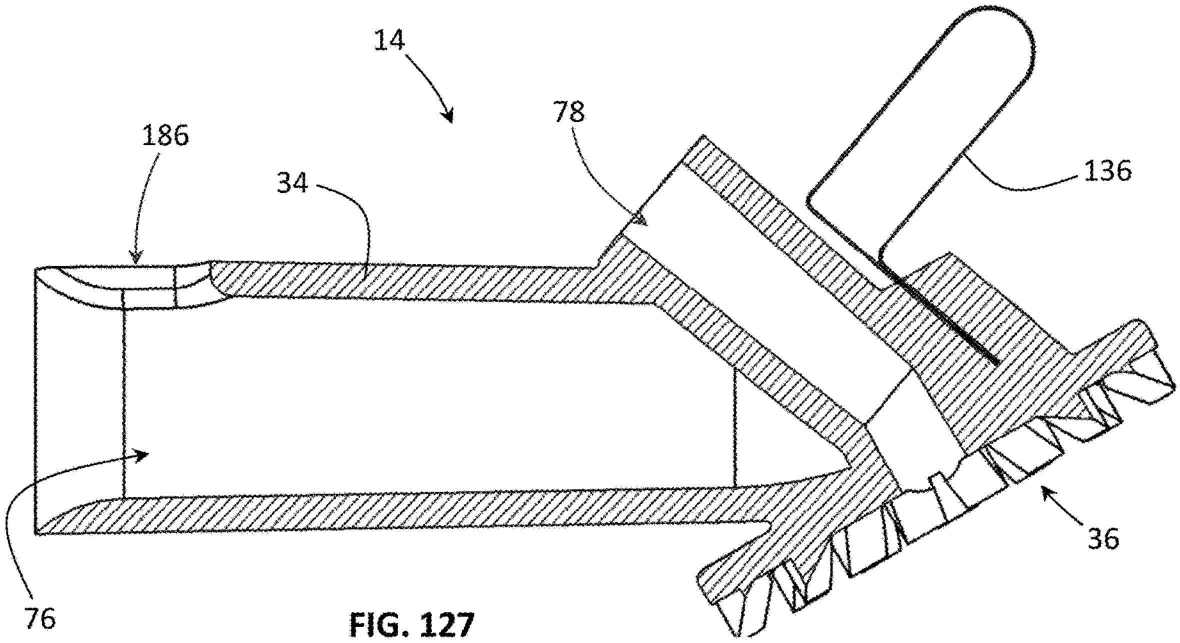
Figure 128:
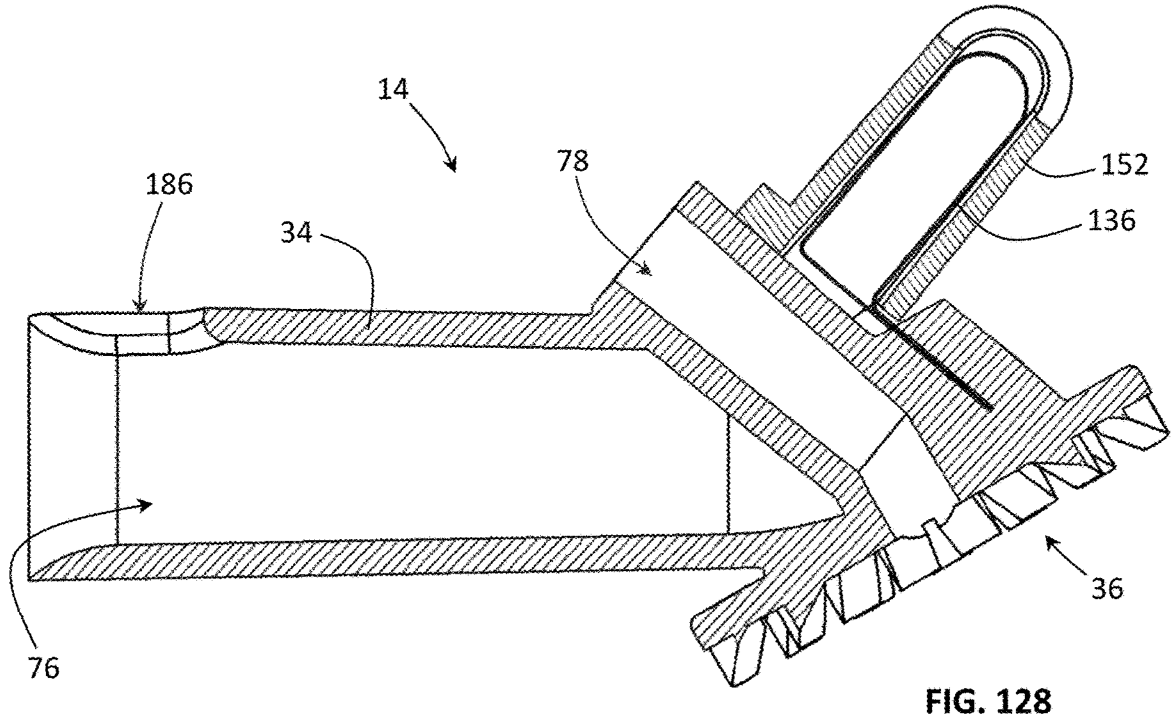
Figure 129:
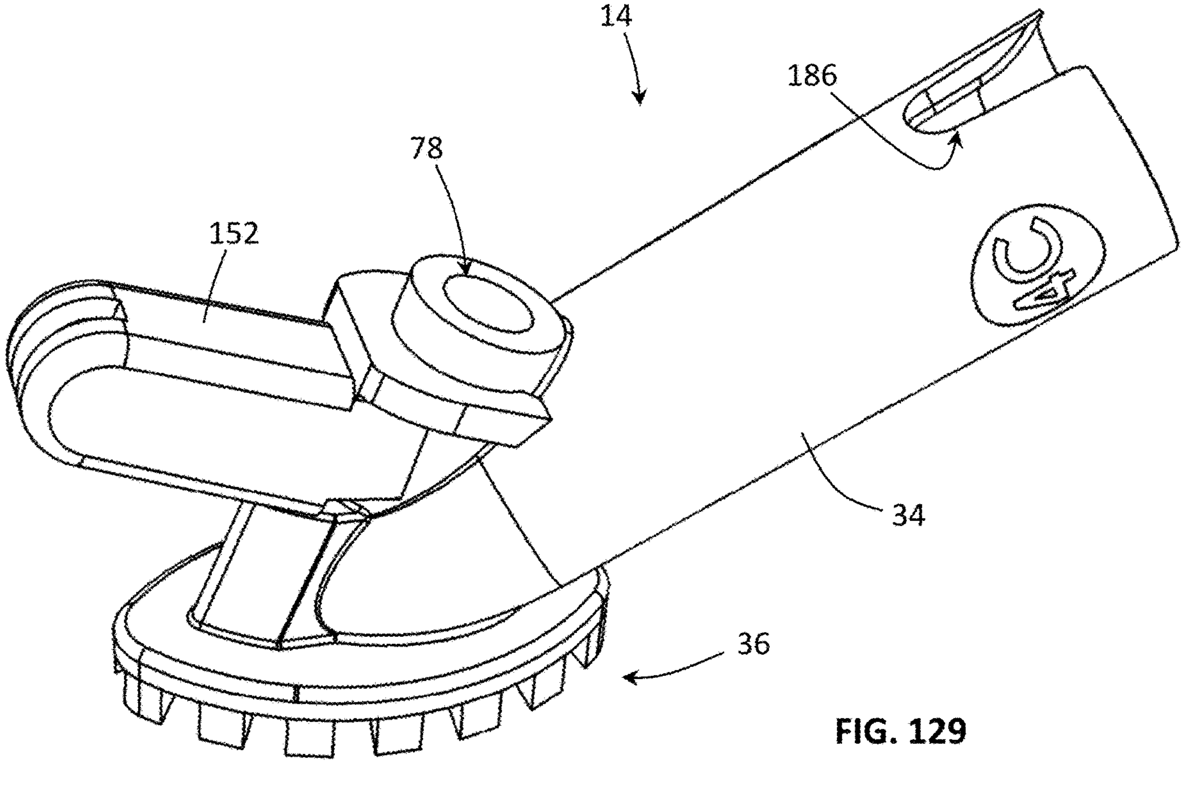

Referring to FIGS. 117-119, in certain embodiments, a horn 28 may include a first alignment mechanism 184 (e.g., an extension) that engages a head 14 to resist relative rotation of the head 14 about the horn 28. The head 14 may include a second alignment mechanism 186 (e.g., a recess) that engages the first alignment mechanism 184. Accordingly, the head 14 may have a keyed alignment with the horn 28 of a main body 12.

Referring to FIGS. 119-129, in certain embodiments, a head 14 may be formed to position a contact surface 36 close to a longitudinal axis of a horn 28 and close to a distal end of the horn 28. This may reduce a moment arm of the contact surface 36 with respect to the horn 28 and make it easier for a user to apply the contact surface 36 against a wound bed with a proper pressure and/or feel. It may also tend to reduce an amplitude of the motion at the contact surface 36 since the amplitude may increase with the length of the moment arm (i.e., a distance between the contact surface and the longitudinal axis of the horn 28)

A frame 34, contact surface 36, and aperture 78 of a head 14 may be monolithically formed of a polymeric material. In selected embodiments, a cutting element 136 may be insert molded into a head 14. The cutting element 136 may extend opposite the contact surface 36. Accordingly, by applying the head 14 in a first orientation, a user may apply the contact surface 36 to a wound bed. Alternative, by applying the head 14 in a second orientation (i.e., an orientation that is one hundred eighty degrees of rotation about the longitudinal axis of the horn 28 from the first orientation), a user may apply the cutting element to the wound bed. When the cutting element is not is use, a removeable cover 152 may ensure that the cutting element 136 does not come in contact with the user or the patient. In selected embodiments, a removeable cover 152 may releasably clip to or around a circular cylinder through which the aperture 78 extends through the head 14.

Referring to FIGS. 130-138, the contact surfaces 36 of the heads 14 may be different. For example, the head 14 illustrated may have contact surface 36 that is significantly smaller than the contact surface 36 of the head 14 shown in FIG. 119.

Referring to FIGS. 139-146, in selected embodiments, a contact surface 36 may be formed for aggressive debridement. For example, a contact surface 36 (e.g., a base 80 and extensions 82) may be formed from a sheet of metal (e.g., stainless steel) where the extensions 82 are bent to extend substantially orthogonal (or at a lesser angle) with respect to the base 80. The sheet of metal may be held in place by heat staking.

Referring to FIGS. 147-163, in selected embodiments, a contact surface 36 may be formed for aggressive cutting. For example, a contact surface 36 may be formed from a cutting element 136 (e.g., a metallic cutting element) that arcs away from the rest of the head 14. The opposing ends of the cutting element 136 may be held in place by heat staking. Alternatively, the opposing ends of the cutting element 136 may be held in place by being insert molded within a portion of the head 14.

Referring to FIGS. 164-171, in selected embodiments, a contact surface 36 may be formed for cleansing or desloughing. For example, a contact surface 36 (e.g., a base 80 and extensions 82) may be less aggressive in shape (e.g., comprise a series of serpentine ridges that form the extensions 82). Again, the extensions 82 may be a monolithic extension of the base 80 and the frame 34 of the head 14. In certain such embodiments, a cutting element 136 may be omitted. As a result, the head 14 may be well suited for use by a patient or less experienced or qualified caregiver.

Referring to FIGS. 173-178, a head 14 suitable for use on an open, deep wound or in undermined areas or tunneling wound-care situations may include a second alignment mechanism 186 as desired or necessary.

Referring to FIGS. 179A, 179B, and 180-184, a wound-care device 10 may be equipped to communicate wirelessly (e.g., via Bluetooth or other wireless protocol) or otherwise and pass information to a computer (e.g., to a mobile device, smart phone, tablet, or the like) and/or receive information from the computer. Interacting with the computer (e.g., with a specific application running on a mobile device) may enable a user (e.g., a patient) to better utilize the wound-care device 10. Alternatively, or in addition thereto, such interaction may be used to create electronic records that can be used to document use of the wound-care device 10. For example, the wound-care device 10 may communicate with the computer, which may then communicate with a remote server. Accordingly, by accessing records collected by the server, a medical professional may monitor usage of the wound-care device 10 and ensure compliance with a particular treatment regimen.

Referring to FIG. 179A, an embodiment of a first method 188 is illustrated. The first method 188 may include a power handle (i.e., a wound-care device 10) operating in a treatment mode. An embodiment of a second method 190 is also illustrated. The second method 190 may include a power handle operating in a treatment mode with Bluetooth enabled.

The first method 188 may include the user pressing and releasing a switch (e.g., switch 30). This may cause the motor (e.g., an electric motor of a motion generator 18) to run and an LED light to turn green or yellow, depending on a condition of a battery (e.g., battery 20). A pause may be enacted after the motor has run for 29.75 seconds and may last for 0.25 seconds. The motor may then run again until another pause is enacted. Thus, the process may repeat until the user presses and releases the switch, which may turn off both the motor and the LED light.

The second method 190 may include the user pressing and releasing a switch (e.g., switch 30). This may cause the LED light to turn green or yellow, depending on a condition of the battery (e.g., battery 20). It may also cause the power handle to perform the default or most recent input with respect to motor speed, cycle length, and pause duration. This process may be repeated. Session record keeping may be performed. When the user presses and releases the switch, both the motor and the LED light may turn off.

Referring to FIG. 179B, a diagram illustrates one embodiment of a third method 192 for using a power handle. The third method 192 may include a power handle in Bluetooth mode. The third method 192 may include a user pressing and holding a switch for two seconds and then releasing the switch. After the user presses and releases the switch, a blue LED light may slow flash to indicate the power handle is advertising. The power handle may transition to a paired condition and the blue LED light may turn solid to indicate the power handle is paired.

At some point, a user may open an app (i.e., a software application running on a mobile device) and identify a patient, which may involve a patient code. The patient code may be associated with the session, the motor speed, cycle length, and pause duration. The blue LED light on the power handle may fast flash to indicate data uploading from the app to the power handle. The blue LED light may also turn solid to indicate the upload is complete. The user may press and hold the switch for two seconds then release the switch to disconnect the Bluetooth. The blue LED light may turn off to indicate the Bluetooth pairing is disconnected.

Once the patient is identified and the pause duration, cycle length, and the motor speed are set, they may be stored in the power handle in association with the patient code. The app may record the association of the patient code with the session, motor speed, cycle length, and pause duration as a single record or as multiple records. The app may also download all records from the power handle. The blue LED light may fast flash to indicate the data is downloading. The blue LED light may turn solid to indicate the download is complete. The app may sort the records after the data is uploaded. The app may also display the records. The app may also send the records to a recipient via email.

Referring to FIG. 180, a flow diagram illustrates one embodiment of a fourth method 194 enabling at-home compliance. In the fourth method 194, a doctor may use software running on a computer to program a treatment regimen in the power handle. The doctor may then give the power handle to the patient to take home. The patient may download an app on their smart phone. The power handle may upload the treatment regimen to the app. The power handle may also record the sessions and the treatments. The power handle may upload the session records to the app. The patient may use the app to send an email with the data to the doctor. The doctor may receive the email from the patient. A doctor may open data in the email within a software application running on a computer. The data may be stored within the software application or may be printed and kept with the patient file.

If the patient does not have access to the internet or a smart phone, the patient may clean the wound themselves. The power handle may record data from treatment sessions such as date, time, and duration. Thereafter, the patient may visit the doctor, and the session records may be transferred from the power handle to a software application running on a computer.

Referring to FIG. 181, screen shots 196 and corresponding flow are illustrated for an app (i.e., a software application running on a mobile device) where a medical professional (e.g., a doctor or nurse) has set up a treatment regimen. The screen shots 196 and the flow corresponding thereto may comprise a welcome screen 196*a*, a pairing screen 196*b*, a selection screen 196*c*, a photograph screen 196*d*, a timer screen 196*e*, a return to the photograph screen 196*d*, a return to the selection screen 196*c*, a send screen 196*f*, and a finish screen 196*g*.

The pairing screen 196*b* may enable a user to pair the app with a power handle, thereby enabling the power handle to upload the treatment regimen. The selection screen 196*c* may enable the user to select a first wound to clean and the power of the power handle may be set via the paired connection. The photograph screen 196*d* may enable the user to photograph the first wound at the start. The timer screen 196*e* activates a timer. The timer may only count when the motor is running. Returning to the photograph screen 196*d*, the user may take another photograph of the first wound. Returning to the selection screen 196*c*, the user may select a second wound. Thereafter, the app may sound out the treatment time and may only record treatment when the motor is running. At the end of a session, the app may save data by treatment regimen and time and the send screen 196*f* may enable the user to send the data to a doctor via email or to an electronic medical record (EMR) system. The finish screen 196*g* may indicate to the user that the process is finished.

Referring to FIG. 182, screen shots 196 and corresponding flow are illustrated for an app (i.e., a software application running on a mobile device) where a user (e.g., a patient or family member of a patient) sets up a treatment regimen. The flow may comprise a welcome screen 196*a*, a pairing screen 196*b*, a username screen 196*h*, a treatment-defining screen 196*i*, a photograph screen 196*d*, a timer screen 196*e*, a return to the photograph screen 196*d*, and a selection screen 196*c*.

The pairing screen 196*b* may enable a user to pair the app with a power handle. The app may enable the user to set the treatment regimen or to use a default. The username screen 196*h* may prompt the user to enter a username. The treatment-defining screen 196*i* may enable the user to drag a red dot to a wound site on an illustrated body. The treatment-defining screen 196*i* may further open a window enabling a user to set time and power for the wound at issue and may allow the user to add another wound site on the illustrated body. The treatment-defining screen 196*i* may enable a user to double click on a red dot to set the time and power for the corresponding wound site. The photograph screen 196*d* may enable the user to photograph a wound at the start. The timer screen 196*e* activates a timer. The timer may only count when the motor is running. Returning to the photograph screen 196*d*, the user may take a second photograph of the wound. Thereafter, the user may use the selection screen 196*c* to select a second wound to continue treatment.

Referring to FIG. 183, a flow diagram illustrates one embodiment of a fifth method 198 enabling care-giver compliance. In the fifth method 198, a first caregiver may have a first power handle and a first mobile device (e.g., a smart phone) running an app. A second caregiver may have a second power handle and a second mobile device (e.g., a smart phone) running the app. The first caregiver and/or the second caregiver may visit a patient at the patient's home. The respective power handles may be paired with the respective mobile devices. The app on the first mobile device or the app on the second mobile may record data for each patient during treatment and push the data to the cloud. A doctor may use a computer (e.g., a computer running a software application) to pull data from the cloud. The software application may also connect the data to an electronic medical record (EMR) system.

Referring to FIG. 184, a flow diagram illustrates a sixth method 200 enabling caregiver compliance. In the sixth method 200, each room in a clinical setting may have its own power handle and a paired device (e.g., a smart phone) running an app. Each patient may be signed into the app by a caregiver. Each paired device may push data to the cloud during treatment. A separate room may contain a doctor that may have a computer running a software application that pulls the data from the cloud. The software application may connect the data to an electronic medical record (EMR) system.

The flowcharts of FIGS. 5, 15, 16, 89, 90, 179A, 179B, and 180-184 illustrate the functionality and/or use of devices and systems. It should be noted that, in some alternative implementations, the functions noted in the blocks may occur out of the order noted in the Figures. In certain embodiments, two blocks shown in succession may, in fact, be executed substantially concurrently, or the blocks may sometimes be executed in the reverse order, depending upon the functionality involved. Alternatively, or in addition thereto, certain steps or functions may be omitted if not needed.

Referring to FIGS. 185 and 186, in selected embodiments, a device 10 may be provided or used in combination with one or more disposable (e.g., single use) sleeves 202 so that the device 10 or portions of the device 10 (e.g., a main body 12 or handle portion 12) may be reusable between patients safely without contamination of the device 10. In such embodiments, to configure (e.g., assemble) a device 10 for use, a new and/or clean (e.g., sterile) head 14 and sleeve 202 may be applied to a main body 12 so that all surfaces coming in contact with a patient and a care-giver are clean. In certain embodiments, a sleeve 202 may cover a horn 28 and a housing 24 and a head 14 may slide over the sleeve 202 when it is installed on the horn 28.

That is, a head 14 may include a frame 34 and a contact surface 36. The frame 34 may engage the horn 28. For example, the frame 34 may have an aperture 76 shaped and sized to selectively receive (e.g., frictionally engage via mating tapers) the horn 28 and, thereby, conduct vibrations, oscillations, and/or reciprocations that originate with a motion generator 18 to the contact surface 36. When a sleeve 202 is used in such an arrangement, the aperture 76 in the frame 34 may receive therewithin the first end 204 of the horn 28 covered by the sleeve 202 such that a portion of the sleeve 202 is positioned between an interior surface 206 of the aperture 76 and an exterior surface 208 of the first end 204 of the horn 28.

References in the specification to "one embodiment," "an embodiment," "an example embodiment," "selected embodiments," "certain embodiments," or the like, indicate that the embodiment or embodiments described may include a particular feature, structure, or characteristic, but every embodiment may not necessarily include the particular feature, structure, or characteristic. Such phrases are not necessarily referring to the same embodiment. Moreover, when physically possible or desired, it is understood that features, structures, or characteristic described in the context of one embodiment may be applied to or incorporated within one or more other embodiments. For example, any contact surface 36 shown or described in connection with one embodiment of a wound-care device 10 or head 14 may be used on any other embodiment of a wound-care device 10 or head 14.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

The invention claimed is:

1. A method comprising:

obtaining components of a wound-care device, the components comprising a handle having a first end and a second end opposite the first end, a disposable sleeve, and a disposable head comprising projections and an aperture, the aperture configured to receive the first end of the handle therewithin;

assembling the wound-care device for use, the assembling comprising covering the handle with the disposable sleeve, and installing the disposable head on the first end of the handle such that a portion of the disposable sleeve is positioned between an interior surface of the aperture and an exterior surface of the first end; and disturbing a wound bed by contacting the wound bed with the projections.

2. The method of claim 1, wherein the disposable head further comprises a base having a front side and a backside.

3. The method of claim 2, wherein:

the projections extend away from the front side of the base; and the base and the projections are monolithically formed of polymeric material.

4. The method of claim 1, wherein the disposable head further comprises:

a base having a front side and a back side; and a cutting element extending away from the back side of the base.

5. The method of claim 1, wherein the handle comprises a motion generator housed within the first end thereof, the motion generator comprising an electric motor.

6. The method of claim 1, further comprising causing, by a motion generator, at least one of vibration, oscillation, or reciprocation of the projections at a sonic frequency in a range of about 100 Hz to about 1000 Hz.

7. The method of claim 6, further comprising generating at least one of the vibration, oscillation, or reciprocation of the projections by turning on the motion generator.

8. The method of claim 7, wherein the disturbing comprises contacting the wound bed with the projections while the motion generator is turned on.

9. The method of claim 1, further comprising pairing the handle with a software application running on a computing device.

10. A wound-care device comprising:

a handle having a first end and a second end opposite the first end;

the handle extending in a first direction from the first end to the second end;

a disposable sleeve;

a disposable head secured to the first end of the handle; and the disposable head comprising a plurality of projections and an aperture, the aperture receiving therewithin the first end covered by the disposable sleeve such that a portion of the disposable sleeve is positioned between an interior surface of the aperture and an exterior surface of the first end.

11. The wound-care device of claim 10, wherein the disposable head further comprises a base having a front side and a back side.

12. The wound-care device of claim 11, wherein:

the projections extend away from the front side of the base; and the base and the projections are monolithically formed of polymeric material.

13. The wound-care device of claim 12, wherein the disposable head further comprises a cutting element extending away from the back side of the base.

14. A wound-care system comprising:

a handle having a first end and a second end opposite the first end;

a first disposable head comprising a plurality of debriding projections;

the first disposable head further comprising an aperture configured to receive the first end therewithin to selectively secure the first disposable head to the handle; and a first disposable sleeve sized and shaped to cover the handle such that, when the handle, the first disposable head, and the first disposable sleeve are assembled, a portion of the first disposable sleeve is positioned between an interior surface of the aperture and an exterior surface of the first end.

15. The wound-care system of claim 14, further comprising a motion generator configured to produce at least one of vibration, oscillation, or reciprocation of the plurality of debriding projections at a sonic frequency in a range of about 100 Hz to about 1000 Hz.

* * * * *